US012623099B2

(12) United States Patent
Webb et al.

(10) Patent No.: US 12,623,099 B2
(45) Date of Patent: May 12, 2026

(54) SYSTEMS AND METHODS FOR AUTOMATED RESPIRATOR

(71) Applicant: 3M INNOVATIVE PROPERTIES COMPANY, St. Paul, MN (US)

(72) Inventors: Richard C. Webb, St. Paul, MN (US); Andrew W. Long, Woodbury, MN (US); Jessica L. Tredinnick-Higgins, St. Paul, MN (US); David R. Stein, White Bear Lake, MN (US); Daniel B. Taylor, White Bear Lake, MN (US); Jacob P. Vanderheyden, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1333 days.

(21) Appl. No.: 17/309,789

(22) PCT Filed: Dec. 20, 2019

(86) PCT No.: PCT/IB2019/061206
§ 371 (c)(1),
(2) Date: Jun. 18, 2021

(87) PCT Pub. No.: WO2020/129017
PCT Pub. Date: Jun. 25, 2020

(65) Prior Publication Data
US 2022/0080228 A1 Mar. 17, 2022

Related U.S. Application Data

(60) Provisional application No. 62/942,243, filed on Dec. 2, 2019, provisional application No. 62/930,388, filed
(Continued)

(51) Int. Cl.
*A62B 27/00* (2006.01)
*A62B 9/00* (2006.01)
(Continued)

(52) U.S. Cl.
CPC .............. *A62B 27/00* (2013.01); *A62B 9/006* (2013.01); *A62B 18/02* (2013.01); *A62B 18/025* (2013.01);
(Continued)

(58) Field of Classification Search
CPC ......... A62B 27/00; A62B 9/006; A62B 18/02; A62B 18/025; A62B 18/10; A61M 2205/15
(Continued)

(56) References Cited

U.S. PATENT DOCUMENTS

| | | | |
|---|---|---|---|
| 4,846,166 A | 7/1989 | Willeke | |
| 10,445,747 B2 | 10/2019 | Farioli Brioschi | |

(Continued)

FOREIGN PATENT DOCUMENTS

| | | |
|---|---|---|
| WO | WO 1987-002898 | 5/1987 |
| WO | WO 2015-179156 | 11/2015 |

(Continued)

OTHER PUBLICATIONS

"Grove Sound Sensor ", Seeed Technology Co. Ltd. [online], (Date unknown but believed to be prior to the date of the filing of the present application), [retrieved from the internet on Aug. 15, 2021], URL <http://wiki.seeedstudio.com/Grove-Sound_Sensor>, 15 pages.
(Continued)

*Primary Examiner* — Justine R Yu
(74) *Attorney, Agent, or Firm* — Katherine M. Scholz

(57) ABSTRACT

There is provided a computing device comprising: at least one processor; and a memory comprising instructions that, when executed by the at least one processor, cause the at least one processor to: receive first sensor data indicative of a gas characteristic in a sealed space formed by a face of a wearer and a negative pressure reusable respirator; receive second sensor data indicative of a position of at least one
(Continued)

valve in the negative pressure reusable respirator; determine comparative data by comparing the first sensor data to the second sensor data; and perform one or more actions in response to the comparative data. There is also provided a system using such computing device.

18 Claims, 16 Drawing Sheets

Related U.S. Application Data on Nov. 4, 2019, provisional application No. 62/813, 724, filed on Mar. 4, 2019, provisional application No. 62/784,012, filed on Dec. 21, 2018.

(51) Int. Cl.

| | | |
|---|---|---|
| *A62B 18/02* | (2006.01) | |
| *A62B 18/10* | (2006.01) | |
| *G01N 33/00* | (2006.01) | |
| *G08B 21/18* | (2006.01) | |
| *G01L 17/00* | (2006.01) | |

(52) U.S. Cl.
CPC ......... *A62B 18/10* (2013.01); *G01N 33/0027* (2013.01); *G08B 21/182* (2013.01); *A61M 2205/15* (2013.01); *G01L 17/00* (2013.01)

(58) Field of Classification Search
USPC ....................................................... 73/40, 46
See application file for complete search history.

(56) References Cited

U.S. PATENT DOCUMENTS

| | | | |
|---|---|---|---|
| 2004/0168689 A1 | 9/2004 | Kuriyama | |
| 2006/0130835 A1* | 6/2006 | Truschel | A61M 16/204 |
| | | | 128/204.23 |
| 2011/0270085 A1 | 11/2011 | King | |
| 2016/0166859 A1 | 6/2016 | Rachapudi | |
| 2016/0303405 A1 | 10/2016 | Elliott et al. | |
| 2017/0296094 A1 | 10/2017 | Fonzi | |
| 2018/0008849 A1 | 1/2018 | Baker | |
| 2018/0311517 A1* | 11/2018 | Patil | A62B 18/02 |
| 2019/0064750 A1* | 2/2019 | Awiszus | A43B 7/32 |

FOREIGN PATENT DOCUMENTS

| | | | | |
|---|---|---|---|---|
| WO | WO 2016-040954 | | 3/2016 | |
| WO | WO-2017040397 A1 * | | 3/2017 | A41D 13/0002 |
| WO | WO 2017-069756 | | 4/2017 | |
| WO | 2017223438 | | 12/2017 | |
| WO | WO 2019-046696 | | 3/2019 | |
| WO | WO 2019-160535 | | 8/2019 | |
| WO | WO-2019160535 A1 * | | 8/2019 | A62B 18/08 |
| WO | WO 2020-128952 | | 6/2020 | |
| WO | WO 2020-129006 | | 6/2020 | |
| WO | WO 2020-174387 | | 9/2020 | |

OTHER PUBLICATIONS

"Sound Sensor Module", Sun Founder [online] (Date unknown but believed to be prior to the date of the filing of the present application), [retrieved from the internet on Aug. 15, 2021], URL <https://www.sunfounder.com/sound-sensor-module.html>, 5 pages.
International Search Report for PCT International Application No. PCT/IB2019/061206, mailed on Jun. 24, 2020, 6 pages.
International Search Report for PCT International Application No. PCT/IB2019/061195, mailed on Apr. 3, 2020, 4 pages.
Butler, Kathryn M. et al., "Real-time monitoring of total inward leakage of respiratory equipment used by emergency responders : workshop proceedings," National Institute of Standards and Technology (NIST), Dec. 31, 2010, 111 pages.

* cited by examiner

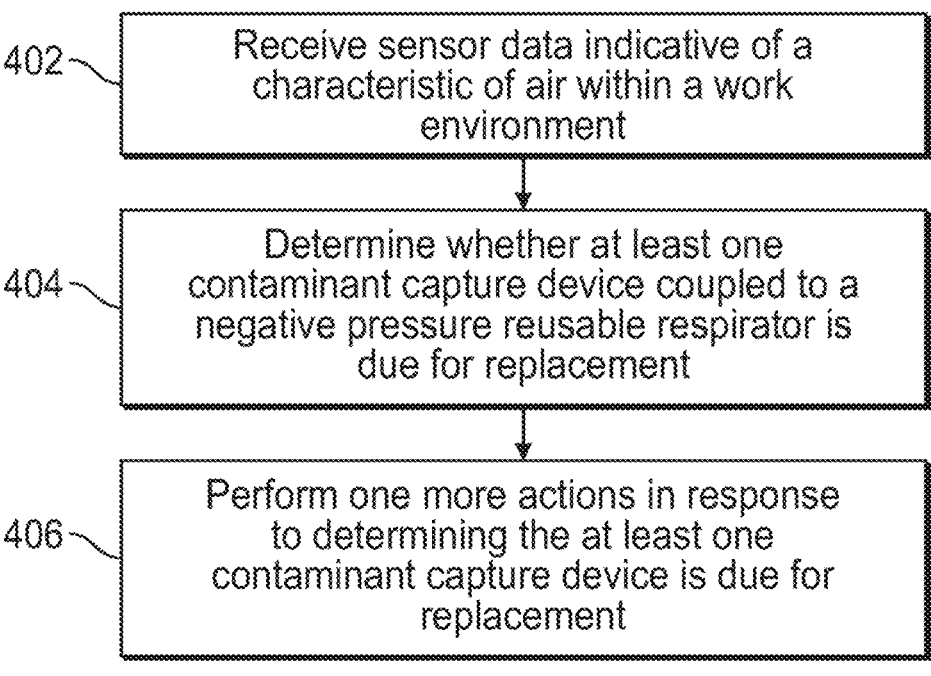

402 — Receive sensor data indicative of a characteristic of air within a work environment 404 — Determine whether at least one contaminant capture device coupled to a negative pressure reusable respirator is due for replacement 406 — Perform one more actions in response to determining the at least one contaminant capture device is due for replacement

FIG. 10

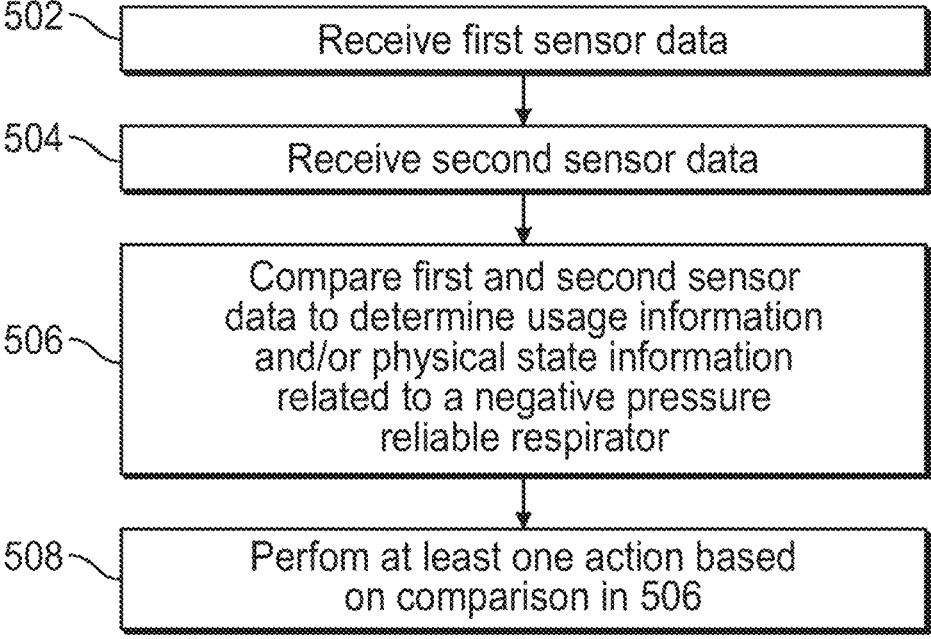

502 — Receive first sensor data

504 — Receive second sensor data

506 — Compare first and second sensor data to determine usage information and/or physical state information related to a negative pressure reliable respirator 508 — Perfom at least one action based on comparison in 506

FIG. 11

SYSTEMS AND METHODS FOR AUTOMATED RESPIRATOR

CROSS REFERENCE TO RELATED APPLICATIONS

This application is a national stage filing under 35 U.S.C. 371 of PCT/IB2019/, filed Dec. 20, 2019, which claims the benefit of U.S. Provisional Application No. 62/942,244, filed Dec. 2, 2019, U.S. Provisional Application No. 62/930,413, filed Nov. 4, 2019, U.S. Provisional Application No. 62/813, 724, filed Mar. 4, 2019, and U.S. Provisional Application No. 62/784,012, filed Dec. 21, 2018, the disclosure of which is incorporated by reference in its/their entirety herein.

TECHNICAL FIELD

The present disclosure relates to systems and methods for automated respirators, including sensing of gas characteristics and valve position within respirators and notifications related thereto.

BACKGROUND

Many work environments include hazards that may expose people working within a given environment to a safety event, such as a fall, breathing contaminated air, or temperature related injuries (e.g., heat stroke, frostbite, etc.). In many work environments, workers may utilize personal protective equipment (PPE) to help mitigate the risk of a safety event. Often, a worker may not recognize an impending safety event until the environment becomes too dangerous or the worker's health deteriorates too far. PPE that fits or is donned by a worker properly is important to help mitigate the risk of a safety event.

As used in industry language, a respirator worker seal check, also referred to as a user seal check or a wearer seal check, is a process by which a worker donning a respirator assesses the fit of their tight-fitting respirator for large-scale leaks. As defined by many regulatory bodies, including the US Occupational Safety and Health Administration (OSHA), a respirator worker seal check is distinctly different from a respirator fit test. A respirator fit test is an assessment of worker's suitability to fit a specific make and model of respirator, with the test administered by a trained person. Examples of respirator fit tests are 3M Qualitative Respirator Fit Tests using Bitrex and/or Saccharin, the TSI Porta-Count test. A worker seal check is intended to be a check carried out by a user (i.e. a worker or wearer donning the respirator), not requiring supervision by any other person, every time the user dons the respirator for use.

Worker seal checks are conducted as either negative seal checks, positive seal checks, or both on tight fitting respirators. The process involves the worker using their hands, or a mechanism on the respirator, to cover the inhalation/exhalation flow path(s) and then inhaling/exhaling to create a decrease/increase in pressure in the respirator. Workers assess adequate fit of the respirator based on their subjective assessment of how well the respirator holds pressure, the feeling of air flow around the seal, and the like.

A worker seal check helps inform a worker that they assembled and donned the respirator correctly, and as such, should be conducted every time a worker dons a respirator. However, workers sometimes fail or forget to conduct a worker seal check. Additionally, workers often desire additional confidence in the fit of their respirator, beyond their own subjective assessment of the worker seal check.

SUMMARY

In general, the present disclosure describes a system comprising a negative pressure reusable respirator configured to be worn by a wearer and to cover at least a mouth and a nose of the wearer to form a sealed space formed by a face of the wearer and the negative pressure reusable respirator, wherein the negative pressure reusable respirator comprises at least one valve; a first sensor configured to generate first sensor data indicative of a gas characteristic in a sealed space formed by a face of the wearer and the negative pressure reusable respirator; a second sensor configured to generate second sensor data indicative of a position of the at least one valve; and at least one computing device configured to provide comparative data by comparing the first sensor data to the second sensor data.

In another aspect, the present disclosure provides a computing device comprising: at least one processor; and a memory comprising instructions that, when executed by the at least one processor, cause the at least one processor to: receive first sensor data indicative of a gas characteristic in a sealed space formed by a face of a wearer and a negative pressure reusable respirator; receive second sensor data indicative of a position of at least one valve in the negative pressure reusable respirator; determine comparative data by comparing the first sensor data to the second sensor data; and perform one or more actions in response to the comparative data.

The details of one or more examples of the disclosure are set forth in the accompanying drawings and the description below. Other features, objects, and advantages of the disclosure will be apparent from the description and drawings, and from the claims.

BRIEF DESCRIPTION OF THE DRAWINGS

By way of example only, embodiments of the present disclosure will now be described below with reference to the accompanying drawings, in which:

FIG. 10 is a flowchart illustrating example operations of an example computing system, in accordance with various techniques of the present disclosure.

FIG. 11 is a flowchart illustrating example operations of an example computing system, in accordance with various techniques of the present disclosure.

Figure 1A:
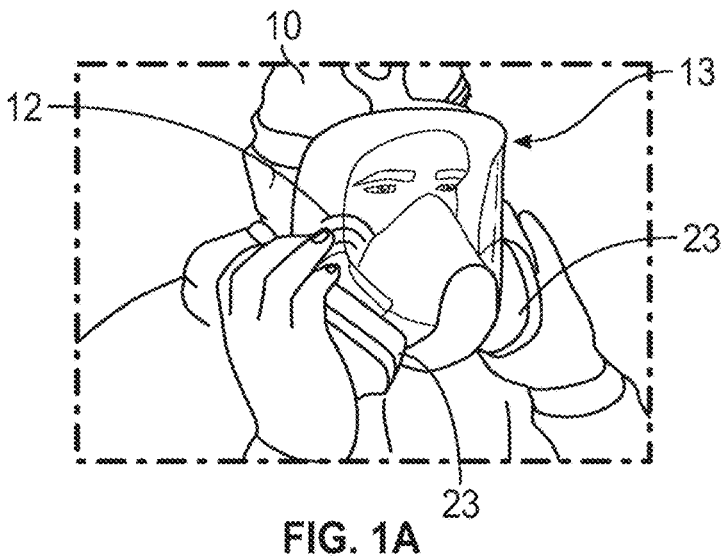
FIGS. 1A and 1B are a front perspective views of a wearer donning a full-face negative pressure reusable respirator having an accessory according to some embodiments of the present disclosure.

It is to be understood that the embodiments may be used and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Before any embodiments of the present disclosure are explained in detail, it is to be understood that the present disclosure is not limited in its application to the details of construction and the arrangement of components set forth in the following description. The present disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Any numerical range recited herein includes all values from the lower value to the upper value. For example, if a percentage is stated as 1% to 50%, it is intended that values such as 2% to 40%, 10% to 30%, or 1% to 3%, etc., are expressly enumerated. These are only examples of what is specifically intended, and all possible combinations of numerical values between and including the lowest value and the highest value enumerated are considered to be expressly stated in this application.

In the present detailed description, reference is made to the accompanying drawings, which illustrate specific embodiments in which the presently disclosed devices may be practiced. The illustrated embodiments are not intended to be exhaustive of all embodiments according to the present disclosure. It is to be understood that other embodiments may be utilized and structural or logical changes may be made without departing from the scope of the present disclosure. The following detailed description, therefore, is not to be taken in a limiting sense, and the scope of the present disclosure is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, terms "worker", "wearer" and "user" are used interchangeably.

The term "operably disposed" as used herein means that a component is directly or indirectly and removably or fixedly attached to another component. As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example.

Throughout the present disclosure where negative pressure reusable respirators is being referred to disclosure is applicable to full and half face negative pressure reusable respirators, full and half face positive pressure reusable respirators, and self-contained breathing apparatus.

Figure 1B:
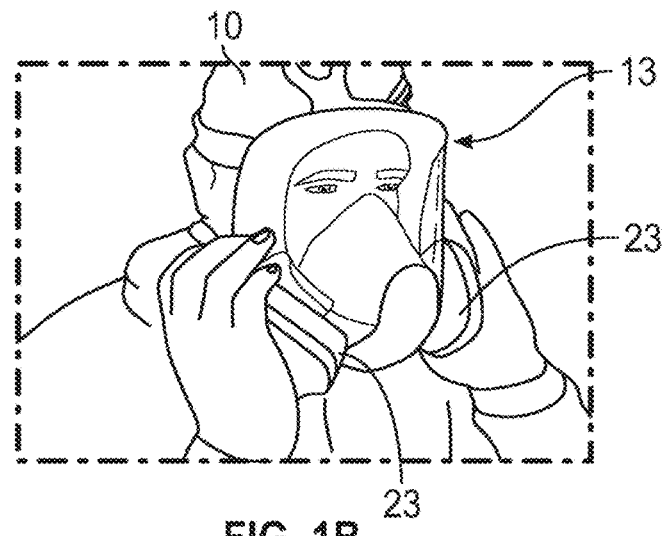

As shown in FIGS. 1A and 1B, the present disclosure provides a negative pressure reusable respirator 13 configured to be worn by a wearer 10 and to cover at least a mouth and a nose of the wearer 10 to form a sealed space formed by a face of the wearer 10 and the negative pressure reusable respirator 13. Negative pressure reusable respirators 13 useful in the present disclosure include at least one valve operably connected to at least one contaminant capture device 23.

Figure 2:
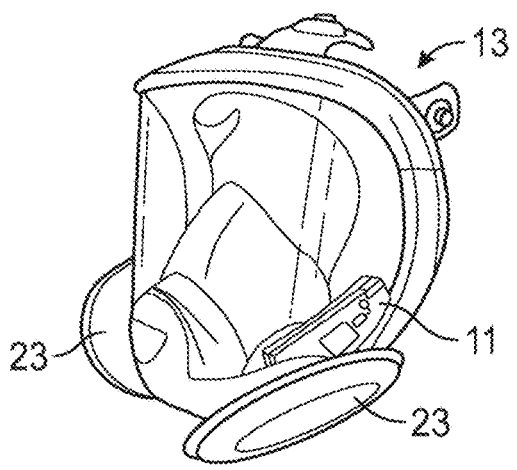
FIG. 2 is a front perspective view of a negative pressure reusable respirator having an accessory according to some embodiments of the present disclosure.
Figure 3A:
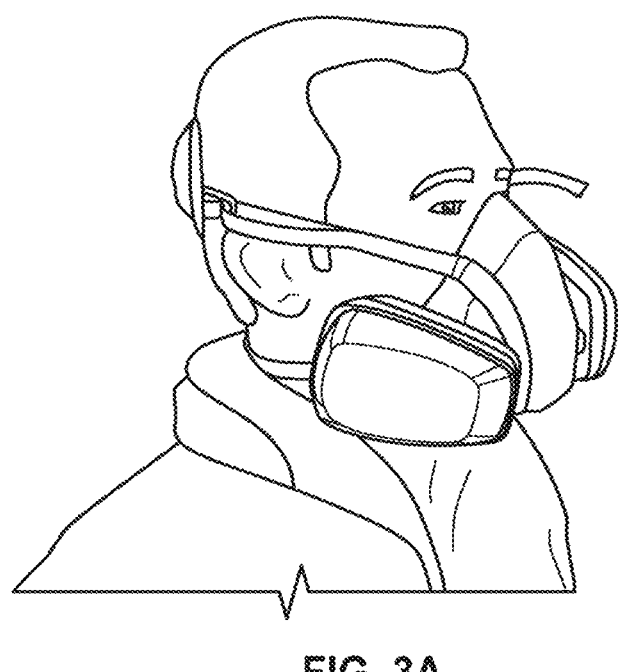
FIGS. 3A and 3B are a front perspective views of a wearer donning a half-face negative pressure reusable respirator having an accessory according to some embodiments of the present disclosure.
Figure 3B:
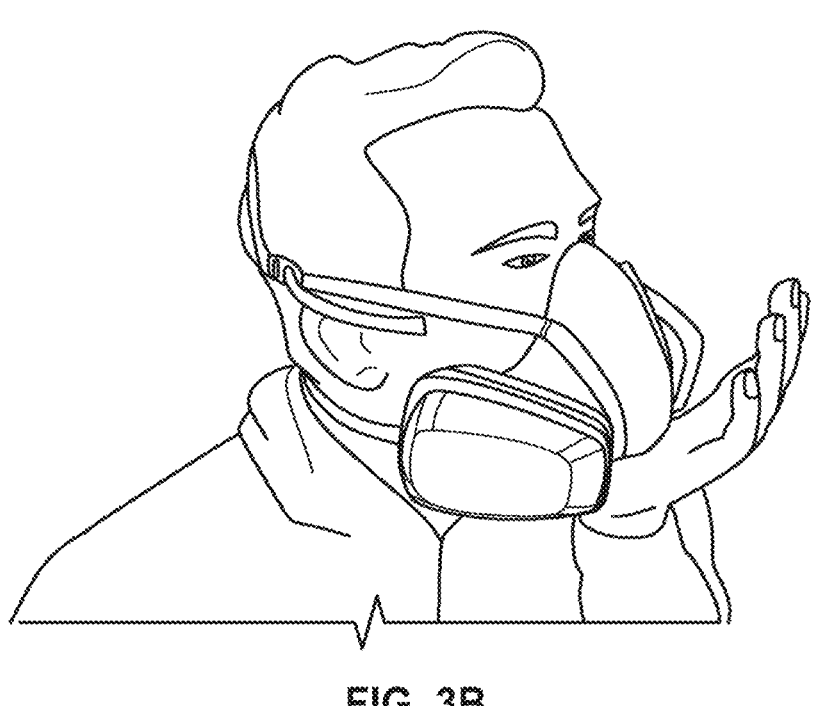
Figure 8:
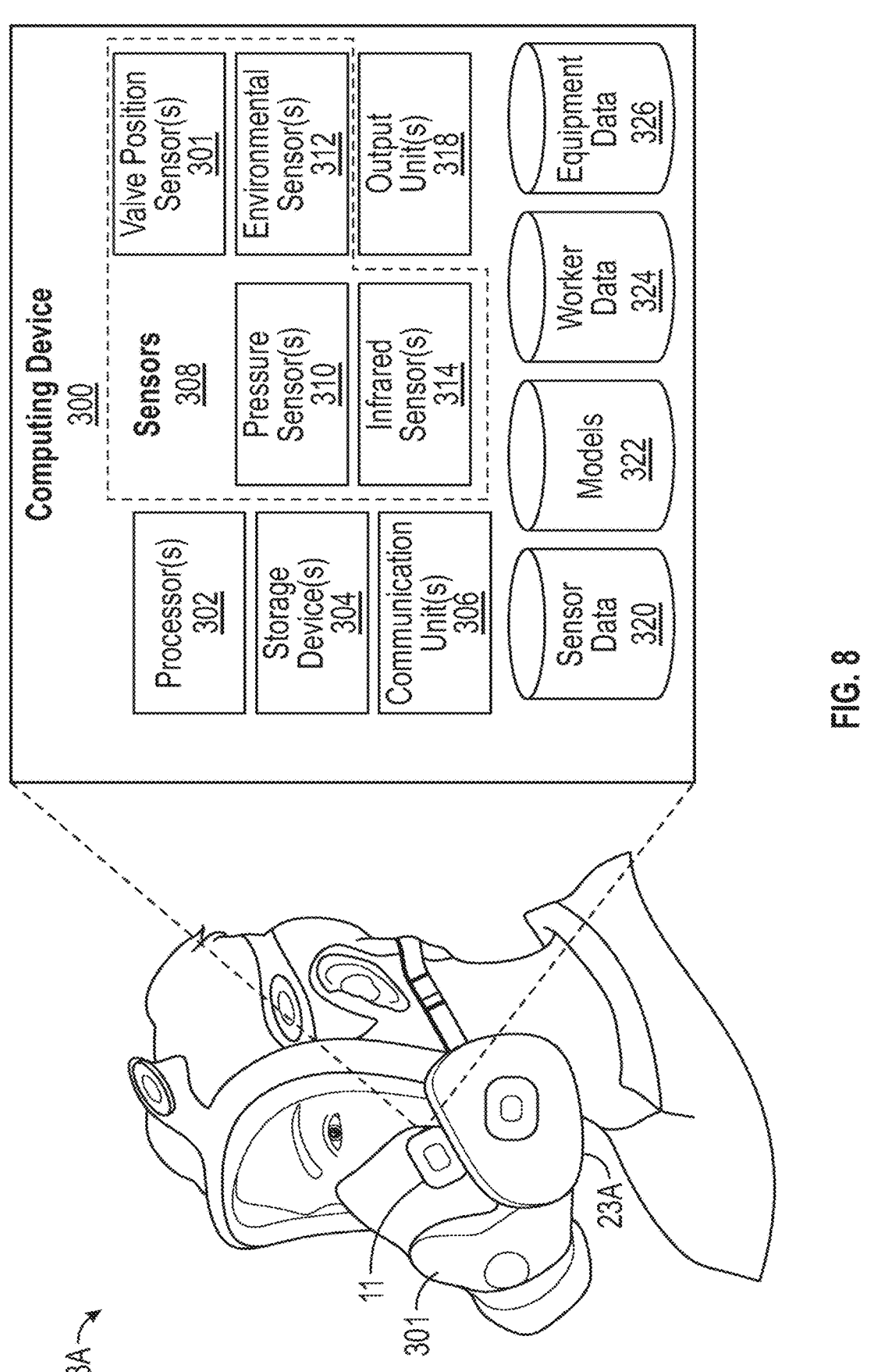
FIG. 8 is a conceptual diagram illustrating an example negative pressure reusable respirator, in accordance with various techniques of this disclosure.
Figure 9:
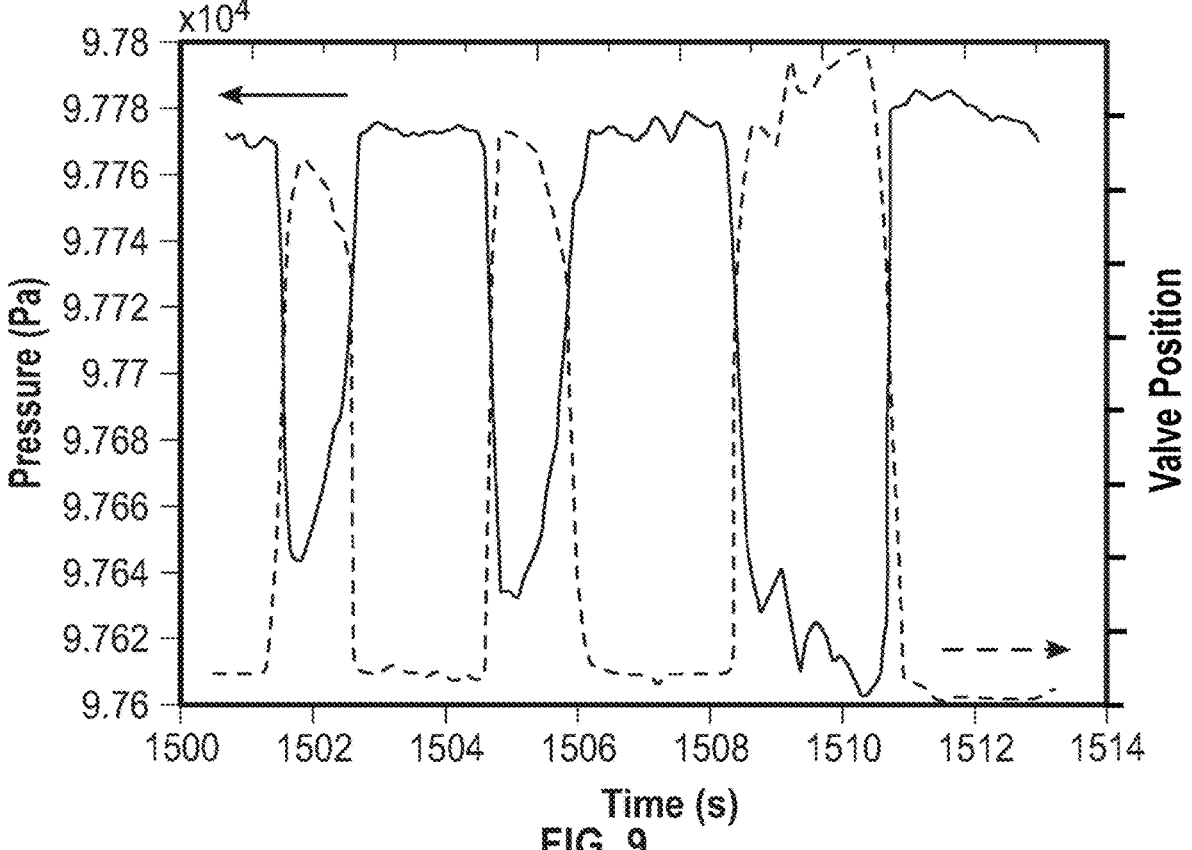
FIG. 9 is a plot of first and second sensor data according to the present disclosure as a function of time.

As shown in FIG. 2, the presently disclosed negative pressure reusable respirator 10 also includes at least one accessory 11. In some embodiments, accessory 11 is operably disposed within the sealed space. In some embodiments, accessory 11 is operably disposed on an external surface of the negative pressure reusable respirator 13. In some embodiments, accessory 11 includes a computing device 300 (as shown in FIG. 8). In some embodiments, accessory 11 includes at least one output device, such as for example, a speaker, a haptic device, a light, a graphic display device, and the like. Referring again to FIGS. 1A and 1B, after wearer 10 dons negative pressure reusable respirator 13, he/she can apply pressure to at least one contaminant capture device 23, in some embodiments two contaminant capture devices 23, inhales and hold his/her breath or continue to inhale to maintain a negative pressure. In some embodiment, after a course of events, such as those presently disclosed below, the output device of accessory 11 provides at least one alert to wearer 10.

Referring to FIG. 4, in some embodiments, negative pressure reusable respirator 13 includes at least one valve 9. In some examples, a first sensor 3 is disposed proximate at least one valve 9. In some examples, a second sensor 5 is disposed proximate at least one valve 9. In some embodiments, both first sensor 3 and second sensor 5 are disposed proximate at least one valve 9. First sensor 3 is configured to generate first sensor data indicative of a gas characteristic of negative pressure reusable respirator 13 and second sensor 5 is configured to generate second sensor data indicative of a position of at least one valve 9 of negative pressure reusable respirator 13.

Figure 5:
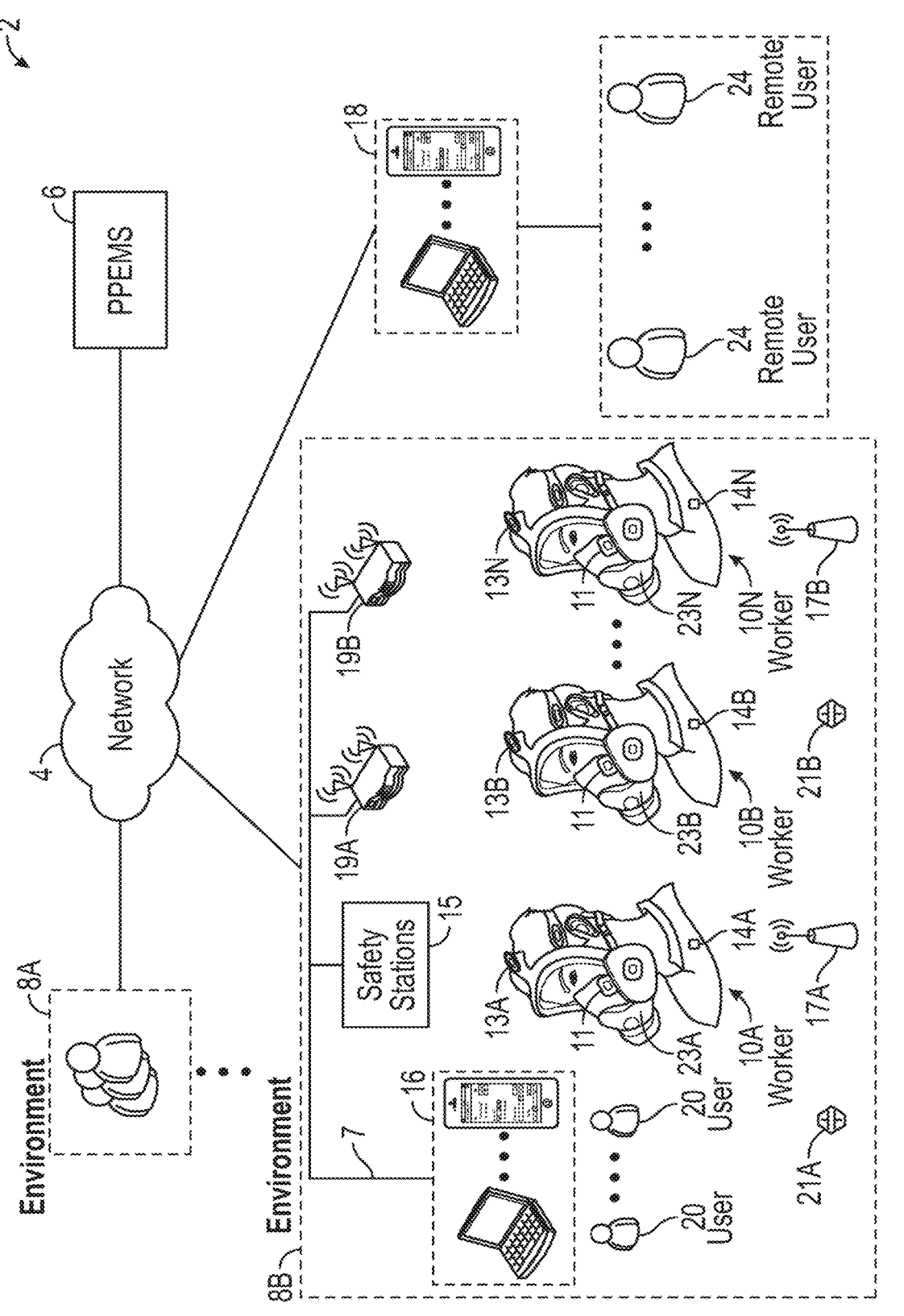
FIG. 5 is a block diagram illustrating an example system that includes a negative pressure reusable respirator and a personal protection equipment management system, in accordance with various techniques of this disclosure.

FIG. 5 is a block diagram illustrating an example system 2 that is a personal protective equipment management system (PPEMS) 6 for providing analytics and alerting of safety events for at least one negative pressure reusable respirator (i.e., 13A), and in some embodiments, for a plurality of negative pressure reusable respirators 13A-13N, according to techniques described in this disclosure. For example, each of negative pressure reusable respirators 13A-13N (collectively, negative pressure reusable respirators 13) include at least two sensors, where the first sensor is configured to generate first sensor data indicative of a gas characteristic of the respective negative pressure reusable respirators 13 and where the second sensor is configured to generate second sensor data indicative of a position of at least one valve of the respective negative pressure reusable respirators 13. In some embodiments, system 2 may also include at least one computing devices (e.g., PPEMS 6, bubs 14, accessories 11, among others), where the at least one computing device is configured to provide comparative data by comparing the first sensor data to the second sensor data. As used in this disclosure, the gas characteristic is selected from at least one of air pressure, gas composition, temperature, gas flow rate, and combinations thereof.

According to techniques of this disclosure, the at least one computing device, such as PPEMS 6, monitors usage to, at least in part, use the comparative data to determine at least one physical state of the negative pressure reusable respirator. In some embodiments, PPEMS 6 monitors gas characteristics in a sealed space formed by a face of the wearer and the negative pressure reusable respirator 13 and positions of the at least one valve in the negative pressure reusable respirator 13 to determine at least one physical state of the negative pressure reusable respirator 13. In some examples, the physical state may be selected from at least one of: presence of physical components of the negative pressure reusable respirator; performance metrics of physical components of the negative pressure reusable respirator; pressure drop of the negative pressure reusable respirator; pressure drop of the negative pressure reusable respirator at different air flow rates through the respirator; ambient temperature; temperature within the negative pressure reusable respirator; composition of ambient gases in the workplace; composition of gases within the negative pressure reusable respirator; and any combinations thereof. In some embodiments, the at least one computing device is further configured to determine a change in at least one physical state of the negative pressure reusable respirator 13.

According to techniques of this disclosure, the at least one computing device, such as PPEMS 6, monitors usage to, at least in part, use the comparative data to determine usage information related to the negative pressure reusable respirator 13. In some embodiments, PPEMS 6 monitors gas characteristics in a sealed space formed by a face of the wearer and the negative pressure reusable respirator 13 and positions of the at least one valve in the negative pressure reusable respirator 13 to determine usage information related to the negative pressure reusable respirator 13. In some examples, usage information is selected from at least one of: respiration through the at least one valve; occlusion of an inhalation path of the negative pressure reusable respirator 13; occlusion of an exhalation path of the negative pressure reusable respirator 13; occurrence of a wearer seal check; information related to a performance procedure of a wearer seal check; information related to quality of a seal formed by the face of the wearer and the negative pressure reusable respirator 13; change in the seal formed by the face of the wearer and the negative pressure reusable respirator 13; and any combination thereof. In some examples, respiration through the at least one valve includes steps of donning of the negative pressure reusable respirator 13 and doffing of the negative pressure reusable respirator 13. In some embodiments, the information related to a performance procedure of a wearer seal check is selected from at least one of: duration of time related to a wearer seal check; pressure related to a wearer seal check; occlusion of an inhalation path of the negative pressure reusable respirator 13; occlusion of an exhalation path of the negative pressure reusable respirator 13; and any combination thereof.

Figure 4A:
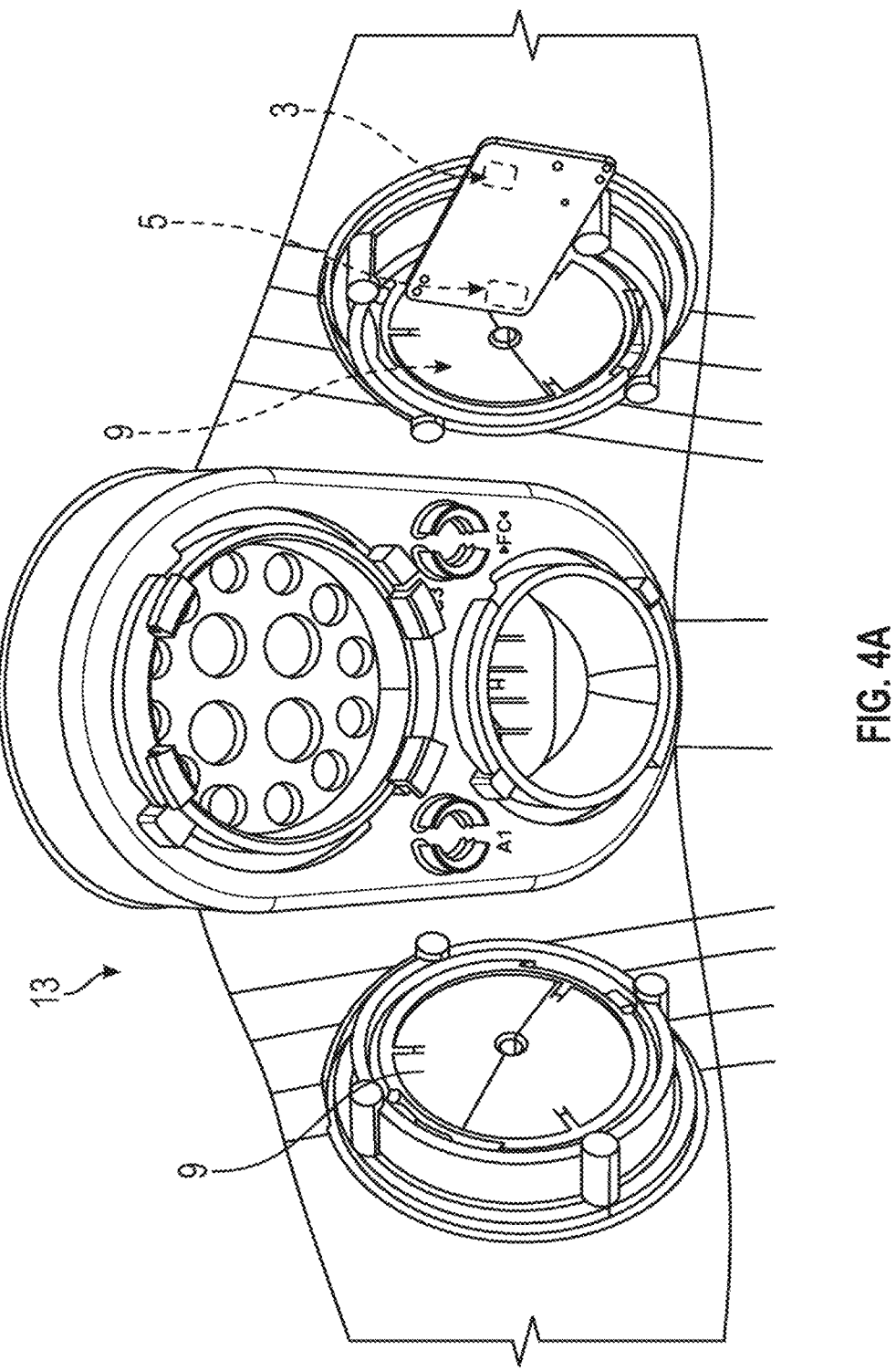
FIG. 4A is an interior perspective view of a portion of a negative pressure reusable respirator according to some embodiments of the present disclosure.
Figure 4B:
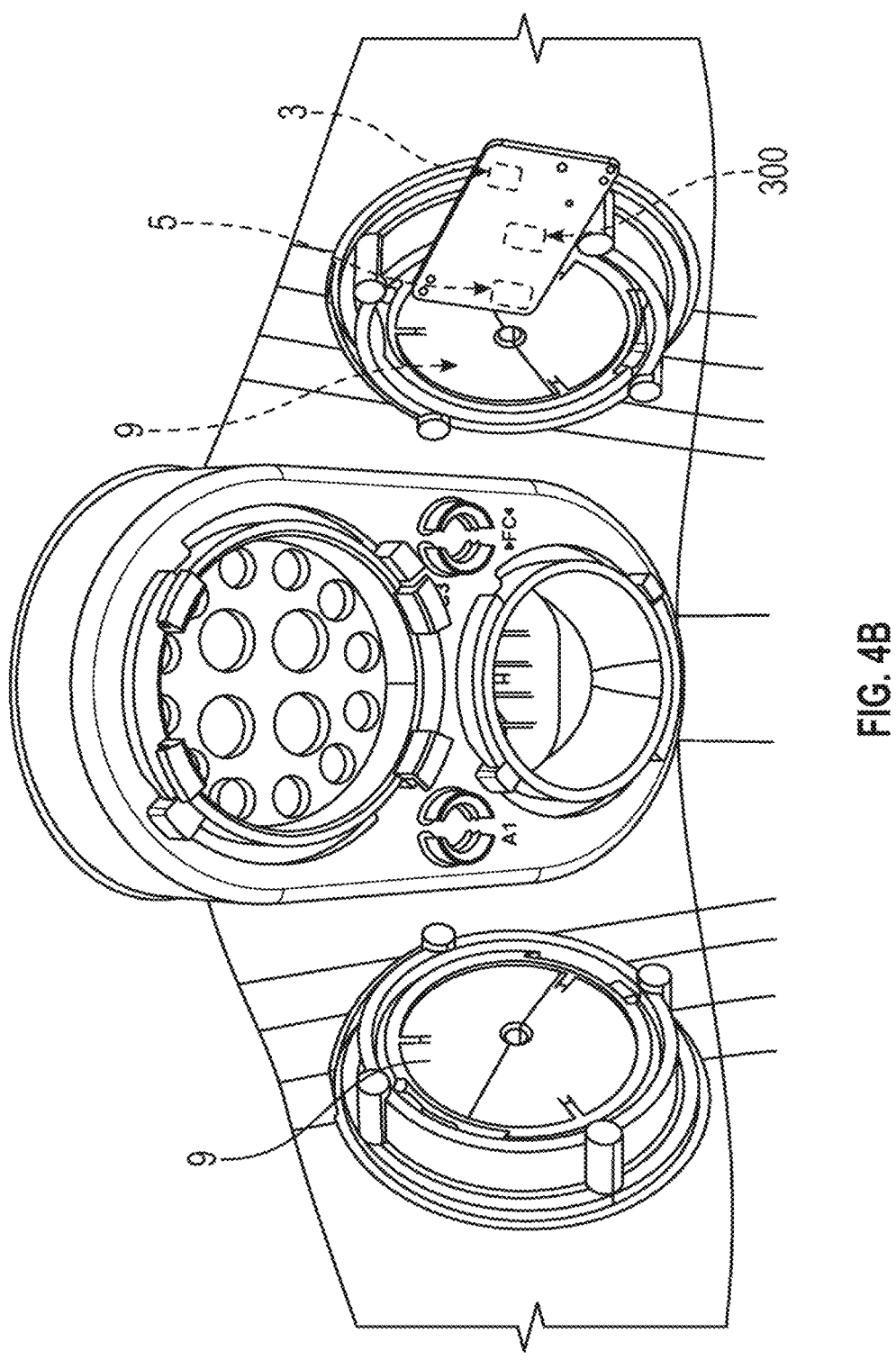
FIG. 4B is an interior perspective view of a portion of a negative pressure reusable respirator according to some embodiments of the present disclosure in which a computing device is physically coupled to a sensor.
Figure 4C:
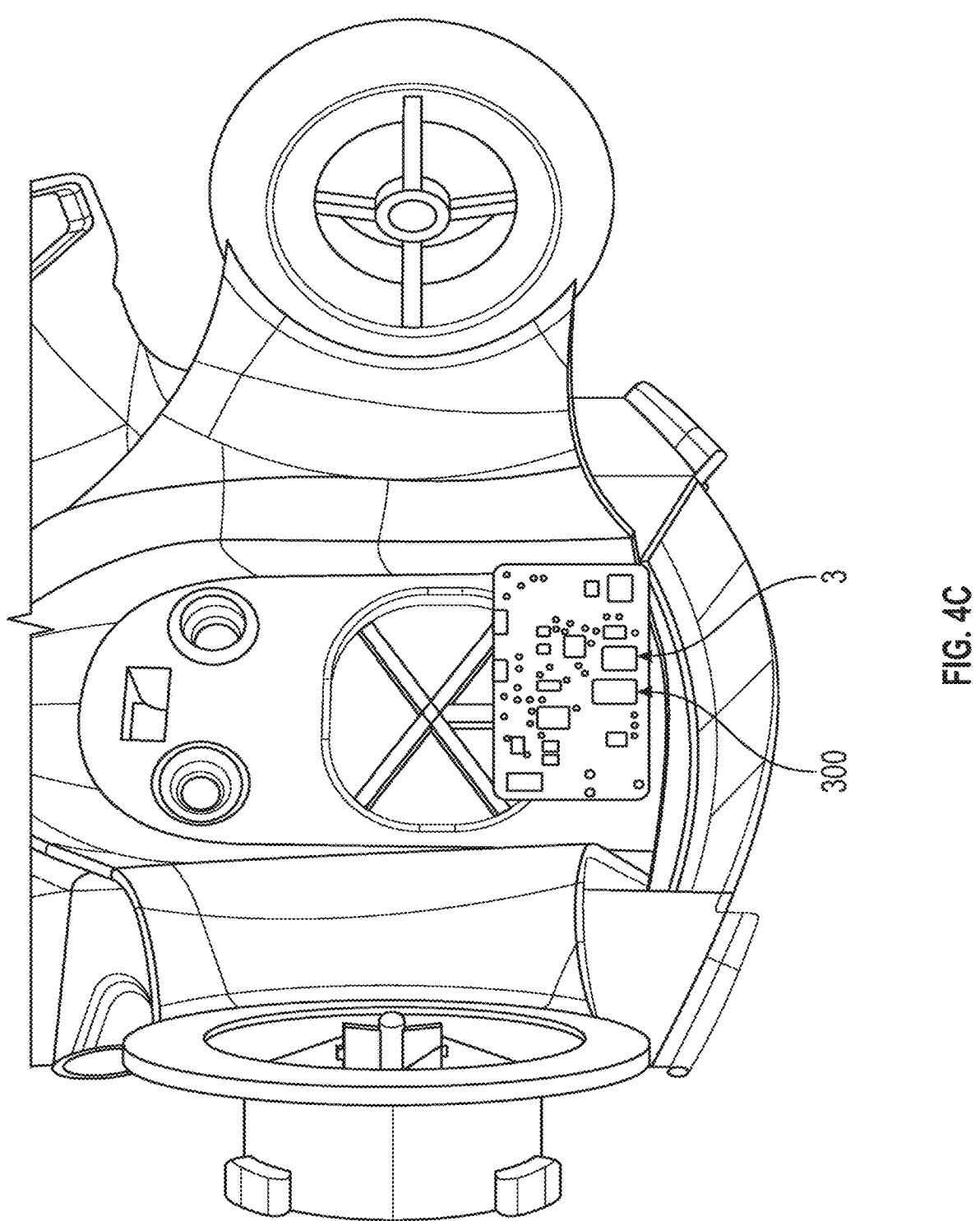
FIG. 4C is an interior perspective view of a portion of a half-face negative pressure reusable respirator according to some embodiments of the present disclosure.
Figure 4D:
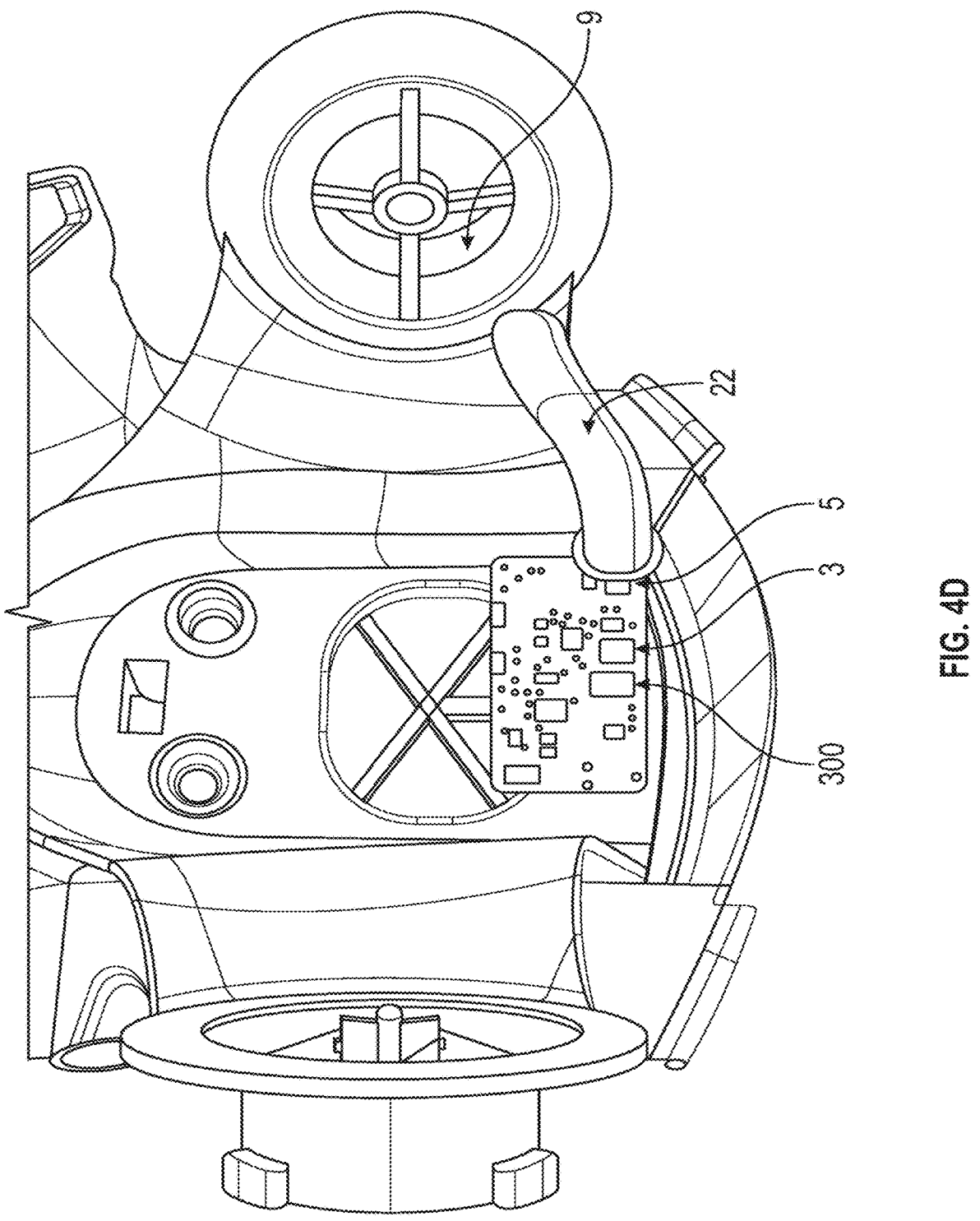
FIG. 4D is an interior perspective view of a portion of a negative pressure reusable respirator having an electromagnetic waveguide according to some embodiments of the present disclosure

The presently disclosed second sensor may include an electromagnetic radiation emitter and an electromagnetic radiation detector. In some embodiments, the electromagnetic radiation emitter may comprise a light emitting diode, a laser diode, an incandescent bulb, or other such device configured to generate electromagnetic radiation. In some embodiments, an electromagnetic radiation detection may comprise a photo-sensitive diode, a bolometer, a photosensitive diode array, a charge-coupled device, an As shown in FIG. 4D, in some embodiments, the second sensor further includes an electromagnetic waveguide 22 structure configured to transmit electromagnetic radiation from the electromagnetic radiation emitter to the at least one valve of the negative pressure reusable respirator 13, and from the at least one valve to the electromagnetic radiation detector. In some embodiments, the electromagnetic waveguide 22 structure may comprise a plurality of electromagnetic waveguides.

As shown in the example of FIG. 5, system 2 represents a computing environment in which computing device(s) within a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, use personal protective equipment, such as a negative pressure reusable respirator 13 while engaging in tasks or activities within the respective environment. Example environments 8 include construction sites, mining sites, manufacturing sites, among others, In this example, environment 8A is shown as generally as having workers 10, while environment 8B is shown in expanded form to provide a more detailed example. In the example of FIG. 5, a plurality of workers 10A-10N are shown as utilizing personal protective equipment (PPE), such as negative pressure reusable respirators 13. As used throughout this disclosure, negative pressure reusable respirators 13 include any reusable respirator in which the air pressure inside the facepiece is less than the ambient air pressure (e.g., the pressure of the air outside the respirator) during inhalation. Although respirators 13 in the example of FIG. 5 are illustrated as negative-pressure reusable respirators, the techniques described herein apply to other types of respirators, such as positive pressure reusable respirators, disposable respirators, or powered-air purifying respirators. As used throughout this disclosure, a positive pressure respirator includes any respirator in which the air pressure inside the facepiece is greater than the ambient air pressure. Negative pressure reusable respirators 13 include a facepiece (e.g., a full facepiece, or a half facepiece) configured to cover at least a worker's nose and mouth. For example, a half facepiece may cover a worker's nose and mouth and a full facepiece may cover a worker's eyes, nose, and mouth. Negative pressure reusable respirators 13 may fully or partially (e.g., 75%) cover a worker's head. Negative pressure reusable respirators 13 may include a head harness (e.g., an elastic strap) that secures negative pressure reusable respirators 13 to the back of the worker's head.

Again, as shown in examples depicted in FIGS. 1A, 1B, 2, and 4, physical components of the negative pressure reusable respirator 13 may include one or more valves 9, one or more contaminant capture devices 23, one more removable accessory 11, and any combinations thereof. In some examples, negative pressure reusable respirators 13 are configured to receive contaminant capture devices 23A-23N (collectively, contaminant capture devices 23). Contaminant capture devices 23 are configured to remove contaminants from air as air is drawn through the contaminant capture device (e.g., when a worker wearing a reusable respirator inhales). Contaminant capture devices 23 include particulate filters, chemical cartridges, or combination particulate filters/chemical cartridges. As used throughout this disclosure, particulate filters are configured to protect a worker from particulates (e.g., dust, mists, fumes, smoke, mold, bacteria, etc.). Particulate filters capture particulates through impaction, interception, and/or diffusion. As used throughout this disclosure, chemical cartridges are configured to protect a worker from gases or vapors. Chemical cartridges may include sorbent materials (e.g., activated carbon) that react with a gas or vapor to capture the gas or vapor and remove the gas or vapor from air breathed by a worker. For instance, chemical cartridges may capture organic vapors, acid gasses, ammonia, methylamine, formaldehyde, mercury vapor, chlorine gas, among others.

In some embodiments, contaminant capture devices 23 may be removable. In other words, a worker may remove a contaminant capture device from a negative pressure reusable respirator 13 (e.g., upon the contaminant capture device reaching the end of its expected lifespan) and install a different (e.g., unused, new) contaminant capture device to the respirator. In some examples, the particulate filters or chemical cartridges have a limited service life. In some examples, when a chemical cartridge is exhausted (e.g., captures a threshold amount of gas or vapors), gases or vapors may pass through the chemical cartridge to the worker (which is called "breakthrough"). In some examples, as particulate filters become saturated with a contaminant, the filter becomes harder to pull air through, thus making the worker inhale deeper to breathe.

Each of negative pressure reusable respirators 13 include, in some examples, embedded sensors or monitoring devices and processing electronics configured to capture data in real-time as a worker (e.g., wearer) engages in activities while utilizing (e.g., wearing) the respirator. Negative pressure reusable respirators 13 include a number of sensors for sensing operational characteristics of the respirators 13. For example, the first sensor useful in presently disclosed negative pressure reusable respirators 13 include an air pressure sensor configured to detect the air pressure in the cavity formed between the respirator and the worker's face, which detect the air pressure within the cavity as the worker 10 breathes (e.g., inhales and exhales). In other words, the air pressure sensors detect the air pressure within the sealed space (also referred to as a cavity, or respirator cavity) formed by a face of the wearer and the negative pressure reusable respirator 13.

In addition, in some embodiments, each of negative pressure reusable respirators 13 may include one or more computing devices 60, 300 that are configured to provide comparative data by comparing the first sensor data to the second sensor data to determine the physical state of the negative pressure reusable respirator. For example, the first sensor data providing air pressure within the sealed space is compared to the second sensor data providing valve position to determine the performance of physical components of the negative reusable respirator. In some embodiments, as shown in FIG. 8, computing device 300 is operably disposed within accessory 11, where accessory 11 is operably disposed within a sealed space formed by a face of the wearer and the negative pressure reusable respirator 13A.

In addition, in some embodiments, each of negative pressure reusable respirators 13 may include one or more computing devices 300 that are configured to provide comparative data by comparing the first sensor data to the second sensor data to determine usage information related to the negative pressure reusable respirator.

In addition, each of negative pressure reusable respirators 13 may include one or more output devices for outputting data that is indicative of operation of negative pressure reusable respirator 13 and/or generating and outputting communications to the respective worker 10. For example, negative pressure reusable respirators 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback). In some embodiments, such feedback is provided in the form of at least one alert selected from: an audible alert, a visual alert, a haptic alert, a text alert, or any combination thereof. In some embodiments, the output device is operably disposed on presently disclosed accessory 11.

In some examples, at least one computing device 16, 18, 60, 300 is configured to perform one or more actions by at least in part being configured to: output a notification to a second computing device; output an alert to a wearer of a negative pressure reusable respirators 13; output to another wearer in a proximal environment; or a combination thereof. In some examples, the alert is selected from at least one of an audible alert, a visual alert, a haptic alert, a text alert, or a combination thereof.

In some examples, at least one computing device 16, 18, 60, 300 is configured to output an alert in response to the comparative data. In some examples, at least one computing device 16, 18, 60, 300 is configured to output an alert in response to determining that respiration occurred through the at least one valve and a wearer seal check was not performed. In some examples, the output is selected from at least one of: a notification to the wearer to perform a seal check; a notification to another computing device that the wearer failed to perform a seal check; a notification to another wearer in a proximal environment; or a combination thereof. In some examples, if a notification to the wearer to perform a seal check was provided to the wearer, the output is alterable. For example, the at least one computing device 16, 18, 60, 300 may output alert notifications to the wearer to perform a seal check in the form of lights and vibrations to the wearer.

In some examples, at least one computing device 16, 18, 60, 300 is configured to output an alert to the wearer in response to determining that respiration occurred through that at least one valve and a wearer seal check was performed. In some examples, the output is selected from at least one of: a notification that the wearer is performing a seal check related to the quality of seal of the negative pressure reusable respirator on the wearer's face; a notification that the wearer performed a seal check related to the quality of seal of the negative pressure reusable respirator on the wearer's face that satisfied at least one threshold; a notification that the wearer performed a seal check related to the quality of seal of the negative pressure reusable respirator on the wearer's face that did not satisfy at least one threshold; or a combination thereof. In some examples, if notification that the wearer performed a seal check related to the quality of seal of the negative pressure reusable respirator on the wearer's face that satisfied at least one threshold is provided to the wearer, the alert is discontinued. In some examples, if notification that the wearer performed a seal check related to the quality of seal of the negative pressure reusable respirator on the wearer's face that did not satisfy at least one threshold is provided to the wearer, the alert is altered. In some embodiments, the alert is altered by altering at least one of intensity of the alert, frequency of the alert, tone of the alert, pattern of the alert, color of the alert, display of the alert, content of the alert, or a combination thereof. For example, the at least one computing device 16, 18, 60, 300 may output alert notifications to the wearer to perform a seal check in the form of lights and vibrations to the wearer. The at least one computing device 16, 18, 60, 300 may then alter the alert, or provide an additional alert that the wearer is performing a seal check related to the quality of seal of the negative pressure reusable respirator on the wearer's face. The at least one computing device 16, 18, 60, 300 may then alter the alert, or provide an additional alert, or discontinue the alert, or a combination thereof, that the wearer performed a seal check related to the quality of seal of the negative pressure reusable respirator on the wearer's face that satisfied at least one threshold. Alternatively, the at least one computing device 16, 18, 60, 300 may then alter the alert, or provide an additional alert, or discontinue the alert, or a combination thereof, that the wearer performed a seal check related to the quality of seal of the negative pressure reusable respirator on the wearer's face that did not satisfy at least one threshold. For example, the at least one computing device 16, 18, 60, 300 may alter the alert in response to the wearer performed a seal check related to the quality of seal of the negative pressure reusable respirator on the wearer's face that did not satisfy at least one threshold, and then revert to the alert to the wearer to perform a seal check.

Figure 6:
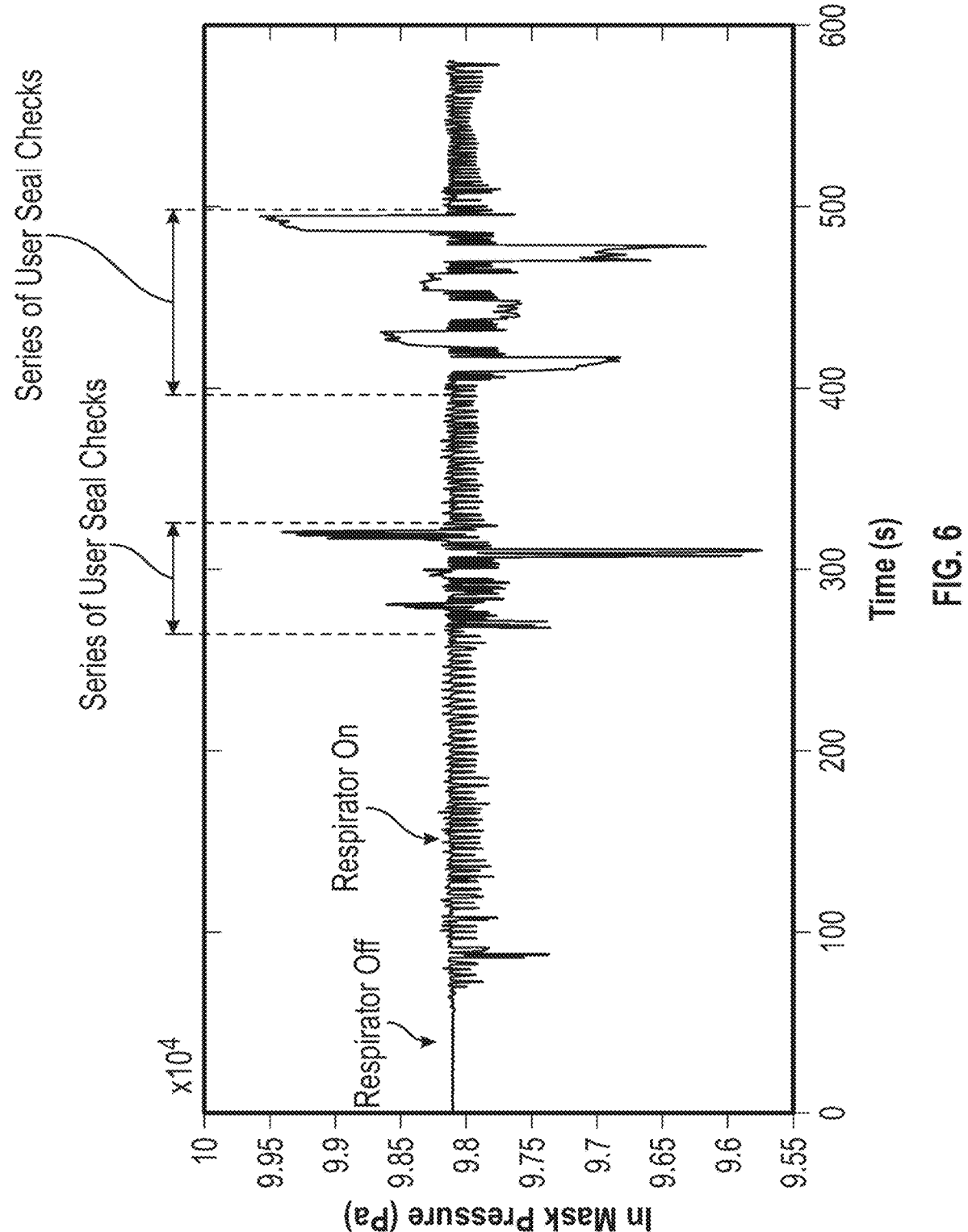
FIG. 6 shows first sensor data as air pressure data over time from inside an exemplary negative pressure reusable respirator according to the present disclosure when it is being worn, when it is not being worn, and during wearer seal checks.

In some examples, computing device 16, 18, 60, 300 may automatically determine that negative pressure reusable respirator 13 is being worn by a wearer 10. For example, computing device 16, 18, 60, 300 may receive first sensor data, such as air pressure data, indicative of the air pressure in the sealed space formed by a face of the wearer and the negative pressure reusable respirator 13 from a first sensor 3, wherein the air pressure data meets a set of predetermined thresholds. For example, FIG. 6 shows first sensor data as air pressure data over time from inside an exemplary negative pressure reusable respirator 13 according to present disclosure when it is being worn, when it is not being worn, and during wearer seal checks. For example, a computing device 16, 18, 60, 300 may determine that a negative pressure reusable respirator 300 transitioned from a state of not being worn by a wearer to being worn by a wearer when the pressure data over time meets a threshold number of peaks (increase in pressure) or valleys (decrease in pressure) that meet a threshold pressure change (positive or negative) in a threshold amount of time. For example, when the air pressure data measured from first sensor 3 indicates three differential pressure changes (pressure difference between the air pressure in the sealed space formed by a face of wearer 10 and negative pressure reusable respirator 13 and the ambient pressure) below −100 Pascals in less than thirty seconds, computing device 16, 18, 60, 300 may determine that negative pressure reusable respirator 13 transitioned from a state of not being worn by a wearer 10 to being worn by a wearer 10. This enables computing device 16, 18, 60, 300 to determine that respirator 13 is being worn by wearer 10 without any additional action from wearer 10 beyond donning respirator 13. As a beneficial result, wearer 10 does not have to be trained or remember to take an action to initiate computing device 16, 18, 60, 300. Devices that do not automatically determine donning and wear of respirator 13 may require a trained user action such as interacting directly with computing device 16, 18, 60, 300 or covering contaminant capture devices 23 and inhaling sharply to generate a specific sensor signal, or other such examples that require a trained user action, to initiate computing device 16, 18, 60, 300.

In some examples, after computing device 16, 18, 60, 300 determined that a negative pressure reusable respirator 13 is being worn by a wearer 10, computing device 16, 18, 60, 300 may perform one or more actions as indicated by one or more safety rules. In some examples, computing device 16, 18, 60, 300 may perform one or more actions immediately upon determining that a negative pressure reusable respirator 13 is being worn by wearer 10, at a time after determining that a negative pressure reusable respirator 13 is being worn by a wearer 10, or at a plurality of times.

In some examples, safety rules may be retrieved from a memory module physically coupled to computing device 16, 18, 60, 300. In some examples, the safety rules may be retrieved from a device physically separate from computing device 16, 18, 60, 300, such as via wireless communication to another device. In some examples, the safety rules may be related to the performance of a wearer seal check by wearer 10. For example, after computing device 16, 18, 60, 300 detected that the wearer 10 donned respirator 13, computing device 16, 18, 60, 300 may initiate a pattern of alerts to wearer 10 until a wearer seal check is performed. In one example, the alerts may take the form of a pattern of vibrations and/or lights and/or audible signals (such as text content, lights, and the like) to wearer 10. Computing device 16, 18, 60, 300 may then determine that a wearer seal check is being performed based at least in part on data from the first sensor indicative of a gas characteristic or a combination of the first sensor data and second sensor data indicative of a position of a valve. In some examples, computing device 16, 18, 60, 300 may alter the alert output while the wearer seal check is being performed, for example by temporarily turning off the alert while the wearer seal check is being performed. In some example, computing device 16, 18, 60, 300 may then generate an alert based on whether or not the wearer seal check satisfied a threshold or a combination of thresholds. In one example, computing device 16, 18, 60, 300 may generate an alert indicating an unsatisfactory seal check if the air pressure or combined air pressure and valve position data cross a threshold after the wearer seal check has started. For example, if the absolute differential air pressure (difference between the ambient air pressure and the air pressure in the sealed space formed by a face of the wearer and the negative pressure reusable respirator, either positive or negative) falls below a threshold at any time before a satisfactory wearer seal check is determined, the wearer seal check may be determined to be unsatisfactory. In some examples, if an unsatisfactory wearer seal check is determined, computing device 16, 18, 60, 300 may generate an alert comprising a pattern of vibrations and/or lights and/or audible and/or text content signals to the wearer, such as a series of rapid red lights and vibrations. Following this unsatisfactory wearer seal check alert, computing device 16, 18, 60, 300 may revert the alerts back to the same alerts that were generated after computing device 16, 18, 60, 300 determined that respirator 13 entered a state of being worn by a wearer 10.

In another instance, if the wearer seal check is determined to be satisfactory by meeting one or more thresholds, computing device 16, 18, 60, 300 may generate a different pattern of alerts indicating a satisfactory seal check has been performed. For example, the alerts may take the form a green light and single long vibration to indicate a satisfactory wearer seal check. In some examples, if a satisfactory wearer seal check is performed, the first set of alerts generated after determining that the respirator is being worn may remain turned off.

In some examples, a satisfactory wearer seal check may require wearer 10 to continually exert either positive or negative pressure into respirator 13 to achieve the required threshold. In these examples, a satisfactory wearer seal check may be determined if the air pressure or combined air pressure and valve position data cross a threshold after the wearer seal check has started. For example, if the absolute differential air pressure (difference between the ambient air pressure and the air pressure in the sealed space formed by a face of the wearer and the negative pressure reusable respirator, either positive or negative pressure) is maintained above or below a threshold for a predetermined period, such as a period of time, the wearer seal checked may be determined to be satisfactory. In another example, the period may not be predetermined, and may instead be a dynamic period depending on the magnitude of the air pressure. For example, the threshold required to achieve a satisfactory wearer seal check may be a time integration of the air pressure during a wearer seal check, such that when a cumulative combination of time and pressure exceeds a threshold, the wearer seal check is determined to be satisfactory.

In some examples, a satisfactory wearer seal check may require wearer 10 to either inhale or exhale into the respirator and then hold their breath. In these examples, the threshold required to achieve a satisfactory wearer seal check may be based on a change in air pressure or change in the combination of air pressure and valve position data over time. For example, a rapid decay in the absolute different air pressure, after inhaling or exhaling, towards the ambient air pressure may indicate an unsatisfactory seal, whereas a slow decay may indicate a satisfactory seal. In some examples, computing device 16, 18, 60, 300 may determine, based at least in part on changes in air pressure data over time during the wearer seal check, whether wearer 10 is holding their breath, or continuing to exert either positive or negative pressure into the respirator, Computing device 16, 18, 60, 300 may then use a different set of thresholds to determine whether or not a satisfactory wearer seal check is achieved, based on the determination of how the wearer is performing the wearer seal check.

In some examples, computing device 16, 18, 60, 300 may use the same set of thresholds that was used to determine that a negative pressure reusable respirator 13 has transitioned from a state of not being worn by a wearer 10 to a state of being worn by a wearer 10 to additionally determine that a negative pressure reusable respirator 13 continues to be worn by a wearer 10, or transitions from a state of being worn by a wearer 10 to not being worn by a wearer 10. In another example, computing device 16, 18, 60, 300 may use a different set of thresholds to determine that a negative pressure reusable respirator 13 continues to be worn by a wearer 10, or transitions from a state of being worn by a wearer 10 to not being worn by a wearer 10. For example, if the air pressure, as determined by first sensor 3, has a variability, such as a difference between minimum and maximum values, below a threshold during a threshold period of time, computing device 16, 18, 60, 300 may determine that the negative pressure reusable respirator 13 is no longer being worn by a wearer 10. In some examples, the thresholds may be part of predetermined safety rules.

In other examples, the thresholds may by dynamically determined based on models based at least in part on the use of respirator 13 and/or wearer information. In some examples, if computing device 16, 18, 60, 300 determines that respirator 13 is no longer being worn by a wearer 10, and then later determines that respirator 13 is once again being worn by a wearer 10, computing device 16, 18, 60, 300 may restart the previously described alert sequences related to detecting that respirator 13 is being worn by wearer 10 and a satisfactory wearer seal check has not been performed. In some examples, the alert sequences may only be started again respirator 13 was in a state of not being worn (i.e. was removed) for a time greater than threshold period. Said another way, the one or more safety rules may comprise a condition that a respirator seal check was performed by wearer 10 before a period of negative pressure reusable respirator 13 being in a state of not being worn by a wearer 10 that is less than a predetermined period. In some instances, the set of thresholds used to determine that respirator 13 is no longer being worn by a wearer 10 may also be used, with the same or different threshold values, to determine that negative pressure reusable respirator 13 does not provide an adequate seal to the face of the wearer 10. In some examples, the threshold values may be relative threshold values. For example, if the air pressure variability over time as measured by the first sensor rapidly decreases relative to the variability at a previous time, computing device 16, 18, 60, 300 may determine a loss of adequate respirator seal. In another example, computing device 16, 18, 60, 300 may use a combination of sensor data, or a combination of sensor data that changes over time, to determine a loss in adequate respirator seal. For example, computing device 16, 18, 60, 300 may determine a loss in respirator seal at least in part based on a combination of air pressure data from a first sensor 3 and valve position data from a second sensor 5 that change over time. Computing device 16, 18, 60, 300 may then use similar alert mechanisms, such as a pattern of vibrations and/or lights and/or audible signals and/or text content signals to wearer 10 to alert wearer 10 to the loss of respirator seal.

In another example, the combination of sensor data may be a combination of data from a single sensor over different periods of time. For example, computing device 16, 18, 60, 300 may determine periods of inhalation and periods of exhalation based on data from a first sensor 3 indicative of a gas characteristic in a sealed space formed by a face of wearer 10 and negative pressure reusable respirator 13, and/or data from a second sensor 5 indicative of a valve position. Computing device 16, 18, 60, 300 may then compare the data during periods of inhalation to the data during periods of exhalation and determine changes in the respirator seal based on the comparative data. For example, the magnitude of inhalation pressure relative to ambient pressure compared to the magnitude of exhalation pressure relative to ambient pressure may change due to changes in the respirator seal.

In another example, computing device 16, 18, 60, 300 may use a combination of comparative data from a single sensor during different periods of time as well as comparative data between different sensors to determine changes in the respirator seal. In some examples, the ambient pressure may be determined at least in part based on data from first sensor 3 indicative of a gas characteristic in a sealed space formed by a face of wearer 10 and negative pressure reusable respirator 13. In some examples, the ambient pressure may be determined by an additional sensor located external to the sealed space of respirator 13.

In further examples, the previously described examples may use first sensor data that is different than air pressure, such as a data indicative of a different gas characteristic of the sealed space formed by a face of the wearer and the negative pressure reusable respirator. For example, temperature, humidity, gas composition, gas flow rates, and others may be used to create similar thresholds as those described for air pressure data. In other examples, the alerts generated may be generated to devices or persons other than, or in addition to, the wearer, such as into a memory storage device, or to a separate computing device. In some examples, any of the previously described thresholds, safety rules and alert properties may be configurable.

In some embodiments, accessories 11 operably disposed in each of negative pressure reusable respirators 13 are configured to communicate data, such as sensed motions, events and conditions, via wireless communications, such as via 802.11 WiFi® protocols, Bluetooth® protocol or the like. Accessories 11 operably disposed in negative pressure reusable respirators 13 may, for example, communicate directly with a wireless access point 19. As another example, each worker 10 may be equipped with a respective one of wearable communication hubs 14A-14M that enable and facilitate communication between accessories 11 operably disposed in negative pressure reusable respirators 13 and PPEMS 6. For example, accessories 11 operably disposed in negative pressure reusable respirators 13 as well as other PPEs (such as fall protection equipment, hearing protection, hardhats, or other equipment) for the respective worker 10 may communicate with a respective communication hub 14 via Bluetooth or other short-range protocol, and the communication hubs may communicate with PPEMs 6 via wireless communications processed by wireless access points 19. Although shown as wearable devices, hubs 14 may be implemented as stand-alone devices deployed within environment 8B. In some examples, hubs 14 may be articles of PPE.

In some embodiments, each of environments 8 may include computing facilities (e.g., a local area network) by which sensing stations 21, beacons 17, and/or accessories 11 operably disposed in negative pressure reusable respirators 13 are able to communicate with PPEMS 6. For examples, environments 8 may be configured with wireless technology, such as 802.11 wireless networks, 802.15 ZigBee networks, and the like. In the example of FIG. 5, environment 8B includes a local network 7 that provides a packet-based transport medium for communicating with PPEMS 6 via network 4. Environment 8B may include wireless access point 19 to provide support for wireless communications. In some examples, environment 8B may include a plurality of wireless access points 19 that may be geographically distributed throughout the environment to provide support for wireless communications throughout the environment.

In some examples, each worker 10 may be equipped with a respective one of wearable communication hubs 14A-14N that enable and facilitate wireless communication between PPEMS 6 and sensing stations 21, beacons 17, and/or negative pressure reusable respirators 13. For example, sensing stations 21, beacons 17, and/or negative pressure reusable respirators 13 may communicate with a respective communication hub 14 via wireless communication (e.g., Bluetooth® or other short-range protocol), and the communication hubs may communicate with PPEMS 6 via wireless communications processed by wireless access point 19. Although shown as wearable devices, hubs 14 may be implemented as stand-alone devices deployed within environment 8B.

In general, each of hubs 14 is programmable via PPEMS 6 so that local alert rules may be installed and executed without requiring a connection to the cloud. As such, each of hubs 14 provides a relay of streams of data from sensing stations 21, beacons 17, and/or negative pressure reusable respirators 13, and provides a local computing environment for localized alerting based on streams of events in the event communication with PPEMS 6 is lost.

As shown in the example of FIG. 5, an environment, such as environment 8B, may also contain one or more wireless-enabled beacons, such as beacons 17A-17B, that provide accurate location data within the work environment. For example, beacons 17A-17B may be GPS-enabled such that a controller within the respective beacon may be able to precisely determine the position of the respective beacon, Based on wireless communications with one or more of beacons 17, a given accessory 11 operably disposed in negative pressure reusable respirator 13, or communication hub 14 worn by a worker 10 is configured to determine the location of the worker within environment 8B. In this way, event data reported to PPEMS 6 may be stamped with positional data to aid analysis, reporting and analytics performed by PPEMS 6, In addition, in some embodiments, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional data when reporting environmental data to PPEMS 6. As such, PPEMS 6 may be configured to correlate the sensed environmental conditions with the particular regions and, therefore, may utilize the captured environmental data when processing event data received from negative pressure reusable respirators 13, or sensing stations 21. For example, PPEMS 6 may utilize the environmental data to aid generating alerts or other instructions for negative pressure reusable respirators 13 and for performing predictive analytics, such as determining any correlations between certain environmental conditions (e.g., temperature, humidity, visibility) with abnormal worker behavior or increased safety events. As such, PPEMS 6 may utilize current environmental conditions to aid prediction and avoidance of imminent safety events. Example environmental conditions that may be sensed by sensing stations 21 include but are not limited to temperature, humidity, presence of gas, pressure, visibility, wind and the like. Safety events may refer to heat related illness or injury, cardiac related illness or injury, respiratory related illness or injury, or eye or hearing related injury or illness.

In example implementations, an environment, such as environment 8B, may also include one or more safety stations 15 distributed throughout the environment. Safety stations 15 may allow one of workers 10 to check out negative pressure reusable respirators 13 and/or other safety equipment, verify that safety equipment is appropriate for a particular one of environments 8, and/or exchange data. Safety stations 15 may enable workers 10 to send and receive data from sensing stations 21, and/or beacons 17. For example, safety stations 15 may transmit alert rules, software updates, or firmware updates to negative pressure reusable respirators 13 or other equipment, such as sensing stations 21, and/or beacons 17. Safety stations 15 may also receive data cached on negative pressure reusable respirators 13, hubs 14, sensing stations 21, beacons 17, and/or other safety equipment. That is, while equipment such as sensing stations 21, beacons 17, negative pressure reusable respirators 13, and/or data hubs 14 may typically transmit data via network 4 in real time or near real time, such equipment may not have connectivity to network 4 in some instances, situations, or conditions. In such cases, sensing stations 21, beacons 17, negative pressure reusable respirators 13, and/or data hubs 14 may store data locally and transmit the data to safety stations 15 upon regaining connectivity to network 4. Safety stations 15 may then obtain the data from sensing stations 21, beacons 17, negative pressure reusable respirators 13, and/or data hubs 14.

In addition, each of environments 8 may include computing facilities that provide an operating environment for end-worker computing devices 16 for interacting with PPEMS 6 via network 4. For example, each of environments 8 typically includes one or more safety managers responsible for overseeing safety compliance within the environment. In general, each worker 20 interacts with computing devices 16 to access PPEMS 6. Each of environments 8 may include systems. Similarly, remote workers may use computing devices 18 to interact with PPEMS 6 via network 4. For purposes of example, the end-worker computing devices 16 may be laptops, desktop computers, mobile devices such as tablets or so-called smart phones and the like. In some examples, the system 2 includes at least one computing device having a first computing device and a second computing device 16, where the first computing device is configured to provide the comparative data from the first and second sensors, and where the second computing device is configured to perform one or more actions by outputting an alert, wherein the alert comprises at least one of an audible alert, a visual alert, a haptic alert, a text alert, or a combination thereof. In some examples, the first computing device may be integrated in the personal protective equipment donned by the worker, such as for example computing device 300 operably disposed in accessory 11, which can be operably disposed in the negative pressure reusable respirator. In some examples, the first computing devise 18 may be a computing device 18 used by a worker in the work environment or remote from the work environment such that the worker can interact with the system 2. In some embodiments, the first computing device 18 is a combination of these examples.

Workers 20, 24 interact with PPEMS 6 to control and actively manage many aspects of safely equipment utilized by workers 10, such as accessing and viewing usage records, analytics and reporting. For example, workers 20, 24 may review data acquired and stored by PPEMS 6, where the data may include data specifying whether respiration occurred through at least on valve, whether the respirator was donned, whether an initial seal check of the respirator was performed by the worker, starting and ending times over a time duration (e.g., a day, a week, etc.), data collected during particular events, such as pulling a respirator away from the worker's face (e.g., such that the cavity formed by the worker's face and the respirator is not scaled, which may expose the worker to breathing hazards, without necessarily removing the respirator from the worker 10), removal of a negative pressure reusable respirator 13 from a worker 10, changes to operating parameters of a negative pressure reusable respirator 13, status changes to components of negative pressure reusable respirators 13 (e.g., a low battery event), motion of workers 10, detected impacts to negative pressure reusable respirators 13 or hubs 14, sensed data acquired from the worker, environment data, and the like. In addition, workers 20, 24 may interact with PPEMS 6 to perform asset tracking and to schedule maintenance events for individual pieces of safety equipment, e.g., negative pressure reusable respirators 13, to ensure compliance with any procedures or regulations. PPEMS 6 may allow workers 20, 24 to create and complete digital checklists with respect to the maintenance procedures and to synchronize any results of the procedures from computing devices 16, 18 to PPEMS 6. In some examples, computing device 16 is located within physical environment 8 where workers 10 and users 20 are located. In some examples, computing device 16 is integral to negative pressure reusable respirator 13 worn by worker 10. In some examples, computing device 18 is located remote from physical environment 8 where workers 10 and users 20 are located.

In some embodiments, PPEMS 6 may provide an integrated suite of personal safety protection equipment management tools and implements various techniques of this disclosure. That is, in some examples, PPEMS 6 provides an integrated, end-to-end system for managing personal protection equipment, e.g., respirators, used by workers 10 within one or more physical environments 8. These exemplary techniques may be realized within various parts of system 2.

PPEMS 6 may integrate an event processing platform configured to process thousand or even millions of concurrent streams of events from digitally enabled devices, such as sensing stations 21, beacons 17, negative pressure reusable respirators 13, sensors on the negative pressure reusable respirators 13, and/or data hubs 14. An underlying analytics engine of PPEMS 6 may apply models to the inbound streams to compute assertions, such as identified anomalies or predicted occurrences of safety events based on conditions or behavior patterns of workers 10.

Further, PPEMS 6 may provide real-time alerting and reporting to notify workers 10 and/or workers 20, 24 of any predicted events, anomalies, trends, and the like. The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protective equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Workers 20, 24 may access PPEMS 6 to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18, 60, 300 used by workers 20, 24, such as desktop computers, laptop computers, mobile devices such as smartphones and tablets, accessories operably disposed on negative pressure reusable respirators, or the like.

In some examples, PPEMS 6 may provide a database query engine for directly querying PPEMS 6 to view acquired safety data, compliance data and any results of the analytic engine, e.g., by the way of dashboards, alert notifications, reports and the like. That is, workers 20, 24 or software executing on computing devices 16, 18, 60, 300 may submit queries to PPEMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 8 for which unusually anomalous (e.g., high) safety events have been or are predicted to occur, identifications of any of environments 8 exhibiting anomalous occurrences of safety events relative to other environments, and the like.

As illustrated in detail below, PPEMS 6 may simplify workflows for individuals charged with monitoring and ensure safety compliance for an entity or environment. That is, PPEMS 6 may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, workers 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment, such as one of negative pressure reusable respirators 13. In this manner, PPEMS 6 may identify individual negative pressure reusable respirators 13 or workers 10 for which the metrics do not meet the benchmarks and prompt the workers to intervene and/or perform procedures to improve the metrics relative to the benchmarks, thereby ensuring compliance and actively managing safety for workers 10.

In accordance with techniques of this disclosure, PPEMS 6 determines whether a contaminant capture device 23 of a negative pressure reusable respirator 13 is due for replacement. In some examples, PPEMS 6 determines whether a contaminant capture device (e.g., contaminant capture device 23A) is due to be replaced based at least in part sensor data generated by two or more sensors in environment 8B, such as first sensor data generated by first sensor on the negative pressure reusable respirator 13 and second sensor data generated by second sensor negative pressure reusable respirator 13. In some examples, PPEMS 6 determines whether negative pressure reusable respirator 13 was donned by a wearer as well as determining whether a contaminant capture device (e.g., contaminant capture device 23A) is due to be replaced, where such determinations are based at least in part sensor data generated by two or more sensors in environment 8B, such as first sensor data generated by first sensor operably disposed on the negative pressure reusable respirator 13 and second sensor data generated by second sensor operably disposed on the negative pressure reusable respirator 13.

In some examples, contaminant capture device 23A includes a particulate filter and negative pressure reusable respirator 13A includes a pressure sensor configured to detect the air pressure of air within a cavity formed and sealed by the face of worker 10A and negative pressure reusable respirator 13A. In such examples, PPEMS 6 determines whether contaminant capture device 23A should be replaced based on the air pressure within the cavity sealed by the face of worker 10A and negative pressure reusable respirator 13A. For example, the air pressure sensor detects a decrease in the air pressure within the cavity as worker 10A inhales. PPEMS 6 may determine a pressure differential as worker 10A inhales over time. In other words, PPEMS 6 may determine a baseline pressure within the sealed cavity when the worker inhales at a first time (e.g., when the filter is new), a current pressure within the sealed cavity when the worker inhales at a second, later time, and determine the pressure differential as a difference between the baseline pressure and the current pressure.

In some embodiments, PPEMS may additionally determine a baseline position of at least one valve when the worker inhales at a first time (e.g. when the filter is new), a current valve position when the worker inhales at a second, later time, and compare the air pressure data and valve position data at the first time and compare the air pressure data and valve position data at the second time to determine whether the contaminant capture device 23A should be replaced. For example, as the contaminant capture device 23A increases air flow resistance due to filter loading, the air pressure differential required to induce a given valve position may increase, indicating that the contaminant capture device 23A should be replaced.

In some embodiments, PPEMS may additionally determine a baseline position of at least one valve and a baseline pressure when the worker inhales at a first time (e.g. when the filter is new), a current valve position and a current pressure when the worker inhales at a second, later time, and compare the air pressure data and valve position data at the first time and compare the air pressure data and valve position data at the second time to determine whether the contaminant capture device 23A should be replaced. For example, as the contaminant capture device 23A increases air flow resistance due to filter loading, the air pressure differential required to induce a given valve position may increase, indicating that the contaminant capture device 23A should be replaced.

PPEMS 6 may compare the pressure differential to a threshold decrease in air pressure (also referred to as a threshold pressure differential). In some examples, PPEMS 6 may determine that contaminant capture device 23A is due for replacement in response to determining that the pressure differential satisfies (e.g., is greater than or equal to) a threshold pressure differential. PPEMS 6 may determine that contaminant capture device 23A is not due for replacement in response to determining that the pressure differential does not satisfy a threshold pressure differential.

In some examples, contaminant capture device 23A includes a chemical cartridge and environment 8B includes a sensing station 21A configured to detect the concentration of one or more contaminants (e.g., gases or vapors) in work environment 8B. In such examples, PPEMS 6 may determine whether contaminant capture device 23A should be replaced based at least in part on the concentration of the contaminant and an amount of time worker 10A is located with environment 8B. For example, PPEMS 6 may determine a threshold protection time (e.g., an amount of time that contaminant capture device 23A protects worker 10A) based on device data for the contaminant capture device 23A and the contamination concentration. The device data may indicate a type of contaminant capture device 23A, an amount of contaminants the contaminant capture device 23A can capture (also referred to as a contaminant capture capacity), among others. For instance, PPEMS 6 may determine the threshold protection time based on the contaminant capture capacity of contaminant capture device 23A and the contaminant concentration within work environment 8B. In such instances, PPEMS 6 determines whether the actual usage time (e.g., time within environment 8B) of contaminant capture device 23A satisfies the threshold protection time. In some examples, PPEMS 6 determines that contaminant capture device 23A is not due for replacement in response to determining that the actual usage time of contaminant capture device 23A does not satisfy (e.g., is less than) the threshold protection time. As another example, PPEMS 6 determines that contaminant capture device 23A is due for replacement in response to determining that the actual usage time of contaminant capture device 23A satisfies (e.g., is greater than or equal to) the threshold protection time.

Responsive to determining that contaminant capture device 23A is due for replacement, PPEMS 6 performs one or more actions. In one example, PPEMS 6 outputs a notification to computing device associated with worker 10A (e.g., hub 14A), computing devices 16, 18, 60, 300 associated with workers 20, 24, to safety stations 15, or other computing devices. In some examples, the notification includes data indicating the negative pressure reusable respirator 13A or component of the negative pressure reusable respirator 13A that is due for replacement, the worker associated with the respirator, a location of the worker, among other data. In some instances, a computing device (e.g., hub 14A) receives the notification and output an alert, for instance, by outputting an audible, visual, or tactile alert.

In some examples, PPEMS 6 determines whether the negative pressure reusable respirator provides a seal around the worker's face. PPEMS 6 may determine whether the negative pressure reusable respirator 13A provides a seal based on sensor data from an infrared sensor of negative pressure reusable respirator 13A. For instance, the infrared sensor may generate data indicative of a distance between a negative pressure reusable respirator 13A (e.g., a face piece of negative pressure reusable respirator 13A) and the face of worker 10A. In some examples, PPEMS 6 determines whether negative pressure reusable respirator 13A seals a cavity between the worker's face and the respirator based on the distance between the negative pressure reusable respirator and the face of the worker. For example, PPEMS 6 may compare the distance to a threshold distance. In some instances, PPEMS 6 determines that negative pressure reusable respirator 13A does not provide a seal in response to determining that the distance satisfies (e.g., is greater than) a threshold distance. For instance, PPEMS 6 may determine that worker 10A is not clean shaven or pulled respirator 13A away from his or her face in response to determining that the distance satisfies (e.g., is greater than) a threshold distance. In such instances, PPEMS 6 may output a notification to another computing device (e.g., computing devices 18) indicating worker 10A is not clean shaven or pulled respirator 13A away from his or her face. In some instances, PPEMS 6 causes a computing device associated with worker 10A (e.g., hub 14A) to output an alert (e.g., visual, audible, haptic) indicating negative pressure reusable respirator 13A does not provide a seal around the worker's face. In some examples, the alert indicates worker 10A is not clean shaven or pulled respirator 13A away from his or her face. In this way, PPEMS 6 may provide real-time (or near real-time) monitoring of the negative pressure reusable respirator, which may increase worker safety by alerting workers 10 when the respective negative pressure reusable respirators 13 do not form a seal with the face of the respective workers 10 and thus potentially expose the respective worker 10 to hazards within the air present in the work environment (e.g., within air exterior to the respirator).

In some examples, each contaminant capture device 23 includes a communication unit that is configured to transmit information indicative of the respective contaminant capture device 23 to a computing system. For example, the communication device may include an RFID tag configured to output identification information (e.g., a unique identifier, a type of contaminant capture device, etc.) for the respective contaminant capture device 23. In some instances, PPEMS 6 determines whether contaminant capture device 23A is configured to protect worker 10A from hazards within the work environment 8B based on the identification information. For instance, PPEMS 6 may determine the types of contaminants that contaminant capture device 23A is configured to protect against based on a type of the contaminant capture device 23A and compare such types of contaminants to types of contaminants within the work environment 8B. In some examples, the PPEMS 6 alerts worker 10A when the contaminant capture device 23A is not configured to protect workers from contaminants within the work environment 8B, which may enable a worker to utilize the correct contaminant capture device for the hazards within the environment, thereby potentially increasing worker safety.

While described with reference to PPEMS 6, the functionality described in this disclosure may be performed by other computing devices, such as one or more hubs 14 or computing devices 16, 18, 60, 300 of one or more negative pressure reusable respirators 13. For example, one or more computing devices 16, 18, 60, 300 may determine whether a contaminant capture device 23 of a negative pressure reusable respirator 13 is due for replacement. As another example, computing devices 16, 18, 60, 300 may determine whether negative pressure reusable respirator 13A provides a seal between the face of worker 10A and negative pressure reusable respirator 13A. In yet another example, computing devices 16, 18, 60, 300 determines whether contaminant capture device 23A is configured to protect worker 10A from contaminants within the work environment 8B. In some examples, multiple computing devices (e.g., computing devices 16, 18, 60, 300) may collectively perform the functionality described in this disclosure. For example, PPEMS 6 may determine a threshold protection time associated with a contaminant capture device (e.g., a chemical cartridge) and one or more computing devices 16, 18, 60, 300 may determine whether the actual usage time for the contaminant capture device satisfies the threshold protection time.

In this way, techniques of this disclosure may enable a computing system to more accurately or timely determine whether a contaminant capture device 23 is due for replacement. The computing system may notify (e.g., in real-time) workers when a contaminant capture device is due for replacement, which may enable a worker to replace the contaminant capture device. Replacing the contaminant capture device in a more timely manner may increase worker safety. For example, replacing a contaminant capture device (e.g., a particulate filter and/or chemical cartridge) of a respirator in a more timely manner may protect the worker by preventing gases from breaking through a chemical cartridge and/or improving the ability of the worker to breathe when using a particulate filter while still protecting the worker from particulates.

Figure 7:
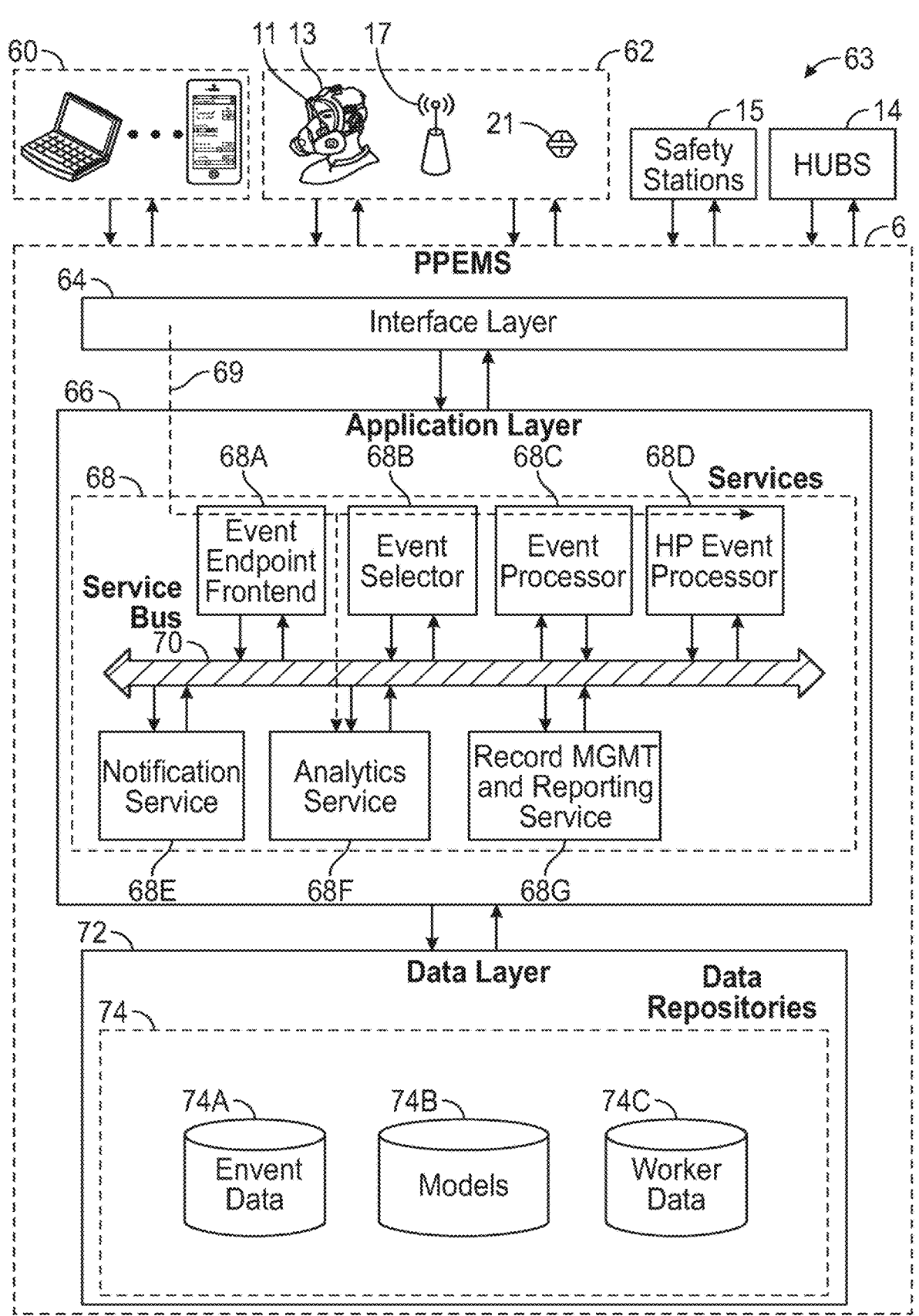
FIG. 7 is a block diagram illustrating, in detail, an operating perspective of the personal protection equipment management system shown in FIG. 5.

FIG. 7 is a block diagram providing an operating perspective of PPEMS 6 when hosted as cloud-based platform capable of supporting multiple, distinct environments 8 having an overall population of workers 10, in accordance with techniques described herein. In the example of FIG. 6, the components of PPEMS 6 are arranged according to multiple logical layers that implement the techniques of the disclosure. Each layer may be implemented by one or more modules comprised of hardware, software, or a combination of hardware and software.

In FIG. 7, safety equipment 62 include personal protective equipment (PPEs) (such as, for example negative pressure reusable respirators 13), beacons 17, and sensing stations 21. In some embodiments, negative pressure reusable respirators include at least one accessory 11 having computing device 300 (as shown in FIG. 7) operably disposed thereon. In some embodiments, computing device 300 operably disposed on accessory 11 is used alone or in combination with computing device 60.

Safety equipment 62, HUBs 14, safety stations 15, as well as computing devices 60, 300, operate as clients 63 that communicate with PPEMS 6 via interface layer 64. Computing devices 60, 300 typically execute client software applications, such as desktop applications, mobile applications, and web applications. Computing devices 60 may represent any of computing devices 16, 18 of FIG. 5, 60 of FIG. 7 and 300 of FIG. 8. Examples of computing devices 16, 18, 60, 300 may include a portable or mobile computing device (e.g., accessory 11, smartphone, wearable computing device, tablet), laptop computers, desktop computers, smart television platforms, and servers, to name only a few examples.

Client applications executing on computing devices 16, 18, 60, 300 may communicate with PPEMS 6 to send and receive data that is retrieved, stored, generated, and/or otherwise processed by services 68. For instance, the client applications may request and edit safety event data including analytical data stored at and/or managed by PPEMS 6. In some examples, client applications may request and display aggregate safety event data that summarizes or otherwise aggregates numerous individual instances of safety events and corresponding data obtained from safety equipment 62 and/or generated by PPEMS 6. The client applications may interact with PPEMS 6 to query for analytics data about past and predicted safety events, behavior trends of workers 10, to name only a few examples. In some examples, the client applications may output for display data received from PPEMS 6 to visualize such data for workers of clients 63. As further illustrated and described in below, PPEMS 6 may provide data to the client applications, which the client applications output for display in worker interfaces.

Client applications executing on computing devices 16, 18, 60, 300 may be implemented for different platforms but include similar or the same functionality. For instance, a client application may be a desktop application compiled to run on a desktop operating system or a mobile application compiled to run on a mobile operating system. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 7, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward data from the requests to services 68, and provide one or more responses, based on data received from services 68, to the client application that initially sent the request. In some examples, the one or more web servers that implement interface layer 64 may include a runtime environment to deploy program logic that provides the one or more inter- faces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the data to application layer 66, which includes services 68.

As shown in FIG. 7, PPEMS 6 also includes an application layer 66 that represents a collection of services for implementing much of the underlying operations of PPEMS 6. Application layer 66 receives data included in requests received from client applications 61 and further processes the data according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents logical interconnections or set of inter- faces that allows different services to send messages to other services, such as by a publish/subscription communication model. For instance, each of services 68 may subscribe to specific types of messages based on criteria set for the respective service. When a service publishes a message of a particular type on service bus 70, other services that sub- scribe to messages of that type will receive the message. In this way, each of services 68 may communicate data to one another. As another example, services 68 may communicate in point-to-point fashion using sockets or other communi- cation mechanisms. Before describing the functionality of each of services 68, the layers are briefly described herein.

Data layer 72 of PPEMS 6 represents a data repository that provides persistence for data in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage data in data repositories 74. The RDBMS software may manage one or more data repositories 74, which may be accessed using Structured Query Language (SQL). Data in the one or more databases may be stored, retrieved, and modified using the RDBMS software. In some examples, data layer 72 may be implemented using an Object Database Management System (ODBMS), Online Analytical Processing (OLAP) data- base or other suitable data management system.

As shown in FIG. 7, each of services 68A-68G (collec- tively, services 68) is implemented in a modular form within PPEMS 6. Although shown as separate modules for each service, in some examples the functionality of two or more services may be combined into a single module or compo- nent. Each of services 68 may be implemented in software, hardware, or a combination of hardware and software. Moreover, services 68 may be implemented as standalone devices, separate virtual machines or containers, processes, threads or software instructions generally for execution on one or more physical processors. In some examples, one or more of services 68 may each provide one or more interfaces that are exposed through interface layer 64. Accordingly, client applications of computing devices 16, 18, 60, 300 may call one or more interfaces of one or more of services 68 to perform techniques of this disclosure.

In accordance with techniques of the disclosure, services 68 may include an event processing platform including an event endpoint frontend 68A, event selector 68B, event processor 68C, high priority (HP) event processor 68D, notification service 68E, and analytics service 68F.

Event endpoint frontend 68A operates as a frontend interface for exchanging communications with hubs 14, safety stations 15, and safety equipment 62. In other words, event endpoint frontend 68A operates to as a frontline interface to safety equipment deployed within environments 8 and utilized by workers 10. In some instances, event endpoint frontend 68A may be implemented as a plurality of tasks or jobs spawned to receive individual inbound com- munications of event streams 69 that include data sensed and captured by the safety equipment 62. For instance, event streams 69 may include sensor data, such as first and second sensor data, from one or more negative pressure reusable respirators 13 and environmental data from one or more sensing stations 21. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry data recently captured data representing sensed conditions, motions, temperatures, actions or other data, generally referred to as events. Communications exchanged between the event endpoint frontend 68A and safety equipment 62 and/or hubs 14 may be real-time or pseudo real-time depending on communication delays and continuity.

Event selector 68B operates on the stream of events 69 received from safety equipment 62 and/or hubs 14 via frontend 68A and determines, based on rules or classifica- tions, priorities associated with the incoming events. For example, safety rules may indicate that incidents of incorrect equipment for a given environment, incorrect usage of PPEs, or lack of sensor data associated with a worker's vital signs are to be treated as high priority events. Based on the priorities, event selector 68B enqueues the events for sub- sequent processing by event processor 68C or high priority (HP) event processor 68D. Additional computational resources and objects may be dedicated to HP event pro- cessor 68D so as to ensure responsiveness to critical events, such as incorrect usage of PPEs, lack of vital signs, and the like. Responsive to processing high priority events, HP event processor 68D may immediately invoke notification service 68E to generate alerts, instructions, warnings or other simi- lar messages to be output to safety equipment 62, hubs 14, or devices used by workers 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of data generated by safety equipment 62. For example, in some instances, event data 74A may include entire streams of data obtained from negative pressure reusable respirator 13, sensing stations 21, etc. In other instances, event data 74A may include a subset of such data, e.g., associated with a particular time period.

Event processors 68C, 68D may create, read, update, and delete event data stored in event data 74A. Event data for may be stored in a respective database record as a structure that includes name/value pairs of data, such as data tables specified in row/column format. For instance, a name (e.g., column) may be "workerID" and a value may be an employee identification number. An event record may include data such as, but not limited to: worker identification, acquisition timestamp(s) and sensor data. For example, event stream 69 for one or more sensors associated with a given worker (e.g., worker 10A) may be formatted as follows:

{"eventTime": "2015-12-31T18: 20:53.1210933Z",
"workerID": "00123",
"RespiratorType": "Model 600",
"ContaminantCaptureDeviceType": "P90X",
"AirPressurePSI": 14.0}.

In some examples, event stream 69 include category identifiers (e.g., "eventTime", "workerID", "RespiratorType", "ContaminantCaptureDeviceType", and "AirPressurePSI"), as well as corresponding values for each category.

In some examples, analytics service 68F is configured to perform in depth processing of the incoming stream of events to perform real-time analytics. In this way, stream analytic service 68F may be configured to detect anomalies, transform incoming event data values, trigger alerts upon detecting safety concerns based on conditions or worker behaviors. In addition, stream analytic service 68F may generate output for communicating to safety equipment 62, safety stations 15, hubs 14, or computing devices 16, 18, 60, 300. In some embodiments, analytics service 68F is configured to operate as part of PPEMS, which can be operated by accessory 11 operably disposed on negative pressure reusable respirator 13.

Record management and reporting service (RMRS) 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups (e.g., types) of safety equipment 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example worker interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a worker can view PPE event information over a period of time and/or a computing device can analyze the PPE event information over the period of time.

In accordance with techniques of this disclosure, in some examples, analytics service 68F determines whether a contaminant capture device 23 of a negative pressure reusable respirator 13 is due for replacement. In one example, analytics service 68F determines whether a contaminant capture device 23A of negative pressure reusable respirator 13A of FIG. 5 is due for replacement based at least in part on sensor data (e.g., environmental sensor data and/or air pressure sensor data) and one or more rules. In some examples, the one or more rules are stored in models 74B. Although other technologies can be used, in some examples, the one or more rules are generated using machine learning. In other words, in one example implementation, analytics service 68F utilizes machine learning when operating on event streams 69 so as to perform real-time analytics. That is, analytics service 68F may include executable code generated by application of machine learning. The executable code may take the form of software instructions or rule sets and is generally referred to as a model that can subsequently be applied to event streams 69.

Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbor (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Analytics service 68F generates, in some example, separate models for individual workers, a population of workers, a particular environment, a type of respirator, a type of contaminant capture device, or combinations thereof. Analytics service 68F may update the models based on sensor data generated by PPE sensors or environmental sensors. For example, analytics service 68F may update the models for individual workers, a population of workers, a particular environment, a type of respirator, a type of contaminant capture device, or combinations thereof based on data received from safety equipment 62.

In some examples, analytics service 68F applies one or more of models 74B to event data 74A to determine whether contaminant capture device 23A of negative pressure reusable respirator 13A is due for replacement. In some examples, analytics service 68F applies one or more models 74B to sensor data received from negative pressure reusable respirator 13 to determine whether a contaminant capture device 23 is due for replacement. In one example, contaminant capture device 23A of respirator 13A includes a particulate filter and analytics service 68F receives sensor data (e.g., pressure data) from a pressure sensor that measures a gas characteristic, such as the air pressure of the air, within a cavity formed by the worker's face and respirator 13A. In some examples, analytics service 68F applies a model from models 74B to the air pressure data from the pressure sensor. For example, analytics service 68F may receive pressure data indicating a pressure differential in the air pressure within the cavity over time as the worker inhales, and may determine whether the particulate filter is due for replacement based on the air pressure differential.

In some examples, computing device 300 (shown in FIG. 8) is further configured to apply a model 322 to the first sensor data and the second sensor data to determine whether respiration occurred through the at least one valve and a wearer seal check was, performed, was not performed, was performed such that seal check met a certain quality standard, and combinations thereof. In some examples, analytics service 68F (shown in FIG. 7) applies a model from models 74B to the first sensor data and the second sensor data to determine whether respiration occurred through the at least one valve and a wearer seal check was performed, was not performed, was performed such that seal check met a certain quality standard, and combinations thereof. In some examples, model 74B of PPEMS 6 (shown in FIG. 7) or model 322 of computing device 300 (shown in FIG. 8) is trained based at least in part on first sensor data and second sensor data associated with one or more of the wearer, a plurality of additional wearers, contaminants within an environment around the wearer, a notification from another computing device, a type of contaminant capture device, or combinations thereof. In some embodiments, models useful in the present disclosure are time dependent.

In some examples, referring again to FIGS. 1 and 2, analytics service 68F may determine whether contaminant capture device 23A is due for replacement based on valve position data and gas characteristic data, such as pressure data. For example, analytics service 68F may apply one or more models of models 74B to negative pressure reusable respirator pressure sensor data and valve position sensor data. Typically, air pressure within the cavity formed between the worker's face and negative pressure reusable respirator decreases as the worker inhales. Additionally, the valve position may change as the worker inhales, due to the pressure differential within the negative pressure reusable respirator. For example, analytics service 68F may determine a pressure differential over time for the pressure when worker 10A inhales, and valve position data over the same time period. When contaminant capture device 23 is new, the pressure differential required to induce a relative change in valve position may be relatively small, compared to the pressure differential required to induce a relative change in valve position when contaminant capture device 23 is relatively saturated with particulates. For instance, when contaminant capture device 23 is relatively saturated, a greater pressure differential may be required to induce a relative change in valve position than when contaminant capture device 23 is new, due to the increased air flow resistance of contaminant capture device 23 relative to the valve.

In some examples, the sensor data received from safety equipment 62 includes physiological sensor data generated by one or more physiological sensors associated with a worker 10. Analytics service 68F may determine whether contaminant capture device 23A is due for replacement based on physiological data and pressure data. For example, analytics service 68F may apply one or more models of models 74B to PPE pressure sensor data and physiological sensor data. Typically, the air pressure within the cavity formed between the worker's face and respirator decreases as the worker inhales. For example, analytics service 68F may determine a pressure differential over time for the pressure when worker 10A inhales. When the particulate filter is new and the worker is not breathing heavily, the pressure differential may be relatively small, compared to the pressure differential when the particulate filter is relatively saturated with particulates. For instance, when the particulate filter is relatively saturated, worker 10A may breathe hard such that the pressure may decrease more than when the particulate filter is relatively new.

In some examples, analytics service 68F applies one or more models to at least the pressure data to determine whether the particulate filter is due for replacement. Models 74B may be trained based on pressure differentials for a particular worker, worker feedback indicating worker 10A is having difficulty breathing, a type of respirator, a type of particulate filter, a type of contaminant, or a combination therein. In some examples, the one or more models 74B are trained based on physiological data (e.g., heart rate data, breathing rate data). For example, a worker may breathe heavy (e.g., thus increasing the air pressure differential) because a filter is saturated (e.g., and due for replacement) or because a worker is physically active (e.g., moving within the environment, such as walking up stairs). In such examples, analytics service 68F applies one or more of models 74B to the PPE air pressure data and the physiological data to determine whether the particulate filter is saturated (e.g., such that the particulate filter is due for replacement). For example, analytics service 68F apply the models 74B to air pressure data indicating a relatively high pressure differential and physiological sensor data indicating a relatively high breathing rate and/or relatively high pulse rate, and determine based on application of the model 74B that the particulate filter is not due for replacement. In other words, analytics service 68G may infer that the worker is breathing hard because he or she is exercising rather than due to a saturated or congested particulate filter, such that analytics service 68F may determine that particulate filter is not due for replacement. As another example, analytics service 68F applies the models 74B to air pressure data indicating a relatively high pressure differential and physiological sensor data indicating a relatively low breathing rate and/or relatively low pulse rate, and determine based on application of the model 74B that the particulate filter is due for replacement.

In some examples, contaminant capture device 23B of negative pressure reusable respirator 13B includes a chemical cartridge and analytics service 68F determines whether the contaminant capture device 23B is due for replacement based at least in part on sensor data from one or more sensing stations 21. In one example, the sensor data includes data indicative the concentration level of one or more respective gases, vapor, or other chemicals present in the air of environment 8B of FIG. 5. Analytics service 68F applies one or more models 74B to the environmental sensor data generated by sensing stations 21 to determine whether contaminant capture device 23B is due for replacement. For instance, analytics service 68F may determine, based on application of one or more models 74B to the environmental sensor data, a threshold exposure time (e.g., a maximum amount of time) that contaminant capture device 23B provides protection. In some examples, analytics service 68F may determine an amount of time worker 10B is located within environment 8B, and compare the amount of time worker 10B is located within environment 8B to the threshold exposure time to determine whether contaminant capture device 23B is due for replacement. In some examples, hub 14A detects that worker 10A has entered environment 8B (e.g., based on GPS) and sends data indicating that worker 10A has entered environment 8B to PPEMS 6, such that analytics service 68F receives event data 74A (e.g., from hub 14) indicating worker 10A has entered environment 8B and tracks the time worker 10A is located within environment 8B.

In some examples, analytics service 68F dynamically determines an amount of contaminant capture device 23B (e.g., a chemical cartridge) that has been consumed. For example, analytics service 68F may apply one or more models 74B to environmental sensor data from sensing stations 21 continuously or periodically to determine the amount of contaminant capture device 23B consumed as conditions of environment 8B change throughout the day. In some instances, analytics service 68F determines that the concentration levels of a particular gas in environment 8B are relatively high and that a relatively high proportion (e.g., 40%) of contaminant capture device 23B has been exhausted or consumed while worker 10B utilized contaminant capture device 23B for a first period of time (e.g., two hours). In another instance, analytics service 68F may determine that the concentration levels of the particular gas decrease to a relatively low concentration (e.g., relative to the earlier period of time) and that a relatively low (e.g., 20%) of contaminant capture device 23B was exhausted or consumed in the second period of time. In one instance, analytics service 68F determines a cumulative amount of contaminant capture device 23B that has been consumed during the first and second periods of time. In some examples, analytics service 68F determines whether contaminant capture device 23B is due for replacement by comparing the cumulative consumption to a threshold consumption. As one example, analytics service 68F determines that contaminant capture device 23B is due for replacement in response to determining that the cumulative consumption satisfies (e.g., is greater than) the threshold consumption or that contaminant capture device 23B is not due for replacement in response to determining that the cumulative consumption does not satisfy (e.g., is less than) the threshold consumption.

As described above, analytics service 68F determines, in one example, whether contaminant capture device 23B is due for replacement based on applying one or more models 74B to at least a portion of event data 74A. Models 74B may be trained based on event data 74A associated with a particular worker, a plurality of workers, the particular contaminants within the work environment 8B, a type of contaminant capture device 23 utilized by the worker, or a combination therein. In some instances, the particular models 74B applied to the event data 74A for worker 10A are trained based on event data 74A for workers 10A and the models 74B applied to event data 74A for worker 10B are trained based on event data 74A for worker 10B. In one example, the particular models 74B applied to the event data 74A for worker 10A are trained based on event data 74A for a plurality of workers 10. In some examples, the particular models 74B applied to the event data 74A for worker 10A are trained based on the type of contaminant capture device 23A utilized by worker 10A. As yet another example, the particular models 74B applied to the event data 74A for worker 10A may be trained based on contaminants within work environment 8B, while the particular models 74B applied to the event data 74A for a worker within environment 8A may be trained based on contaminants within work environment 8A.

PPEMS 6 performs one or more actions in response to determining that contaminant capture device 23 is due for replacement. In some examples, notification service 68E outputs a notification indicating that a contaminant capture device 23 is due for replacement. For example, notification service 68E may output the notification to at least one of clients 63 (e.g., one or more of computing devices 60, hubs 14, safety stations 15, or a combination therein). In one instance, the notification indicates which worker of workers 10 is associated with the article or component that is due for replacement, a location of the worker, a location at which a replacement is located, etc. As another example, notification service 68E may output a command (e.g., to a respective hub 14A or other computing device associated with worker 10A, such as a computing device 300 illustrated in FIG. 8) to output an alert indicating contaminant capture device 23A is due for replacement. For example, respirator hub 14A may receive the command and may output an alert (e.g., visual, audible, haptic) to indicate contaminant capture device 23A is due for replacement. While PPEMS 6 is described as determining whether contaminant capture device 23 is due for replacement and performing actions, a computing device (e.g., a hub 14 or computing device of negative pressure reusable respirator 13) associated with a worker may perform similar functionality.

In some examples, analytics service 68F determines, based on event data 74A, whether a contaminant capture device 23 of the negative pressure reusable respirator 13 satisfies one or more safety rules (e.g., for a task to be performed, for the hazards present or likely to be present within work environment 8B). For example, analytics service 68F may determine whether one or more contaminant capture devices 23 utilized by a worker 10 (e.g., contaminant capture devices 23A utilized by worker 10A) satisfies one or more safety rules associated with work environment 8B. In some instances, models 74B include safety rules specifying a type of contaminant capture device 23 associated with each of work environments 8B or associated with particular hazards (e.g., gases, vapors, particulates). In such instances, analytics service 68F determines whether contaminant capture devices 23A satisfies the safety rules based on data received from the contaminant capture device 23A. For instance, each identification information corresponding to the contaminant capture device 23A (e.g., information identifying a type of the contaminant capture device 23A) and a communication device, such as an RFID tag (e.g., passive RFID tag), that transmits the information. In one instance, the memory device includes an RFID tag that stores identification information for contaminant capture device 23A. In another instance, contaminant capture device 23A includes an identifier indicative of identification information for contaminant capture device 23A.

In some examples, negative pressure reusable respirator 13A includes a computing device (e.g., located between the facepiece and the worker's contaminant capture device 23 may include a memory device that stores information) that includes a communication device (e.g., a RFID reader) configured to receive information from a contaminant capture device 23A. In one example, negative pressure reusable respirator 13A includes a computing device that receives the identification information from negative pressure reusable respirator 13A and outputs the identification information to PPEMS 6. PPEMS 6 may receive the identification information (e.g., indicating a type of contaminant capture device 23A), determine one or more rules associated with contaminant capture device 23A, and determine whether the type of the contaminant capture device 23A satisfies the rules. In one instance, analytics service 68F determines whether the type of contaminant capture device 23A is the correct type of contaminant capture device 23A for the environment or hazards within the environment. As another example, a computing device associated with worker 10A (e.g., hub 14A or a computing device 16, 18, 60 and 300) may determine whether contaminant capture device 23A satisfies the one or more safety rules.

In accordance with one or more aspects of this disclosure, in some examples, analytics service 68F determines whether usage of one or more negative pressure reusable respirators 13 satisfies one or more safety rules associated with a worker. In one example, analytics service 68F determines whether usage of negative pressure reusable respirator 13A by worker 10A satisfies a safety rule based at least in part on worker data 74C, models 74B, event data 74A (e.g., sensor data), or a combination therein. The safety rules may be associated with conditions indicating whether a worker is clean shaven or lifts a respirator from his or her face.

In some examples, analytics service 68F determines whether usage of negative pressure reusable respirator 13A satisfies a safety rule by comparing a distance between negative pressure reusable respirator 13A and a face of worker 10A to a threshold distance. Analytics service 68F determine the distance between negative pressure reusable respirator 13A and a face of worker 10A based on sensor data. In one instance, event data 74A for worker 10A includes sensor data indicative of the distance (e.g., actual distance) between the face of worker 10A and negative pressure reusable respirator 13A. For instance, the event data 74A may include data generated by an infrared sensor of a computing device of negative pressure reusable respirator 13A. In some examples, analytics service 68F determines that the distance between the face of worker 10A and negative pressure reusable respirator 13A satisfies (e.g., is greater than or equal to) a threshold distance, which may indicate that worker 10A has lifted negative pressure reusable respirator 13A away from his or her face, that worker 10A has facial hair (e.g., is not clean shaven), that negative pressure reusable respirator 13A is not positioned properly upon the face of worker 10A, that worker 10A has not completed a wearer seal check that satisfies a least one threshold, information about the physical state of a negative pressure reusable respirator 13A, or usage information about a negative pressure reusable respirator 13A.

In some examples, the threshold distance may be associated with a group of workers 10. For example, analytics service 68F may utilize a single threshold distance for each of workers 10. In some examples, each worker of workers 10A may be associated with a respective threshold distance (e.g., stored in worker data 74C or safety rules 74B). For example, to ensure the space between the face of worker 10A and negative pressure reusable respirator 13A remains sealed from contaminated air within work environment 8B, worker 10A may be required to be clean shaven. Worker 10A may be clean shaven when at least a threshold amount of facial hair (e.g., 80%, 90%, 95%, etc.) is removed from portions of worker 10A's face that are capable of growing facial hair. In such examples, the threshold distance associated with each respective worker of workers 10 may correspond to respective distance between the face of the worker and a respirator when the worker is known to be clean shaven. In other words, the threshold distance for worker 10A may be different than the threshold distance for worker 10B. In one example, analytics service 68F determines that the usage of negative pressure reusable respirator 13A satisfies a safety rule by determining that the distance between the face of worker 10A and negative pressure reusable respirator 13A satisfies (e.g., is greater than) the threshold distance associated with worker 10A. As another example, analytics service 68F may determine that the usage of negative pressure reusable respirator 13B does not satisfy the safety rule by determining that the distance between the face of worker 10B and negative pressure reusable respirator 13B does not satisfy (e.g., is less than) the threshold distance associated with worker 10B.

According to some examples, analytics service 68F may determine whether the distance between the face of worker 10A and negative pressure reusable respirator 13A satisfies different threshold distances. For example, a first threshold distance may be associated with the presence of facial hair and a second threshold distance (e.g., greater than the first threshold distance) may be lifting or removing the negative pressure reusable respirator 13. In some examples, analytics service 68F may determine that worker 10A has facial hair (e.g., is not clean shaven) in response to determining that the distance between the face of worker 10A and negative pressure reusable respirator 13A satisfies a first threshold distance, and that worker 10A has lifted negative pressure reusable respirator 13A away from his face in response to determining that the distance between the face of worker 10A and negative pressure reusable respirator 13A satisfies a second threshold distance, that worker 10A has not completed a wearer seal check that satisfies a least one threshold, information about the physical state of a negative pressure reusable respirator 13A, or usage information about a negative pressure reusable respirator 13A.

In some examples, analytics service 68F determines whether a particular worker satisfies one or more safety rules that are associated with a worker. In some examples, the safety rules associated with a worker may include rules indicating a level of experience or training the worker should have to perform certain tasks or work in certain work environments. In some examples, analytics service 68F determines whether worker 10A satisfies one or more safety rules associated with worker 10A based at least in part on worker data 74C. For example, worker data 74C may include data indicating an experience level of each worker of workers 10, trainings received by each worker of workers 10, or a combination therein. Analytics service 68F may determine whether worker 10A satisfies one or more safety rules of models 74B by querying worker data 74C and comparing the worker data associated with worker 10A to the safety rules. For instance, safety rules 74B may indicate one or more training a worker 10 must receive prior to using a particular negative pressure reusable respirator 13 (e.g., a particular type of negative pressure reusable respirator 13). Analytics service 68F may determine whether worker 10A satisfies such a safety rule by querying worker data 74C to determine whether worker 10A has been trained to use negative pressure reusable respirator 13A.

In some examples, notification service 68E outputs a notification in response to determine that a safety rule is not satisfied (e.g., a worker 10 does not satisfy a safety rule, or an article of PPE or component of an article of PPE does not satisfy a safety rule). For example, notification service 68E may output the notification to at least one of clients 63 (e.g., one or more of computing devices 60, hubs 14, safety stations 15, or a combination therein). In some examples, the notification indicates whether contaminant capture device 23A satisfies the one or more rules. The notification may indicate which worker of workers 10 is associated with the article or component that is due for replacement, a location of the worker, a location at which a replacement is located, etc. In some examples, the notification may indicate that a worker is not clean shaven or has lifted a respirator away from his or her face. As another example, the notification may indicate that worker 10A is not trained to utilize the particular negative pressure reusable respirator 13.

FIG. 8 is a conceptual diagram illustrating an example negative pressure reusable respirator, in accordance with aspects of this disclosure. Negative pressure reusable respirator 13A is configured to receive (e.g., be physically coupled to) one or more contamination capture devices 23A, such as a particulate filter, a chemical cartridge, or both. Negative pressure reusable respirator 13A is configured to physically couple to computing device 300. Negative pressure reusable respirator 13A includes a facepiece (e.g., a full facepiece, or a half facepiece) 301 configured to cover at least a worker's nose and mouth. In some examples, computing device 300 is located with facepiece 301. It should be understood that the architecture and arrangement of negative pressure reusable respirator 13A and computing device 300 illustrated in FIG. 8 is shown for exemplary purposes only. In other examples, negative pressure reusable respirator 13A and computing device 300 may be configured in a variety of other ways having additional, fewer, or alternative components than those shown in FIG. 8.

In the example of FIG. 8, contamination capture device 23A includes a memory device and a communication device, such as RFID tag (e.g., passive RFID tag) 350. RFID tag 350 stores information corresponding to contaminant capture device 23A (e.g., information identifying a type of the contaminant capture device 23A) and outputs the information corresponding to contaminant capture device 23A in response to receiving a signal from another communication device (e.g., an RFID reader).

Computing device 300 may be configured to physically couple to negative pressure reusable respirator 13A. In some embodiments, computing device 300 is operably disposed on an accessory 11, where accessory 11 is operably disposed on negative pressure reusable respirator 23. In some examples, accessory 11 or computing device 300 may be disposed between facepiece 301 of negative pressure reusable respirator 13A and a face of worker 10A. For example, accessory 11 or computing device 300 may be physically coupled to an inner wall of the respirator cavity. Accessory 11 or computing device 300 may be integral with negative pressure reusable respirator 13A or physically separable from negative pressure reusable respirator 13A. In some examples, accessory 11 or computing device 300 is physically separate from negative pressure reusable respirator 13A and communicatively coupled to negative pressure reusable respirator 13A. For example, computing device 300 may be a smartphone carried by worker 10A or a data hub worn by worker 10A.

Computing device 300 includes one or more processors 302, one or more storage devices 304, one or more communication units 306, one or more sensors 308, one or more output units 318, sensor data 320, models 322, and worker data 324. Processors 302, in one example, are configured to implement functionality and/or process instructions for execution within computing device 300. For example, processors 302 may be capable of processing instructions stored by storage device 304. Processors 302 may include, for example, microprocessors, digital signal processors (DSPs), application specific integrated circuits (ASICs), field-programmable gate array (FPGAs), or equivalent discrete or integrated logic circuitry.

Storage device 304 may include a computer-readable storage medium or computer-readable storage device. In some examples, storage device 304 may include one or more of a short-term memory or a long-term memory. Storage device 304 may include, for example, random access memories (RAM), dynamic random access memories (DRAM), static random access memories (SRAM), magnetic hard discs, optical discs, flash memories, or forms of electrically programmable memories (EPROM) or electrically erasable and programmable memories (EEPROM).

In some examples, storage device 304 may store an operating system or other application that controls the operation of components of computing device 300. For example, the operating system may facilitate the communication of data from electronic sensors 308 to communication unit 306. In some examples, storage device 304 is used to store program instructions for execution by processors 302. Storage device 304 may also be configured to store information within computing device 300 during operation. In some examples, storage device 304 may also be configured to transmit information from to a second device, such as for example, a remote wearer 24, a computing device 16, 18 that may be located remote from storage device 304, and combinations thereof. In some embodiments, the second device is integral or separate from storage device 304.

Storage device 304 is configured to store information related to at least one of: a time; a time duration; a state of the negative pressure reusable respirator; usage information relating to the negative pressure reusable respirator; whether at least one contaminant capture device coupled to a negative pressure reusable respirator is due for replacement; whether usage of the negative pressure reusable respirator satisfies one or more safety rules associated with the negative pressure reusable respirator; sensor data; or combinations thereof.

Computing device 300 may use one or more communication units 306 to communicate with external devices via one or more wired or wireless connections. Communication units 306 may include various mixers, filters, amplifiers and other components designed for signal modulation, as well as one or more antennas and/or other components designed for transmitting and receiving data. Communication units 306 may send and receive data to other computing devices using any one or more suitable data communication techniques. In some embodiments, the other computing devices, such as a second device, are integral or separate from computing device 300. Examples of such communication techniques may include TCP/IP, Ethernet, Wi-Fi, Bluetooth, 4G, LTE, to name only a few examples. In some instances, communication units 306 may operate in accordance with the Bluetooth Low Energy (BLU) protocol. In some examples, communication units 306 may include a short-range communication unit, such as an RFID reader.

In general, computing device 300 includes a plurality of sensors 308, such as a first sensor and a second sensor, that generate sensor data indicative of operational characteristics of negative pressure reusable respirator 13A, contaminant capture devices 23A, and/or an environment in which negative pressure reusable respirator 13A is used. Sensors 308 may include an accelerometer, a magnetometer, an altimeter, an environmental sensor, among other examples. In some examples, environment sensors may include one or more sensors configured to measure temperature, humidity, particulate content, gas or vapor concentration levels, or any variety of other characteristics of environments in which negative pressure reusable respirator 13A are used. In some examples, one or more of sensors 308 may be disposed between facepiece 301 of negative pressure reusable respirator 13A and a face of worker 10A. For example, one of sensors 308 (e.g., an air pressure sensor) may be physically coupled to an inner wall of the respirator cavity.

In an example of FIG. 8, sensors 308 include one or more air pressure sensors 310 configured to measure air pressure within a cavity formed or defined by a face of worker 10A and negative pressure reusable respirator 13A. In other words, air pressure sensors 310 detect the air pressure of the air located in the sealable space between the face of worker 10A and facepiece 301 as the worker inhales and exhales.

In an example of FIG. 8, sensors 308 also include one or more valve position sensor 311 configured to generate data indicative of a position of the at least one valve in the negative pressure reusable respirator 13A. In some instances as shown in FIG. 8, sensors 308 include a first sensor, such as one or more air pressure sensors 310, configured to generate first sensor data indicative of a gas characteristic in a sealed space formed by a face of the wearer and the negative pressure reusable respirator 13A and a second sensor, such as a valve position sensor 311, configured to generate second sensor data indicative of a position of the at least one valve.

Computing device 300 includes one or more output units 318 configured to output data that is indicative of operation of negative pressure reusable respirator 13A. In some examples, output unit 318 output data from the one or more sensors 308 of negative pressure reusable respirator 13A. For example, output unit 318 may generate one or more messages containing real-time or near real-time data from one or more sensors 308 of negative pressure reusable respirator 13A for transmission to another device via communication unit 306. In some examples, output unit 318 are configured to transmit the sensor data in real-time or near-real time to another device (e.g., safety equipment 62) via communication unit 306. However, in some instances, communication unit 306 may not be able to communicate with such devices, e.g., due to an environment in which negative pressure reusable respirator 13A is located and/or network outages. In such instances, output unit 318 may cache usage data to storage device 304. That is, output unit 318 (or the sensors themselves) may send usage data to storage device 304, e.g., as sensor data 320, which may allow the usage data to be uploaded to another device upon a network connection becoming available.

In some examples, output unit 318 is configured to generate an audible, visual, tactile, or other output that is perceptible by a worker of negative pressure reusable respirator 13A. Examples of output are audio, visual, or tactile output. For example, output units 318 include one more worker interface devices including, as examples, a variety of lights, displays, haptic feedback generators, speakers or the like. Output units 318 may interpret received alert data and generate an output (e.g., an audible, visual, or tactile output) to notify a worker using negative pressure reusable respirator 13A of an alert condition (e.g., that the likelihood of a safety event is relatively high, that the environment is dangerous, that negative pressure reusable respirator 13A is malfunctioning, that one or more components of negative pressure reusable respirator 13A need to be repaired or replaced, or the like).

According to aspects of this disclosure, processors 302 utilize sensor data (e.g., data from pressure sensors 310, valve position sensors 311, environmental sensors 312, and/or infrared sensors 314 of computing device 300, data from sensing stations 21 of FIG. 5, or other sensors) in a variety of ways. In some examples, processors 302 are configured to perform all or a portion of the functionality of PPEMS 6 described in FIGS. 1 and 2. While processors 302 are described as performing the functionality in FIG. 8, in some examples, other devices (e.g., PPEMS 6, hubs 14, other devices, or a combination therein) perform functionality described with reference to processors 302.

In the example of FIG. 8, computing device 300 includes sensor data 320, models 322, and worker data 324. Sensor data 320 includes data regarding operation of negative pressure reusable respirator 13A, physiological conditions of worker 10A, characteristics of environment 8B, or a combination thereof. In other words, sensor data 320 may include data from PPE sensors, physiological sensors, and/or environmental sensors. Models 322 include historical data (e.g., historical sensor data) and models, such as models 74B described with reference to FIG. 7. Worker data 324 may include worker profiles, such as worker data 74C described with reference to FIG. 7.

Processors 302 may determine comparative data by comparing first sensor data to second sensor data, where a first sensor, such as an air pressure sensor 310, is configured to generate first sensor data indicative of a gas characteristic in a sealed space formed by a face of the wearer and the negative pressure reusable respirator, and a second sensor, such as a valve position sensor 311, is configured to generate second sensor data indicative of a position of the at least one valve. In some instances, first sensor data and second sensor data are stored in sensor data 320. In some instances, processors 302 apply one or more models 322 to sensor data 320 to determine a gas characteristic in a sealed space formed by a face of the wearer and the negative pressure reusable respirator and a position of the at least one valve in the negative pressure reusable respirator. In some examples, models 322 may be trained based on historical data (e.g., air pressure data, physiological sensor data). In some instances, such historical data may relate to an individual wearer, aggregated from a group of wearers, or a combination thereof.

In some embodiments, processors 302 may determine whether contamination capture devices 23A are due for replacement based at least in part on air pressure data generated by air pressure sensors 310 or environmental data generated by an environmental sensors 312 (additionally or alternatively, by sensing stations 21 of FIG. 5). In some instances, processors 302 apply one or more models 322 to sensor data 320 to determine whether contamination capture devices 23A are due for replacement. In some examples, models 322 may be trained based on historical data (e.g., air pressure data, physiological sensor data). For example, models 322 may be trained on historical air pressure data associated with worker 10A, historical physiological data, and historical worker feedback from worker 10A indicating worker 10A is having difficulty breathing, which may indicate that a particulate filter of contamination capture device 23A is saturated and/or due for replacement. In such examples, processors 302 apply models 322 to predict when contamination capture devices 23A are due for replacement based on current (e.g., real-time, or near real-time) air pressure data from air pressure sensors 310.

In some examples, models 322 are trained on historical environmental data (e.g., indicative of gas or vapor concentration levels) generated by environmental sensors 312 or sensing stations 21 of FIG. 5 and historical determinations of contaminant capture device lifespan. Processors 302 may apply models 322 to current environmental sensor data to determine a threshold exposure time and compare an actual exposure time to the threshold exposure time to determine whether contaminant capture device 23A is due for replacement. As another example, processors 302 may apply models 322 to current environmental sensor data to determine a cumulative consumption and compare the cumulative consumption to a threshold consumption to determine whether contaminant capture device 23A is due for replacement.

In some examples, processors 302 determine whether the sealable space between a face of worker 10A and respirator 13A is sealed. The sealable space may not be sealed when there is a leak in the seal, when respirator 13A is not properly positioned on the face of worker 10A, or when worker 10A removes respirator 13A. Processors 302 may determine whether the sealable space is sealed based at least in part on the air pressure data. For example, processors 302 may compare the pressure to a baseline pressure (e.g., a pressure when respirator 13A is known to provide a seal) and determine that the seal is broken in response to determining that the pressure does not satisfy the baseline pressure. In such examples, output units 318 may output an alert indicating a possible leak in the seal.

In some examples, processors 302 determine whether negative pressure reusable respirator 13A and/or contaminant capture device 23A satisfies one or more safety rules associated with a particular work environment (e.g., environment 8B of FIG. 5). In some instances, safety rules are pre-programmed rules related to some attribute of the negative pressure reusable respirator, such as for example usage, performance, wearer fit, and the like. In some instances, safety rules are stored in storage device 304 integral to the negative pressure reusable respirator 13A. In some instances, safety rules generated by processors 302 compare usage of wearer's negative pressure reusable respirator 13A to data external to the computing device 300.

In some examples, the safety rules may indicate that respirator 13A should be worn. In some examples, infrared sensor 314 outputs data indicative of whether respirator 13A is worn. In some embodiments, infrared sensor 314 outputs data indicative of whether at least one valve had any position changes. For example, the infrared sensor data may include data indicating a distance between respirator 13A or at least one valve 9 and the nearest object. In some instances, processors 302 determine whether respirator 13A is worn by comparing the distance to a threshold distance. For instance, the threshold distance may be a distance between facepiece 301 and the face of worker 10A when worker 10A is known to be wearing respirator 13A. In other examples, the threshold distance may be a distance between the at least one valve 9 and a portion of respirator 13A when worker is known to be respirating through the at least one valve 9. As another example, the infrared sensor data may include temperature data. Processors 302 may determine whether respirator 13A is worn by comparing the temperature data to a threshold temperature that is indicative of a human body (e.g., approximately 98.6 degrees Fahrenheit or approximately 37 degrees Celsius).

In some instances, the safety rules indicate that a contaminant capture device 23A should be physically coupled to respirator 13A. In such instances, processors 302 determine whether contaminant capture device 23A is present (e.g., attached to respirator 13A) by causing communication units 306 to emit an RFID signal and determining whether communication units 306 receive a signal that includes identification information for a contaminant capture device 23. In one example, processors 302 determine that a contaminant capture device 23 is not present when identification information is not received and determine that a contaminant capture device 23 is present identification information is received.

Processors 302 may determine whether contaminant capture devices 23A satisfies the safety rules based at least in part on data received from the contaminant capture device 23A. For instance, contaminant capture device 23A may include RFID tag 350 that stores identification information corresponding to the contaminant capture device 23A (e.g., information identifying a type of the contaminant capture device 23A). Processors 302 may receive the identification information for contaminant capture device 23A. For instance, models 322 may include data indicative of one or more safety rules, such as indicating the type of contaminant capture device 23A associated with various hazards or environments.

Processors 302 determine, in some examples, whether contaminant capture device 23A satisfies a safety rule by determining whether contaminant capture device 23A is authentic. In some examples, processors 302 determine whether contaminant capture device 23A is authentic based on the identification information. For example, processors 302 may authenticate the contaminant capture device by comparing the received identification information to known authentication information. In some instances, equipment data 326 includes authentication information for authentic or verified contaminant cartridge devices. In such instances, processors 302 may query equipment data 326 to determine whether contaminant capture device 23A is authentic. In other example, processors 302 query a remote computing device (e.g., PPEMS 6) via communication units 306 to determine whether contaminant capture device 23A is authentic. For example, processors 302 may output a notification to PPEMS 6 that includes the identification information of contaminant capture device 23A and a request for PPEMS 6 to authenticate the identification information. Responsive to determining that contaminant capture device 23A is not present or is not authentic, computing device 300 may output a notification (e.g., to PPEMS 6) indicating that contaminant capture device 23A is not present or is not authentic. In some examples, output units 318 output an alert (e.g., audible, visual, haptic) indicating that contaminant capture device 23A is not present or is not authentic in response to determining that that contaminant capture device 23A is not present or is not authentic.

In some examples, processors 302 determine, based on the identification information and models 322, whether contaminant capture device 23A satisfies the safety rules by determining whether the type of the contaminant capture device 23A corresponds to (e.g., is a same or similar to) the type of the contaminant capture device associated with the environment or hazards within the environment. In other words, processors 302 may determine whether contaminant capture device 23A is the right type of particulate filter or chemical cartridge to protect worker 10A in the work environment.

Processors 302 may determine whether usage of one or more negative pressure reusable respirator 13A satisfies one or more safety rules associated with worker 10A. In some examples, the safety rules are associated with conditions indicating whether a worker is clean shaven or lifts a respirator from his or her face. In some examples, processors 302 determines whether usage of negative pressure reusable respirator 13A satisfies a safety rule by determining whether worker 10A is clean shaven or lifts negative pressure reusable respirator 13A from his or her face. In one example, processors 302 determine whether worker 10A is clean shaven by determining a distance between negative pressure reusable respirator 13A and the face of worker 10A and comparing the distance to a threshold distance. For instance, processors 302 may receive data indicating the distance between negative pressure reusable respirator 13A and the face of worker 10A from infrared sensor 314, such that processors 302 determine that worker 10A is not clean shaven in response to determining that the distance satisfies (e.g., is greater than) a first threshold distance associated with worker 10A. In another example, processors 302 determine that worker 10A has lifted respirator 13A from his or her face in response to determining that the distance satisfies (e.g., is greater than) a second threshold distance.

In some examples, processors 302 determine whether worker 10A satisfies one or more safety rules that are associated with worker 10A. For example, processors 302 may determine whether worker 10A has the experience or training to work in a particular environment (e.g., environment 8B of FIG. 5), perform a particular task, operate a particular type of equipment, utilize a particular type of respirator, etc. For instance, worker data 324 includes a worker profile indicating an experience level of worker 10A, trainings received by worker 10A, demographic data (e.g., age) for worker 10A, medical data for worker 10A, whether worker 10A has been fitted for a particular type of respirator 13A, among other data. Worker data 324 includes worker profiles for worker 10A and additional workers 10. In one example, processors 302 apply one or more models 322 to worker data 324 (e.g., a worker profile) to determine whether worker 10A satisfies one or more safety rules. For example, processors 302 may determine whether worker 10A has been trained in hazards associated with the work environment in which worker 10A is located. As another example, processors 302 may determine whether worker 10A has been trained in the type of respirator 13A and/or contaminant capture device 23A associated with hazards in environment 8B. In some instances various sensors and thresholds may be used together to determine various performance, usage or physical states of respirator 13A.

Output units 318 output one or more alerts in response to determining that negative pressure reusable respirator 13A and/or contaminant capture device 23A satisfies one or more safety rules associated with a particular work environment. In one example, output units 318 include one or more light sources that emit light (e.g., of one or more color) indicative of a status of the negative pressure reusable respirator 13A. For instance, output unit 318 may output light of a first color (e.g., green) to indicate a normal status, light of a second color (e.g., yellow) to indicate contaminant capture device 23A is approaching time for replacement, and a light of a third color to indicate contaminant capture device 23A is due for immediate replacement. In another example, output units 318 output an alert in response to determining that usage of one or more negative pressure reusable respirator 13A satisfies one or more safety rules or in response to determining that worker 10A satisfies one or more safety rules. For example, output units 318 may output light of a first color in response to determining that worker 10A does not satisfy a safety rule (e.g., is not trained on a particular type of negative pressure reusable respirator 13A) or output light of a second color in response to determining that contaminant capture device 23A does not satisfy a safety rule (e.g., does not protect against hazards known to be present in the work environment).

In some examples, output units 318 output notifications to one or more other computing devices (e.g., hub 14A of FIG.

5, PPEMS 6 of FIG. 5, or both) via communication units 306. For example, the notification may include data indicating the identity of worker 10A, an environment 8B in which worker 10A is located, whether one or more safety rules are satisfied, among others. In some examples, the notification may indicate that a contaminant capture device 23A is due for replacement, that worker 10A is not clean shaven, that worker 10A has not completed a wearer seal check that satisfies a least one threshold, that worker 10A has lifted negative pressure reusable respirator 13A from his or her face, information about the physical state of a negative pressure reusable respirator, or usage information about a negative pressure reusable respirator.

FIG. 10 is a flowchart illustrating example operations of an example computing system, in accordance with various techniques of this disclosure. FIG. 10 is described below in the context of negative pressure reusable respirator 13A of FIG. 5, PPEMS 6 of FIGS. 4 and 2, and/or computing device 300 of FIG. 8. While described in the context of negative pressure reusable respirator 13A, PPEMS 6, and/or computing device 300, other computing devices (e.g., a hub of hubs 14 of FIG. 5) may perform all or a subset of the functionality described.

In some examples, at least one computing device receives sensor data indicative of a characteristic of air within a work environment (402). For example, negative pressure reusable respirator 13A may include a computing device 300 or may be configured to physically couple to computing device 300. In other words, computing device 300 may be integrally formed within negative pressure reusable respirator (e.g., non-removable) or may be attachable/detachable, such as for example as being operably disposed on at least one accessory 11, where accessory 11 is operably disposed on and internal or external surface of negative pressure reusable respirator 13A. In one instance, computing device 300 receives sensor data from one or more sensors configured to generate sensor data indicative of a characteristic of air within a work environment. Additionally or alternatively, PPEMS 6 may receive the sensor data. In one example, the sensor data includes data generated by a first sensor, such as an air pressure sensor 310 used to indicate air pressure within a sealable or sealed space formed (e.g., defined) by a face of worker 10A and negative pressure reusable respirator 13A. In another example, the sensor data includes data generated by a second sensor, such as a valve position sensor 311 used to indicate position of at least valve in negative pressure reusable respirator 13A. In one example, the sensor data includes data generated by a first sensor, such as an air pressure sensor 310 used to indicate air pressure within a sealable or sealed space formed (e.g., defined) by a face of worker 10A and negative pressure reusable respirator 13A and data generated by a second sensor, such as a valve position sensor 311 used to indicate position of at least valve in negative pressure reusable respirator 13A. As another example, the sensor data may include data generated by an environmental sensor (e.g., environmental sensor 312 or sensing stations 21), such as environmental data indicative of a gas or vapor concentration level within a work environment (e.g., environment 8B of FIG. 5).

The at least one computing device determines, based at least in part on the sensor data, various usage or physical state information about the negative pressure reusable respirator. For example, the at least one computing device determines, based at least in part on the sensor data, whether at least one contaminant capture device coupled to a negative pressure reusable respirator is due for replacement (404). For example, the at least one computing device may determines whether at least one contaminant capture device 23A is due for replacement based at least in part on air pressure data, environmental data, or both. In some examples, computing device 300 and/or PPEMS 6 determines whether at least one contaminant capture device 23A is due for replacement based at least in part on data from air pressure data. For example, PPEMS 6 and/or computing device 300 may determine whether the air pressure within the sealable space formed by the worker's face and negative pressure reusable respirator 13A decreases below a threshold air pressure when the worker inhales.

In some examples, PPEMS 6 and/or computing device 300 determine whether the at least one contaminant capture device 23A is due for replacement based at least in part on the environmental data. According to some examples, PPEMS 6 and/or computing device 300 determines a threshold exposure time for the contaminant capture device 23A based on the environmental data (e.g., gas or vapor concentration level) and compares the actual exposure time for contaminant capture device 23A to the threshold exposure time. As another example, the computing device 300 and/or PPEMS 6 may determine a cumulative consumption of the contaminant capture device 23A and compare the cumulative consumption of the contaminant capture device 23A to a threshold consumption to determine whether contaminant capture device 23A is due for replacement.

At least one computing device performs one or more actions in response to determining the at least one contaminant capture device is due for replacement (406). In some examples, PPEMS 6 outputs a notification to another computing device (e.g., computing devices 16, 18 of FIG. 5) indicating contaminant capture device 23A is due for replacement. In another example, output unit 318 of computing device 300 outputs an alert indicating that contaminant capture device 23A is due for replacement.

According to some examples, at least one computing device determines, based on the data indicative of a position of the negative pressure reusable respirator relative to the face of the worker, whether usage of the negative pressure reusable respirator satisfies one or more safety rules associated with the negative pressure reusable respirator. In some instances, computing device 300 receives sensor data from an infrared sensor 314, the sensor data indicating a distance between negative pressure reusable respirator 13A and a face of worker 10A. In one instance, computing device 300 and/or PPEMS 6 determine, based on the distance, whether worker 10A is clean shaven and/or whether negative pressure reusable respirator 13A has been lifted from the face of worker 10A.

In some examples, PPEMS 6 and/or computing device 300 determine whether contaminant capture device 23A satisfies one or more safety rules associated with work environment 8B. In one example, contaminant capture device 23A include an RFID tag 350 and a communication unit 306 of computing device 300 includes an RFID reader. In such examples, one of communication units 306 receives identification information for contaminant capture device 23A from RFID tag 352 and determines whether contaminant capture device 23A satisfies one or more safety rules associated with the environment based on the identification information. For example, computing device 300 may determine whether contaminant capture device 23A fits negative pressure reusable respirator 13A or whether contaminant capture device 23A is configured to protect worker 10A from hazards associated with environment 8B.

Figure 12:
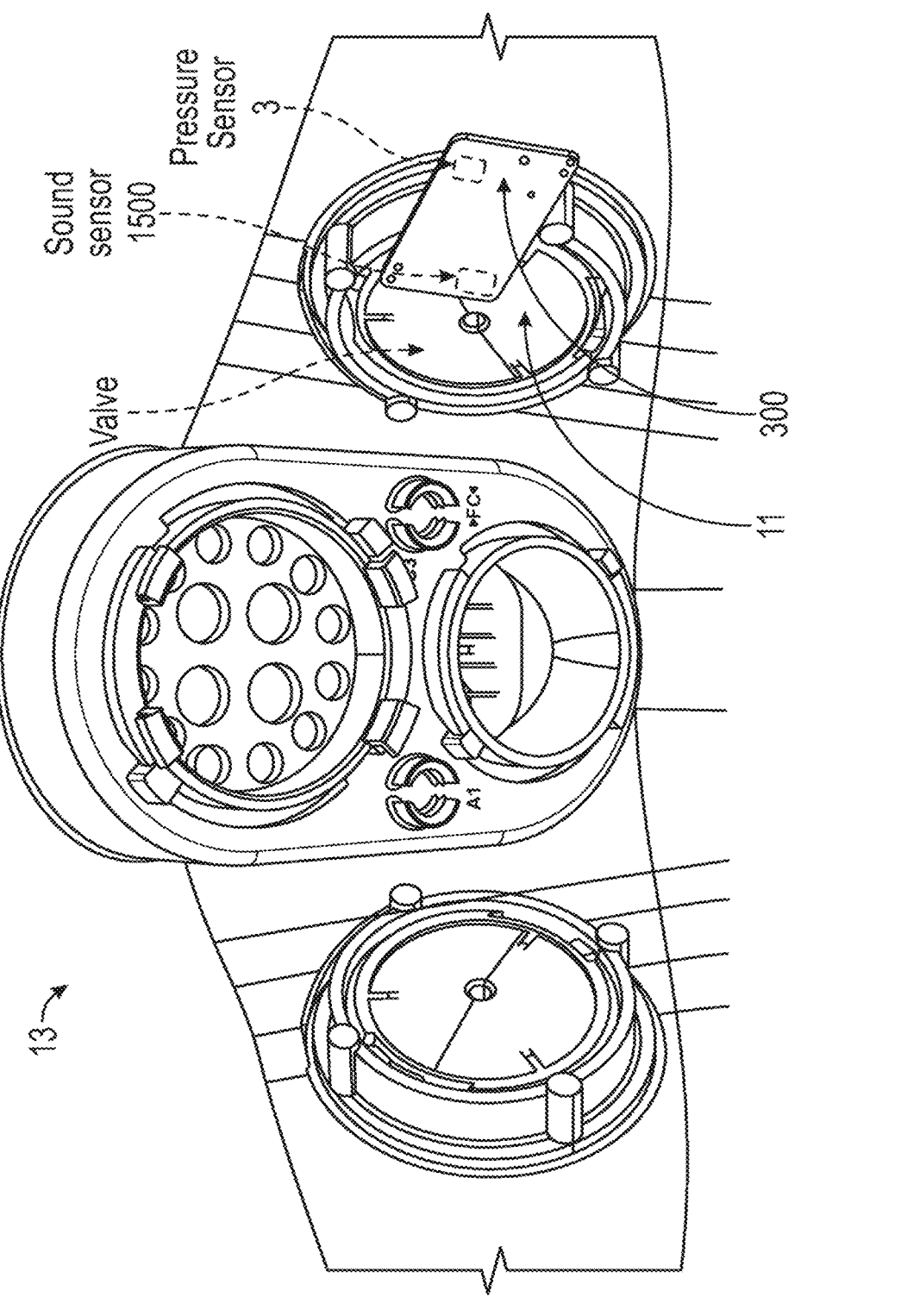
FIG. 12 is an interior perspective view of a portion of a negative pressure reusable respirator according to some embodiments of the present disclosure in which a computing device is operably coupled to a pressure sensor and at least one other sensor.

FIG. 11 is a flowchart illustrating example operations of an example computing system, in accordance with various techniques of this disclosure. FIG. 12 is described below in the context of negative pressure reusable respirator 13A of FIG. 5, PPEMS 6 of FIGS. 4 and 2, and/or computing device 300 of FIG. 8. While described in the context of negative pressure reusable respirator 13A, PPEMS 6, and/or computing device 300, other computing devices (e.g., a hub of hubs 14 of FIG. 5) may perform all or a subset of the functionality described.

In some examples, at least one computing device receives first sensor data indicative of a gas characteristic in a sealed space formed by a face of the wearer and the negative pressure reusable respirator (502). In some examples, at least one computing device receives second sensor data configured to generate second sensor data indicative of a position of the at least one valve (504). For example, negative pressure reusable respirator 13A may include a computing device 300 or may be configured to physically couple to computing device 300. In other words, computing device 300 may be integrally formed within negative pressure reusable respirator (e.g., non-removable) or may be attachable/detachable, such as for example as being operably disposed on at least one accessory 11, where accessory 11 is operably disposed on and internal or external surface of negative pressure reusable respirator 13A. In one instance, computing device 300 receives sensor data from one or more sensors configured to generate sensor data indicative of a characteristic of air within a work environment. Additionally or alternatively, PPEMS 6 may receive the sensor data. In one example, the sensor data includes data generated by a first sensor, such as an air pressure sensor 310 used to indicate air pressure within a sealable or sealed space formed (e.g., defined) by a face of worker 10A and negative pressure reusable respirator 13A. In another example, the sensor data includes data generated by a second sensor, such as a valve position sensor 311 used to indicate position of at least valve in negative pressure reusable respirator 13A. In one example, the sensor data includes data generated by a first sensor, such as an air pressure sensor 310 used to indicate air pressure within a sealable or sealed space formed (e.g., defined) by a face of worker 10A and negative pressure reusable respirator 13A and data generated by a second sensor, such as a valve position sensor 311 used to indicate position of at least valve in negative pressure reusable respirator 13A. As another example, the sensor data may include data generated by an environmental sensor (e.g., environmental sensor 312 or sensing stations 21), such as environmental data indicative of a gas or vapor concentration level within a work environment (e.g., environment 8B of FIG. 5).

The at least one computing device determines comparative data by comparing first and second sensor data to determine usage information or physical state information related to negative pressure reusable respirator 13A (506). In some embodiments, both usage information and physical state information is determined. For example, PPEMS 6 and/or computing device 300 may determine, based in first sensor data, whether the air pressure within the sealable space formed by the worker's face and negative pressure reusable respirator 13A decreases below a threshold air pressure when the worker inhales.

At least one computing device performs one or more actions in response to comparative data (508). In some examples, PPEMS 6 outputs a notification to another computing device (e.g., computing devices 16, 18 of FIG. 5) indicating usage or physical state information about the negative pressure reusable respirator. In another example, output unit 318 of computing device 300 outputs an alert to wearer indicating usage or physical state information about the negative pressure reusable respirator. In some embodiments, output unit 318 of computing device 300 outputs an alert to wearer indicating usage and physical state information about the negative pressure reusable respirator.

FIG. 12 is an interior perspective view of a portion of a negative pressure reusable respirator according to some embodiments of the present disclosure in which a computing device is operably coupled to a pressure sensor and at least one other sensor. FIG. 12 illustrates reusable respirator 13. Reusable respirator 13 may include similar or the same components, structure, and functionalities as described in FIGS. 4A-4D. In some examples, components, structure, and functionalities as described in FIGS. 4A-4D may be adapted or otherwise modified based on the examples of FIG. 12 or other examples of this disclosure.

FIG. 12 illustrates reusable respirator 13 and computing device 300 for determining state and usage information. In some examples, one or more acoustic sensors 1500 are included to determine information related to respirator fit and/or seal. Acoustic sensor 1500 may receive and convert sound waves into one or more electrical signals. The electrical signals may represent intensity, frequency, duration, variation or any other properties of the sound waves. Example acoustic sensors may include a Grove Acoustic sensor, http://wiki.seeedstudio.com/Grove-Sound_Sensor, accessed Nov. 26, 2019 and SunFounder Acoustic sensor Module, https://www.sunfounder.com/sound-sensor-module.html, accessed Nov. 26, 2019, the entire contents of each of which are hereby incorporated by reference herein in their entireties. Although the foregoing acoustic sensors are provided as examples, any suitable acoustic sensor that may be integrated (physically and/or operably) with computing device 300 and that may convert sound waves into one or more electrical signals may be used in accordance with techniques of this disclosure.

Rather than providing a respirator with ultraacoustic sensors located external to the sealed space of a respirator that are configured to merely detect either sounds generated by nasal breathing or sounds generated by an ultrasound emitter located internal to the sealed space of the respirator, example systems and techniques of FIG. 12 may use a combination of sensor data indicative of a gas characteristic in the sealed space of a respirator with sensor data indicative of sound to determine state and/or usage information of a respirator. Such state and/or usage information may not be determined by either sensor alone, or in other cases, such state and/or usage information may be significantly improved by the combination of sensor data.

In contrast to other conventional techniques, computing device 300 of FIG. 12 may automatically determine that a respirator is being worn and further determine, based at least in part by using data from acoustic sensor 1500, one or more performance characteristics of a respirator seal check by the wearer. Examples of performance characteristics may include the initiation of a seal check, the completion of a seal check, a time duration of a seal check, information associated with the quality of a seal during a seal check, such as leakage through a seal or a pass or fail indication of a seal check, and the like. In some examples, the performance of the respirator seal check indicates whether the respirator seal check has passed or failed. In some examples, the performance of the respirator seal check indicates a degree of leakage of air external to the sealed space into the sealed space. In contrast to other conventional techniques, computing device 300 of FIG. 12 may automatically determine the occurrence of a respirator seal check by a wearer and further determine, at least in part by using data from an acoustic sensor, information related to the seal of a respirator. Such information related to the seal of the respirator may include, but is not limited to: leakage into, out of, through or around a respirator seal; missing respirator components; leakage around an object used to seal a respirator flow path, such as a wearers hands or a valve; leakage associated with an action; leakage associated with a time period; leakage associated with a pressure differential; and/or a level of leakage.

In some instances, the systems and techniques of FIG. 12 may more accurately determine safety information in a shorter amount of time, creating an improved experience for an end user. Systems and techniques of FIG. 12 may provide a respirator system that can automatically determine both that a respirator is being worn and the performance of a respirator seal check by a wearer, based at least in part on sound. Acoustic sensors are decreasing in size and may be placed within a respirator. Systems and techniques of FIG. 12 may not require trained action by a user to initiate the sensor-based assessment of a seal check, in contrast to conventional methods which may require a specifically initiated, or learned, user action to initiate the sensor-based assessment of a seal check, such as initiating a computer application, or generating a specific signal spike. A system that requires no new trained user action, such as in FIG. 12, may save time and/or implementation costs for users.

In some instances, the systems and techniques of FIG. 12 may provide a respirator system that can automatically determine the occurrence of a respirator seal check conducted by a wearer and further determine information related to the quality of the seal of the respirator, based at least in part on sound. In contrast to conventional methods, the systems and techniques of FIG. 12 may automatically determine the occurrence of a respirator seal check with no new trained user action and further determine the quality of the seal based at least in part on data from a sensor indicative of sound. In some instances, it may be most beneficial to only use the data from acoustic sensor 1500 after or in response to the occurrence of a seal check that has already been determined. In some noisy environments, sound data may not be suitably reliable to determine that a respirator seal check has started but may be suitably reliable to determine information related to the seal once the occurrence of a seal check is already known. Systems and techniques of FIG. 12 may configure an acoustic sensor to operate in a low power state until a seal check occurs, which may provide power savings that can allow for smaller and/or lighter weight power sources, which may provide for a more comfortable respirator.

FIG. 12 illustrates a negative pressure reusable respirator 13 configured to be worn by a wearer and to cover at least a mouth and a nose of the wearer 10 to form a sealed space formed by a face of the wearer 10 and the negative pressure reusable respirator 13. Negative pressure reusable respirator 10 may also include at least one accessory 11, such as illustrated in FIG. 5. In some embodiments, accessory 11 is operably disposed within the sealed space. In some embodiments, accessory 11 is operably disposed on an external surface of the negative pressure reusable respirator 13. In some embodiments, accessory 11 includes a computing device 300. In some embodiments, accessory 11 includes at least one output device, such as for example, a speaker, a haptic device, a light, a graphic display device, and the like. After the wearer dons negative pressure reusable respirator 13, he/she can apply pressure to at least one contaminant capture device, in some embodiments two contaminant capture devices, inhale, and hold his/her breath or continue to inhale to maintain a negative pressure. Alternatively, after the wearer dons negative pressure reusable respirator 13, he/she can apply pressure to at least one exhalation valve or exhalation outlet path, exhale, and hold his/her breath or continue to exhale to maintain a positive pressure. In some embodiments, after a course of events, such as those presently disclosed below, the output device of accessory 11 provides at least one alert to wearer 10.

In some embodiments, negative pressure reusable respirator 13 may include at least one sensor 1500 (e.g., acoustic sensor 1500) configured to generate sensor data indicative of sound. In some embodiments, the at least one sensor 1500 is physically coupled to accessory 11. In some embodiments, the at least one sensor 1500 is physically coupled to negative pressure reusable respirator 13.

Sound waves may be generated by the use of a respirator, due to the creation of vibrational waves through the surrounding gas or the respirator itself, and these sound waves may be detected by a sensor configured to detect sound, such as acoustic sensor 1500. Sound waves may occur at different frequencies and different frequencies may superimpose to form additional signals, all of which may be detected by an appropriate sensor. For example, the movement of air through, or in proximity to, a respirator may result in measurable sounds wherein the parameters of the sound, such as frequency and/or intensity, are related to the specific movement of the air. For example, measurable sound parameters may be correlated to information related to breathing through the respirator, leaks in a respirator seal, obstruction of a respirator component, movement of respirator components such as valves, physical contact of the respirator, sounds generated by a wearer, or environmental sources of sound. In some examples, an appropriate acoustic sensor may be a microphone, an ultraacoustic sensor, or similar such sensors which are configured to detect vibrational waves through a medium.

In some embodiments, computing device 300 may determine physical state information related to the negative pressure reusable respirator 300 based at least in part on data from acoustic sensor 1500 that is configured to generate sensor data indicative of sound. In some examples, the physical state may be selected from at least one of: presence of physical components of the negative pressure reusable respirator; performance metrics of physical components of the negative pressure reusable respirator; pressure drop of the negative pressure reusable respirator; pressure drop of the negative pressure reusable respirator at different air flow rates through the respirator; ambient temperature; temperature within the negative pressure reusable respirator; composition of ambient gases in the workplace; composition of gases within the negative pressure reusable respirator; and any combinations thereof. In some embodiments, computing device 300 may be further configured to determine a change in at least one physical state of negative pressure reusable respirator 13.

In some embodiments, computing device 300 may determine that negative pressure reusable respirator 13 is being worn by a wearer. Computing device 300 may additionally determine, based at least in part on the data indicative of a sound, the performance of a respirator seal check by a wearer. In some embodiments, computing device 300 may determine usage information related to the negative pressure reusable respirator 300 based at least in part on data from acoustic sensor 1500 configured to generate sensor data indicative of sound. In some embodiments, usage information is selected from at least one of: donning of the negative pressure reusable respirator 13; doffing of the negative pressure reusable respirator 13; occlusion of an inhalation path of the negative pressure reusable respirator 13; occlusion of an exhalation path of the negative pressure reusable respirator 13; occurrence of a wearer seal check; information related to a performance procedure of a wearer seal check; information related to quality of a seal formed by the face of the wearer and the negative pressure reusable respirator 13; change in the seal formed by the face of the wearer and the negative pressure reusable respirator 13; and any combination thereof.

In some embodiments a system, such as illustrated in FIG. 12, may include a respirator 13, a first sensor 1500 configured to generate data indicative of sound, a second sensor 3 indicative of a gas characteristic in a sealed space formed by a face of a wearer and respirator 13, and a computing device 300. In the example of FIG. 12, data from different sensors may be used to determine different states and/or different usage information, and/or data from multiple sensors may be combined and/or compared to improve the determination of states and/or usage information. As an example, data from the second sensor 3 may be used to determine the stage of a respiratory cycle through a respirator, such as inhalation or exhalation, or other stage of use. Computing device 300 may then assign baseline values of data from the first sensor 1500 based on the stage of a respiratory cycle. This may enable computing device 300 to assign, for example, baseline sound values adapted to the current environment, which may differ based on differing levels of background environmental sound over time. Past, present or future data may then be compared by computing device 300 (or other computing devices) to assigned baseline values. The process of determining baseline values may also be used in reverse—the first sensor 1500 may establish a stage of a respirator cycle, or other stage of use, and the computing device 300 may assign values of the second sensor as baseline values during the established stage. In another embodiment, data from multiple sensors may be compared by the computing device 300. For example, data from an air pressure sensor 3 may be compared to data from a acoustic sensor 1500 as part of a determination of a physical state and/or usage of a respirator 13. Data may also be compared from different time periods of the same or different sensors, or different signal regimes, such as different frequencies, between the same or different sensors. For example, sensor data may be filtered by a processor (e.g., in computing device 300 and/or in a sensor itself) to provide signal information at multiple frequency bands for comparison. Comparisons may also be made between multiple sensors. For example, data may be compared between a first acoustic sensor 1500, a second air pressure sensor 3, and a third valve position sensor (not shown) as part of a process for determining usage and/or state information.

FIG. 12 illustrates an example of a system comprising a respirator 13, an acoustic sensor 1500 configured to generate data indicative of sound, and a computing device 300, wherein the computing device is configured to determine that a respirator is being worn, and then determine performance information related to a respirator seal check based at least in part on the acoustic sensor 1500. In some examples, computing device 300 determines that respirator 13 is being worn based at least in part on data from a second sensor 3 that is different than the acoustic sensor. The second sensor 3 may generate data indicative of air pressure (or a gas characteristic in a sealed space formed by a face of a wearer and a negative pressure reusable respirator). In some examples, the data indicative of sound comprises data from a first time (or time period) and data from a second time (or time period) that is different from the first time. In some examples, the data indicative of sound comprises data from a first frequency (or range of frequencies) and a second frequency (or range of frequencies). In some examples, the first and second frequencies are different. In some examples, the first and second ranges may overlap or may not overlap. In some examples, the data indicative of sound from a first time and/or first frequency is compared to data from a second time and/or second frequency. For example, data from a first time may be sound data assigned as a baseline value, and data from a second time may be sound data associated with a respirator seal check and these values may be compared as part of a determination of the quality of a respirator seal. In some examples, the data from the first time and/or the second time may include data from multiple frequencies, wherein the ratio of sound levels at different frequencies may differ depending on the level of leakage associated with a respirator during a respirator seal check. In some examples, computing device 300 provides the comparative data. For example, in some embodiments, computing device 300 may receive, and assign to memory, sensor data from one or more sensors during a first time period and may receive second data from one or more sensors during a second time period, and then provide a comparison of the sensor data from the first time period to the sensor data from a second time period. A comparison may include any number of computational operations, such as a ratio of value, and multiplication of values, an addition of values, a subtraction of values, an application of one set of values that depends on the values of another set of values, or any other useful computation combination of values. In some examples, computing device 300 provides comparative data between the sound data and data from at least one other sensor. In some examples, a performance information includes an occurrence of a respirator seal check, a duration of time related to a respirator seal check, and/or information related to the quality of a respirator seal. In some examples, computing device 300 may be configured to generate alerts and/or notifications and/or send messages based on any of the foregoing examples. In some examples, acoustic sensor 1500 and/or the computing device 300 may be physically or operably coupled to the respirator 13. In some examples, acoustic sensor 1500 and/or the computing device 300 may be physically or operably coupled to or included within an accessory of computing device 300 and/or respirator 13.

In some examples, a computing device may determine whether at least one of pressure data or acoustic data satisfies a respective threshold associated with the at least one of pressure data or acoustic data. In some examples, a computing device may determine at least one of a frequency or a frequency range indicated by the acoustic data. The computing device may determine, based at least in part on the at least one of the frequency or the frequency range, the performance of the respirator seal check. In some examples, a computing device may determine whether the at least one of the frequency or frequency range indicated by the acoustic data satisfies a threshold; and determine the performance of the respirator seal check based at least in part on whether the at least one of the frequency or frequency range indicated by the acoustic data satisfies a threshold. In some examples, a computing device may determine at least one of an amplitude or an amplitude range indicated by the acoustic data; and determine, based at least in part on the at least one of the amplitude or the amplitude range, the performance of the respirator seal check. In some examples, a computing device may determine whether the at least one of the amplitude or amplitude range indicated by the acoustic data satisfies a threshold; and determine the performance of the respirator seal check based at least in part on whether the at least one of the amplitude or amplitude range indicated by the acoustic data satisfies a threshold. In some examples, at least one of the acoustic sensor or at least one other sensor is physically integrated at an interior surface of the negative pressure reusable respirator that covers at least the mouth and the nose of the wearer to form the sealed space. In some examples, at least one of the acoustic sensor or at least one other sensor is physically integrated in an accessory that includes the computing device configured for operable coupling to the acoustic sensor and the at least one other sensor, where in the accessory is configured to be removably attached to the negative pressure reusable respirator. In some examples, to perform the at least one operation based at least in part on the performance of the respirator seal check, the at least one computing device is configured to generate an output comprising at least one of a visual, audible, or haptic output at an output interface. In some examples, to perform the at least one operation based at least in part on the performance of the respirator seal check, the at least one computing device is configured to send a message to at least one other computing device. In some examples, the at least one computing device is configured to receive a message from at least one other computing device.

In some examples, FIG. 12 illustrates a system comprising a respirator 13, a sensor 1500 configured to generate data indicative of sound, and a computing device 300, wherein the computing device 300 is configured to determine the occurrence of a respirator seal check, and determine information related to the seal of the respirator 13 based at least in part on the acoustic sensor. Further examples of this disclosure illustrate and describe example sound data that may be used as part of a determination of information related to the quality of the seal of a respirator 13. In some examples, computing device 300 may determine the occurrence of a respirator seal check based at least in part on data from a second sensor 3 that is different than the acoustic sensor 1500, wherein the second sensor is indicative of air pressure (or a gas characteristic in a sealed space formed by a face of a wearer and a negative pressure reusable respirator). In some examples, the data indicative of sound comprises data from a first time (or time period) and data from a second time (or time period). The first and second times or time periods may be different. In some examples, the data indicative of sound comprises data from a first frequency (or range of frequencies) and a second frequency (or range of frequencies). In some examples, the first and second frequencies or ranges of frequencies may be different and/or may overlap or may not overlap. In some examples, the data from a first time and/or first frequency is compared by computing device 300 to data from a second time and/or second frequency. In some examples, computing device 300 provides the comparative data. In some examples, computing device 300 may provide comparative data between the sound data and data from another sensor, for example, comparative data between an acoustic sensor and a pressure sensor, as a combination of operations described in FIGS. 13 and 17. In some examples, the information related to the respirator seal comprises data from a first sensor 1500 indicative of a sound and a second sensor 3 indicative of a gas characteristic in a sealed space formed by a face of a wearer and a negative pressure reusable respirator. In some examples, performance information may include the occurrence of a respirator seal check, the duration of time related to a respirator seal check, and/or information related to the quality of a respirator seal. In some examples, computing device 300 may be configured to generate alerts and/or notifications and/or send messages based on any of the foregoing examples. In some examples, acoustic sensor 1500 and/or the computing device 300 may be physically or operably coupled to the respirator 13. In some examples, acoustic sensor 1500 and/or the computing device 300 may be physically or operably coupled to or included within an accessory of computing device 300 and/or respirator 13.

In some examples, FIG. 12 illustrates a system comprising a respirator 13, a first sensor 1500 configured to generate data indicative of sound, a second sensor 3 indicative of a gas characteristic in a sealed space formed by a face of a wearer and a negative pressure reusable respirator and a computing device 300, wherein the computing device 300 is configured to provide comparative data by comparing the first sensor data to the second sensor data.

In some examples of FIG. 12, a respirator seal assessment apparatus 11 is disclosed. The apparatus 11 may include a first sensor 1500 configured to generate data indicative of sound, a second sensor 3 configured to generate data indicative of a gas characteristic in a sealed space formed by a face of a wearer and a negative pressure reusable respirator 13, and, a computing device 300 operatively connected to the first sensor and to the second sensor. The apparatus 11 may be configured to be operatively coupled to a respirator 13. The computing device 300 may determine that a respirator 13 is being worn based at least in part on data from first sensor 1500, for example by detecting acoustic changes due to breathing. The computing device 300 may determine that a respirator 13 is being worn based at least in part on data from the second sensor 3, for example by detecting pressure changes, air flow changes, temperature changes, composition changes, or the like due to breathing. The computing device 300 may initiate notifications to the wearer, to another computing device, or to another person based on or indicating that the respirator is being worn and a satisfactory wearer seal check has not been conducted. Notifications to the wearer may, as examples, take the form of visual, audible, or haptic feedback such as lights, sounds, or vibrations. The computing device 300 may then determine that a wearer seal check has begun based at least in part of data from the second sensor satisfying a threshold. In some examples, satisfying a threshold may include the data being greater than equal to and/or less than a threshold value. For example, the computing device 300 may determine that a wearer seal check has begun and a negative pressure is detected (in some examples, that satisfies a threshold value) due to the wearer inhaling while covering or closing the inhalation path, or when a positive pressure is detected (in some examples, less than or equal to a threshold value) due to the wearer exhaling while covering or closing the exhalation path. The computing device 300 may generate notifications based on detecting a start of a wearer seal check. The computing device 300 may then start a counting (or timer) operation. For example, the counting operation may comprise determining that a predetermined amount of time has elapsed, or determining a cumulative combination based on time and pressure, such as a time-pressure integration. The computing device 300 may monitor data from both the first sensor 1500 and the second sensor 3 during this time. If the data from the second sensor 3 satisfies a threshold, for example falls below an initiation pressure threshold value before the counting operation completes (e.g., time elapses), the computing device 300 may determine that the wearer seal check was unsatisfactory or failed. If the data from the first sensor 1500 is above or below (or equal) to a threshold, for example a sound signal or combination of sound signals is too high or too low before the counting operation completes, the computing device 300 may determine that the wearer seal check was unsatisfactory or failed. For example, if the wearer is maintaining a positive or negative pressure greater than a threshold amount relative to the ambient pressure by exhaling or inhaling while covering the flow paths, leakage through the respirator seal may generate a measurable sound or change in sound, as shown by examples in FIGS. 17-19. By using both pressure and sound measurements, the computing device 300 may determine that pressure can be maintained without air leakage through the respirator seal. The combination of sound signals may include signals at different frequencies. The thresholds for either sensor may be predetermined, or may be determined by prior data, for example data during a period before the wearer seal check began. In this way, the data threshold may be based at least in part on the levels in the environment. If both the data from the first sensor and/or the data from the second sensor satisfy the required thresholds and the counting operation completes, the wearer seal check may be determined to be satisfactory.

In some examples, a computing device may be configured to generate comparative data based at least in part on comparing at least a portion of the first sensor data to at least a portion of the second sensor data. In some examples, a computing device may be configured to select the portions of first and second sensor data, wherein the first portion of the first sensor data corresponds at least in part in time to the second portion of second sensor data; determine the comparative data based at least in part on the first portion of first sensor data and second portion of second sensor data; and determine the performance of the respirator seal check based at least in part on the comparative data. In some examples, the computing device may be configured to determine that the first portion of the first sensor data satisfies a first threshold; determine that the second portion of the second sensor data satisfies a second threshold; and determine that the first and second thresholds are satisfied within a substantially contemporaneous time duration. In some examples, a substantially contemporaneous time duration may be within 5 seconds, 10 seconds, 30 seconds, 1 minute, 5 minutes, 10 minutes, 30 minutes or 60 minutes. In some examples, comparative data comprises at least one of a likelihood that the respirator seal check has passed or failed or an indication that the respirator seal check has passed or failed. In some examples, a negative pressure reusable respirator comprises at least one valve, wherein the computing device is configured to: determine the performance of the respirator seal check by the wearer based at least in part on data that indicates a state of the at least one valve. In some examples, the state of the at least one valve comprises at least one of a position of the valve, an identifier of the valve, or data that indicates whether or a degree to which the valve is obstructed.

The computing device 300 may be configured to generate alerts at various points before, during and/or after the wearer seal check process. For example, the computing device 300 may trigger vibrations and amber lights when a respirator is being worn and a satisfactory wearer seal check has not been performed, the lights and vibrations may stop, or change color, when a wearer seal check is in process. If a wearer seal check is determined by computing device 200 to be unsatisfactory, the computing device 300 may trigger a series of red lights and vibrations, and then restart the previous amber light and vibration sequence. If a wearer seal check is determined by computing device 300 to be satisfactory, a green light and single vibration may be trigger, and then the alerts may end. Alternatively, an additional or new signal generated by computing device 300, such as a green light, or periodic green light, may occur to indicate that the satisfactory wearer seal check was previously completed.

In some examples of FIG. 12, a respirator seal assessment apparatus may include a negative pressure reusable respirator 13, a first sensor 1500 configured to generate first data indicative of sound, a second sensor 3 configured to generate second data indicative of a gas characteristic in a sealed space formed by a face of a wearer. Computing device 300 may be operatively connected to the first sensor and to the second sensor, wherein the computing device 300 may be adapted in use to determine the start of a respirator seal assessment based at least in part on the first data satisfying a threshold value; begin a counting operation; monitor data from the first sensor and second data from the second sensor, and; if the first data from the first sensor satisfies (in some examples, falls below) a threshold value before the completion of the counting operation OR if second data from the second sensor satisfies (in some examples, is above) a threshold value, determine that the respirator seal is unsatisfactory or has failed, or; if the first data from the first sensor remains above a threshold value AND if the second data from the second sensor is below a threshold value AND the counting operation completes, determine that the respirator seal is satisfactory or has passed.

In some examples of FIG. 12, sensor data (which may or may not include acoustic sensor 1500 or data from acoustic sensor 1500) may be associated with an assessment of respirator fit, such as a respirator fit test. A respirator fit test may include a determination by computing device 300 of the fit or seal of a respirator to a wearer's face during a first time period. In some embodiments, respirators, sensors and computing devices as described herein may be used during a respirator fit test to collect sensor data during a first time period. Sensor data, as examples, may include data indicative of a gas characteristic in a sealed space formed by a face of a wearer and a negative pressure reusable respirator, data indicative of air pressure, data indicative of respiratory parameters, data indicative of sound, data indicative of the presence of particulates or gases, data indicative of valve position, data indicative of conditions present in a particular environment (e g., sensors for measuring temperature, humidity, particulate content, noise levels, air quality, or any variety of other characteristics of environments in which respirator may be used), data indicative of motion of a wearer, data indicative of position and/or orientation of a respirator, a variety of other sensors, or combinations thereof. In some embodiments, sensor data from a first time period is associated with the results of a respirator fit test from a first time period. For example, a set of sensor data from a first time period may be associated with a "pass" fit test result from a first time period, or a "fail" fit test result from a first time period, or a numeric fit test result from a first time period. In some examples, computing device 300 may store data, such as labels or other discrete values that represent "pass" and "fail". In some examples, confidence values that indicate the likelihood of "pass" or "fail" may be associated with the respective labels or other discrete values. In some examples, a fit test result and associated sensor data from a first time period includes fit test results and associated sensor data from a set of time periods.

In some examples, an analytics engine may process sensor data from a first time period and respirator fit test result data from a first time period, along with sensor data during a second time period, in the determination of state and/or usage information associated with a respirator during a second time period. For instance, an analytics engine, such as analytics service 68F of FIG. 7 (which may also be implemented at computing device 300 of FIG. 8 or a combination of computing devices in FIGS. 5, 7, 8) may apply, based at least in part on respirator fit test result data from a first time period, the particular sensor data from a first time period to a respirator state and/or usage information model. The respirator state and/or usage information model may then be used as part of a determination of respirator state and/or usage information during a second time period. For example, sensor data from a first time period and respirator fit test result data from a first time period may be used may be used, along with sensor data during a second time period, to determine respirator state and/or usage information during a second time period. For example, the respirator state and/or usage information model may be used to determine the fit and/or seal of a respirator during respirator use in a workplace.

In some examples, while the negative pressure reusable respirator is in current use by the wearer, a computing device may receive the sensor data usable to determine the performance of the respirator seal check. The computing device may determine, based at least in part on the sensor data usable to determine the performance of the respirator seal check generated during a fit-test that occurred prior to the current use of the negative pressure reusable respirator by the wearer, a performance of a respirator seal check by the wearer. The computing device may perform at least one operation based at least in part on the performance of the respirator seal check.

In some examples, the respirator state and/or usage information model may be implemented using one or more learning, statistical, or other suitable techniques. Example learning techniques that may be employed to generate and/or configure models can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbor (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR). In some embodiments, an analytics engine applies sensor data and/or respirator fit test result data from a plurality of first time periods, fit tests, workers, populations of workers, geographic regions, or combinations thereof to a respirator state and/or usage information model.

In some examples of FIG. 12 (which may or may not include acoustic sensor 1500 or data from acoustic sensor 1500), the respirator 13 may include a mechanical mechanism, or multiple mechanical mechanisms, for altering a flow path through a respirator, such as a valve, an actuator, a closure, or the like. In some embodiments, a mechanical mechanism may be actuated by an air pressure differential during breathing, such as a valve. A mechanical mechanism may also by actuated by non-breathing based mechanisms, such as by an applied external force or an electromechanical force. In some embodiments, the mechanical mechanism may be a shut-off valve operable between a closed position and an open position, wherein the shut-off valve includes an actuator formed of a flange and a span extending from the flange, the span exhibiting varying thickness such that, when operated from the open position to the closed position, the actuator provides tactile feedback in response to an applied force placed on the actuator, such as described in PCT Publication Number WO2015/179156, entitled RESPIRA-TOR NEGATIVE PRESSURE FIT CHECK DEVICES AND METHODS, filed May 11, 2015, the entire contents of which is hereby incorporated by reference herein in its entirety. In some embodiments, the state of a mechanical mechanism or any other data related to the mechanical mechanism may be communicated to a computing device 300, for example the position of a valve or if a mechanical mechanism has been actuated. In some embodiments, the mechanical mechanism may include a sensing device to sense the state of the mechanical mechanism, and a computing device 300 may be configured to receive data from a sensing device. In some embodiments, the mechanical mechanism may be configured to block the inward flow of air into the respirator and may be actuated by a respirator wearer as part of a respirator seal check. In some embodiments, the computing device 300 may be configured to receive state information from the mechanical mechanism and receive other sensor data associated with state and/or usage information of the respirator. Some examples of other sensor data may include data indicative of a gas characteristic in a sealed space formed by a face of a wearer and a negative pressure reusable respirator, data indicative of sound, data indicative of a valve position, data indicative of proximity of facial features to a respirator, data indicative of facial features, and the like. In some embodiments, the computing device 300 may configured to use state information from the mechanical mechanism and other sensor data associated with state and/or usage information of the respirator in order to determine information associated with the performance of a respirator seal check, such as the time of the check, the quality of the check, the quality of the seal of the respirator to the wearer's face, and the like.

In some examples of FIG. 12 (which may or may not include acoustic sensor 1500 or data from acoustic sensor 1500), the respirator 13 may include one or more sensors to determine whether a wearer's mouth is open during a seal-check or fit-test. For example, to obtain a reliable and/or accurate determination of whether a seal-check or fit-test passed or failed, it may be necessary for a wearer's mouth to be open for at least a portion of the time during which the collection of sensor data and/or determination of pass/fail is performed by the computing device. In some examples, apparatus 11 may include one or more sensors that generate data usable to determine whether a wearer's mouth is open. In some examples, a wearer's mouth is open when an aperture size of the wearer's mouth satisfies a threshold value (e.g., is greater than or equal to the threshold value). In some examples, sensors that generate data usable to determine whether a wearer's mouth is open may include one or more of an infrared sensor, optical sensor, distance sensor, temperature sensor, acoustic sensor, or any other sensor that is capable of determining whether a wearer's mouth is open. In some examples, computing device 300 may determine whether the wearer's mouth is open based on sensor data from the one or more sensors that are capable of determine whether a wearer's mouth is open. Computing device 300 may determine whether the wearer's mouth is open during at least a portion of a duration of a seal-check or fit-test. In some examples, computing device 300 may determine that the wearer's mouth is not open during at least a portion of a duration of a seal-check or fit-test. Computing device 300 may determine that the seal-check or fit-test has failed based at least in part on determining that the wearer's mouth was not open during at least a portion of a duration of a seal-check or fit-test. In some examples, computing device 300 may determine that the wearer's mouth is open during at least a portion of a duration of a seal-check or fit-test. Computing device 300 may determine that the seal-check or fit-test has passed based at least in part on determining that the wearer's mouth was open during at least a portion of a duration of a seal-check or fit-test.

Figure 13:
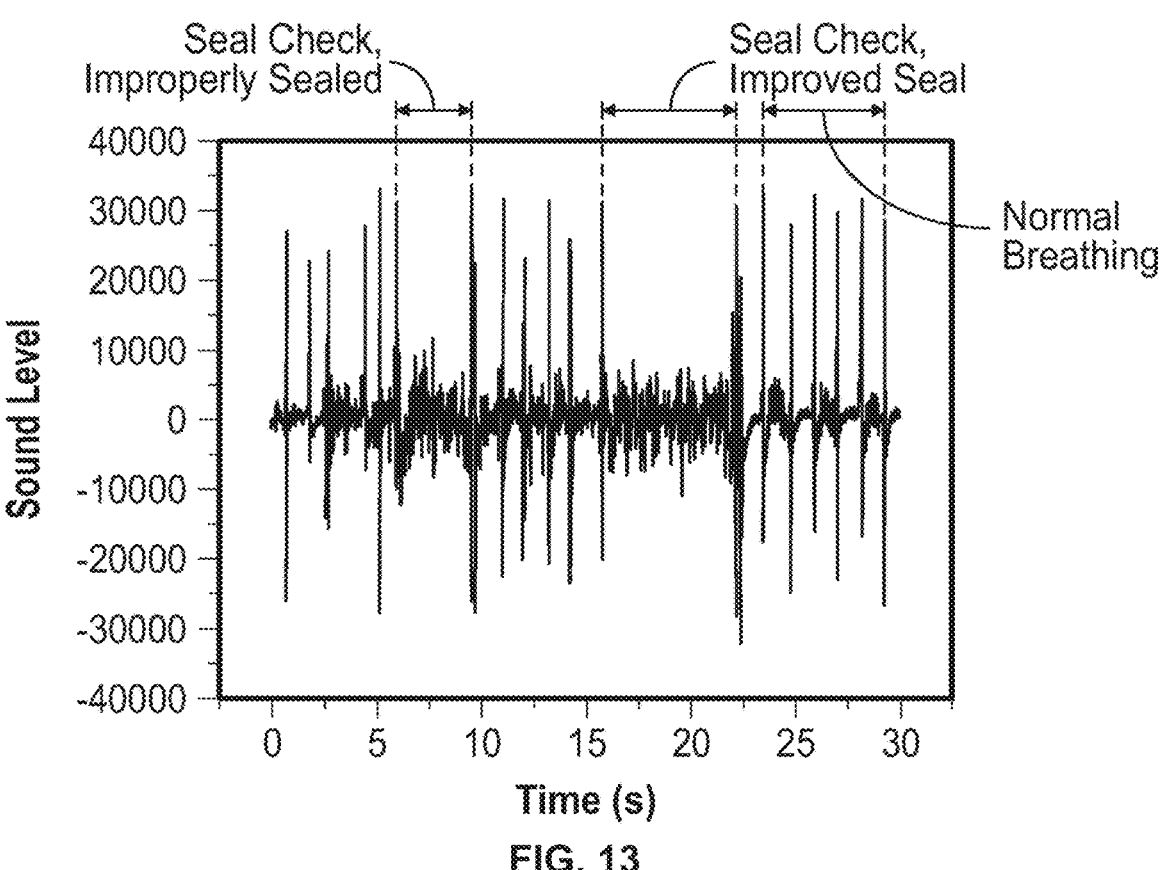
FIG. 13 illustrates sensor data in accordance with techniques of this disclosure.

FIG. 13 illustrates sensor data in accordance with techniques of this disclosure. For example, FIG. 13 illustrates raw acoustic sensor data from within the sealed space of a respirator during a respirator seal check when (a) the respirator is improperly sealed, (b) a respirator seal check when the respirator seal is improved, and (c) normal breathing.

Figure 14:
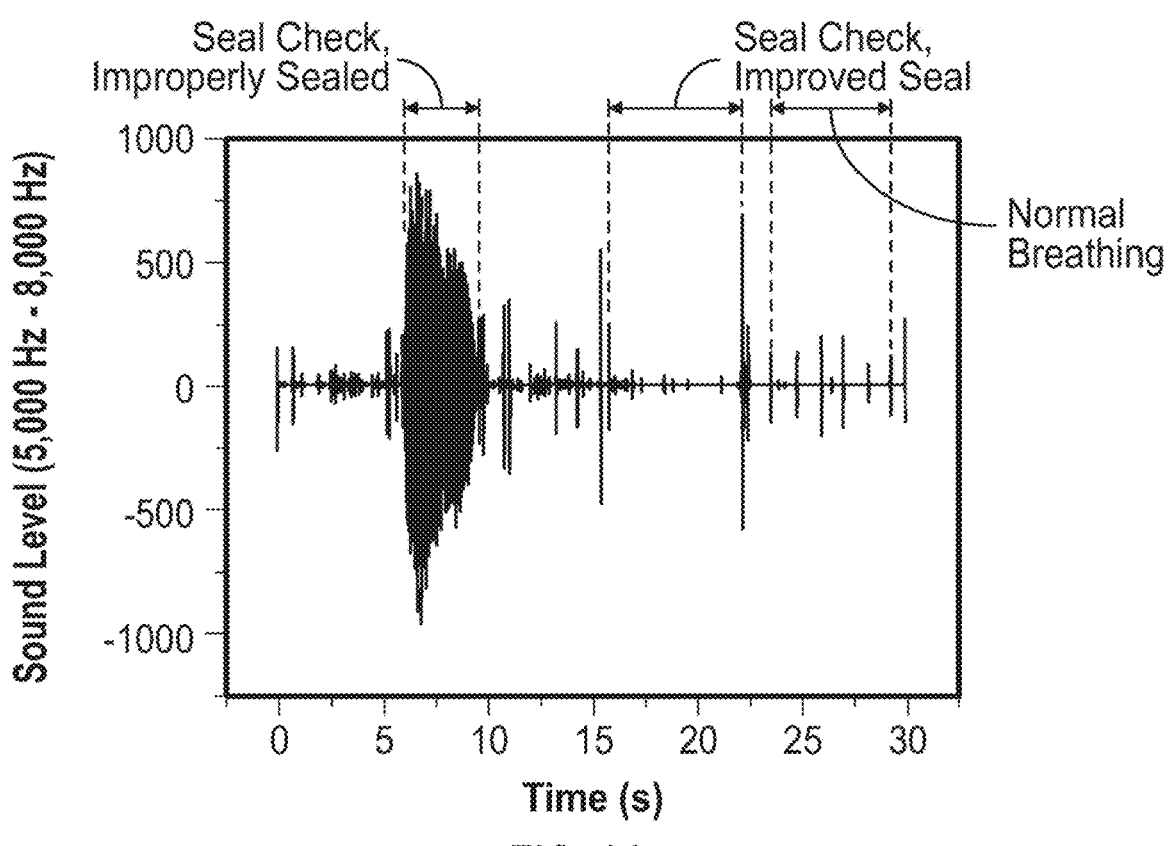
FIG. 14 illustrates sensor data in accordance with techniques of this disclosure.

FIG. 14 illustrates sensor data in accordance with techniques of this disclosure. For example, FIG. 14 illustrates filtered acoustic sensor data from within the sealed space of a respirator during (a) a respirator seal check when the respirator is improperly sealed, (b) a respirator seal check when the respirator seal is improved, and (c) normal breathing.

Figure 15:
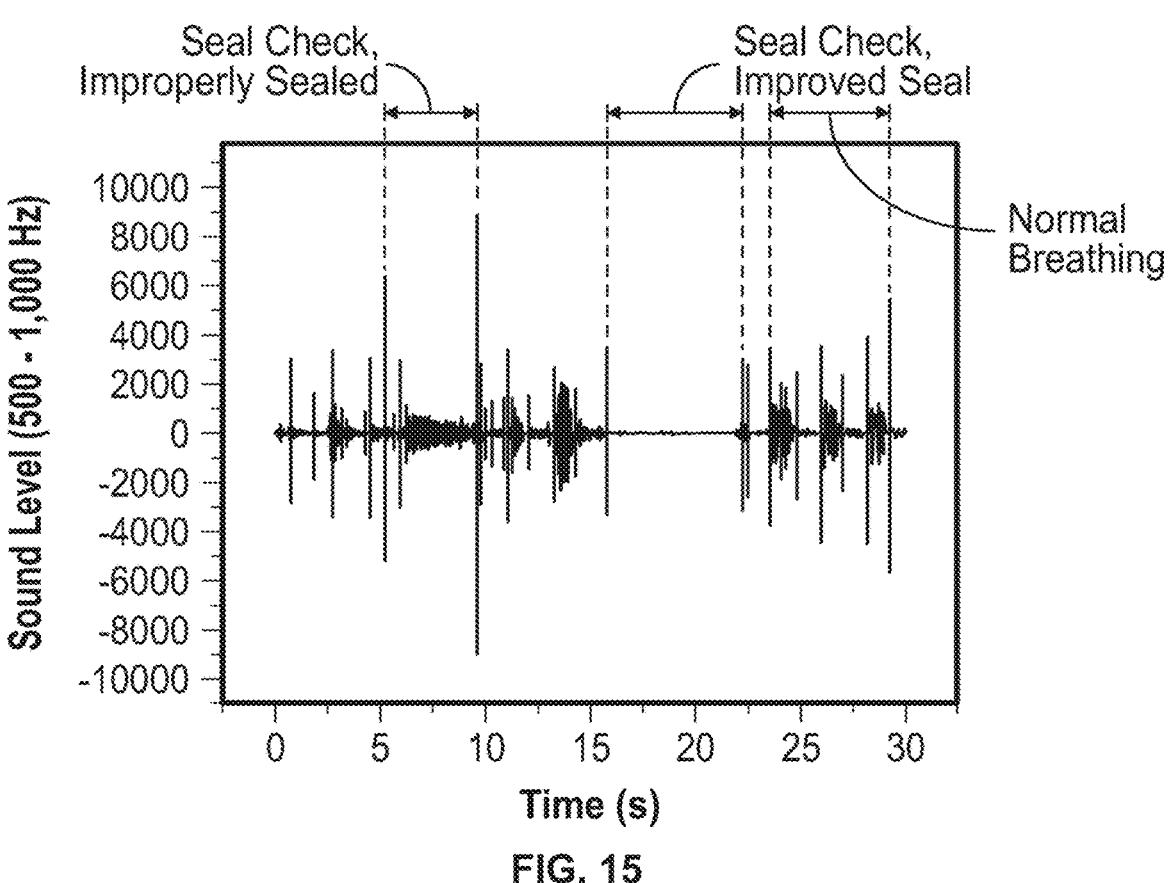
FIG. 15 illustrates sensor data in accordance with techniques of this disclosure.

FIG. 15 illustrates sensor data in accordance with techniques of this disclosure. For example, FIG. 15 illustrates filtered acoustic sensor data from within the sealed space of a respirator during (a) a respirator seal check when the respirator is improperly sealed, (b) a respirator seal check when the respirator seal is improved, and (c) normal breathing.

Figure 16:
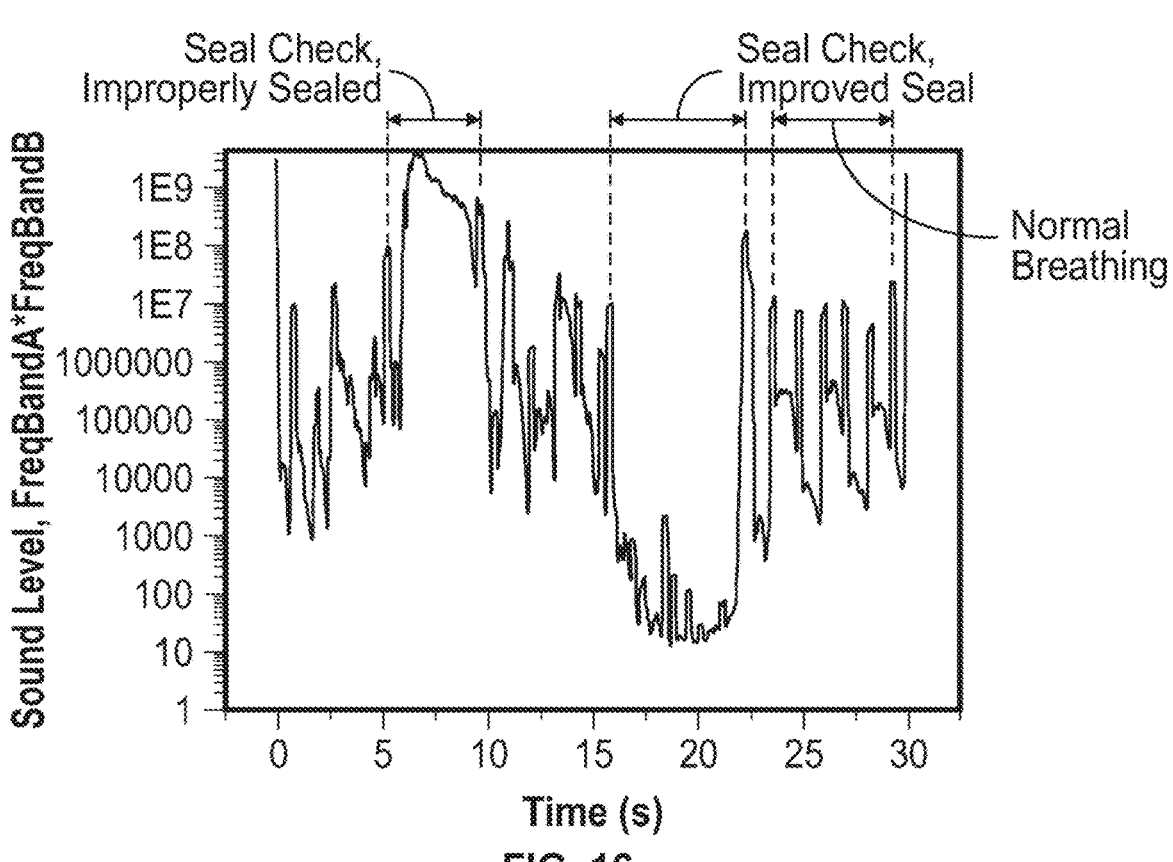
FIG. 16 illustrates sensor data in accordance with techniques of this disclosure.

FIG. 16 illustrates sensor data in accordance with techniques of this disclosure. For example, FIG. 16 illustrates combination of acoustic sensor data from an acoustic sensor of a respirator filtered at different frequency bands.

Figure 17:
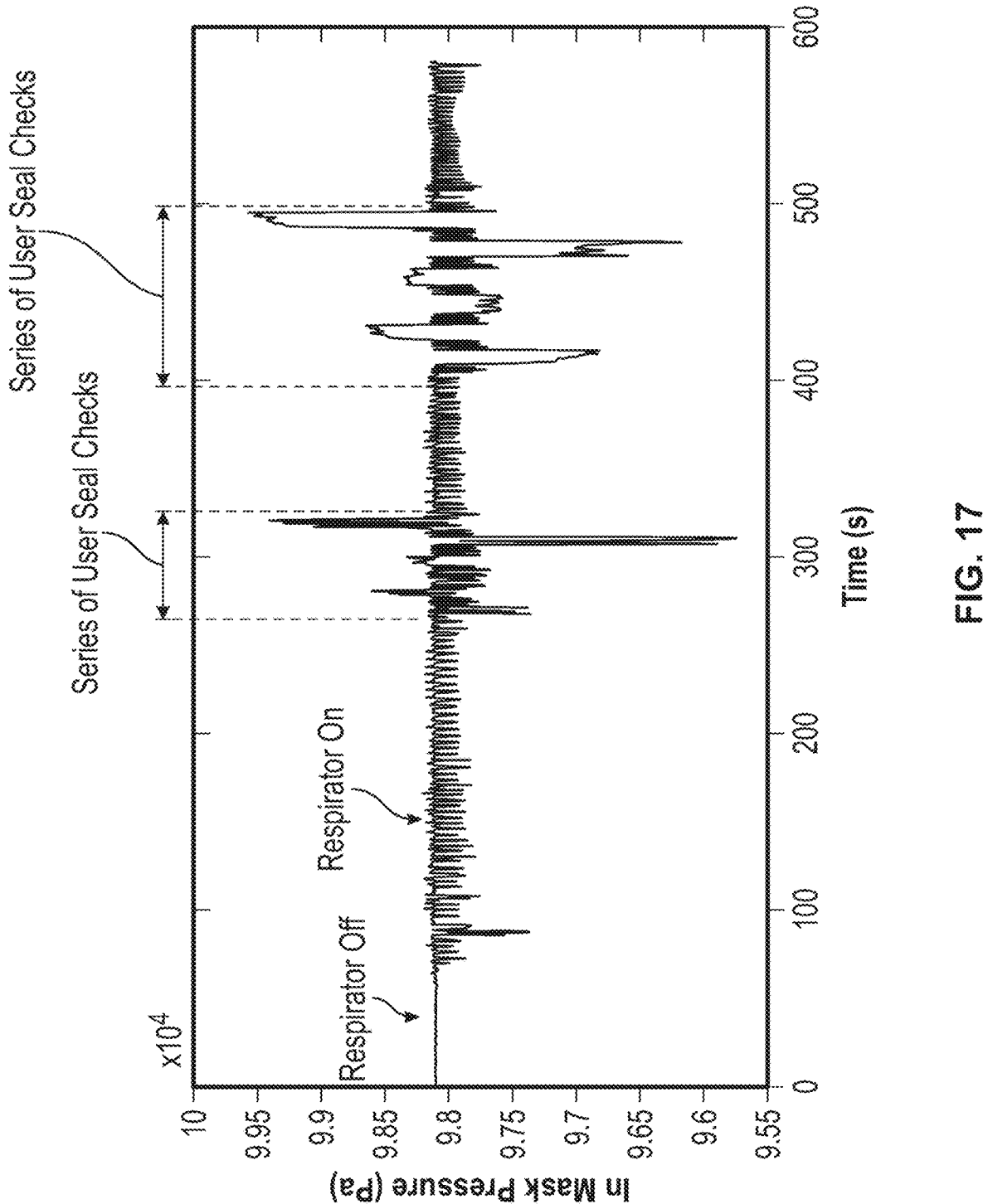
FIG. 17 illustrates sensor data in accordance with techniques of this disclosure.

FIG. 17 illustrates sensor data in accordance with techniques of this disclosure. For example, FIG. 17 illustrates exemplary pressure data indicative of whether a respirator is being worn and indicative of the occurrence of a respirator seal check.

The techniques, systems, components, and apparatuses in any of the disclosed examples of the various FIGS. may be employed in a variety of means towards assessing the seal of a respirator. For example, implementations in any of the example FIGS. described for a wearer seal check may also be used for a user seal check, a respirator fit check, a respirator fit test, and/or other use cases for assessing the seal of a respirator.

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

What is claimed is:

1. A system comprising:
   a negative pressure reusable respirator configured to be worn by a wearer and to cover at least a mouth and a nose of the wearer to form a sealed space formed by a face of the wearer and the negative pressure reusable respirator;
   a first sensor configured to generate first sensor data indicative of a gas characteristic in the sealed space;
   a second sensor configured to generate second sensor data indicative of sound in the sealed space;

at least one computing device comprising:
      at least one processor; and
      a memory storing instructions that, when executed by the at least one processor, cause the at least one processor to:
         determine, based at least in part on both the first sensor data and the second sensor data, a performance characteristic of a respirator seal check performed by the wearer;
         generate comparative data based at least in part on comparing at least a portion of the first sensor data with at least a portion of the second sensor data; and
         perform at least one operation based at least in part on the performance characteristic of the respirator seal check, wherein the at least one operation comprises generating an output that is perceptible by the wearer.

2. The system of claim 1, wherein the performance characteristic of the respirator seal check indicates whether the respirator seal check has passed or failed.

3. The system of claim 1, wherein the performance characteristic of the respirator seal check indicates a degree of leakage of air external to the sealed space into the sealed space.

4. The system of claim 1, wherein the at least one computing device is configured to:
   select the portions of first and second sensor data, wherein the first portion of the first sensor data corresponds at least in part in time to the second portion of second sensor data;
   determine the comparative data based at least in part on the first portion of first sensor data and second portion of second sensor data; and
   determine the performance characteristic of the respirator seal check based at least in part on the comparative data.

5. The system of claim 4, wherein to determine the comparative data based at least in part on the first portion of first sensor data and second portion of second sensor data, the computing device is configured to:
   determine that the first portion of the first sensor data satisfies a first threshold;
   determine that the second portion of the second sensor data satisfies a second threshold; and
   determine that the first and second thresholds are satisfied within a substantially contemporaneous time duration.

6. The system of claim 4, wherein the comparative data comprises at least one of a likelihood that the respirator seal check has passed or failed or an indication that the respirator seal check has passed or failed.

7. The system of claim 1, wherein the negative pressure reusable respirator comprises at least one valve, wherein the computing device is configured to:
   determine the performance characteristic of the respirator seal check by the wearer based at least in part on data that indicates a state of the at least one valve.

8. The system of claim 7, wherein the state of the at least one valve comprises at least one of a position of the valve, an identifier of the valve, or data that indicates whether or a degree to which the valve is obstructed.

9. The system of claim 8, wherein to perform the at least one operation based at least in part on the performance characteristic of the respirator seal check, the at least one computing device is configured to generate an output comprising at least one of a message for at least one other computing device or a visual, audible, or haptic output at an output interface.

10. A computing device comprising:

at least one processor; and a memory comprising instructions that, when executed by the at least one processor, cause the at least one processor to:

receive, from a first sensor, first sensor data indicative of a gas characteristic in a sealed space formed by a face of the wearer and a negative pressure reusable respirator, wherein the negative pressure reusable respirator is configured to be worn by the wearer and to cover at least the mouth and the nose of the wearer to form the sealed space;

receive, from a second sensor, second sensor data indicative of sound in the sealed space;

determine, based at least in part on both the first sensor data and the second sensor data, a performance characteristic of a respirator seal check performed by the wearer;

generate comparative data based at least in part on comparing at least a portion of the first sensor data with at least a portion of the second sensor data; and perform at least one operation based at least in part on the performance characteristic of the respirator seal check, wherein the at least one operation comprises generating an output that is perceptible by the wearer.

11. The computing device of claim 10, wherein the performance characteristic of the respirator seal check indicates whether the respirator seal check has passed or failed.

12. The computing of claim 10, wherein the performance characteristic of the respirator seal check indicates a degree of leakage of air external to the sealed space into the sealed space.

13. The computing device of claim 10, wherein the memory comprises instructions that, when executed by the at least one processor, cause the at least one processor to:

select the portions of first and second sensor data, wherein the first portion of the first sensor data corresponds at least in part in time to the second portion of second sensor data;

determine the comparative data based at least in part on the first portion of first sensor data and second portion of second sensor data; and determine the performance characteristic of the respirator seal check based at least in part on the comparative data.

14. The computing device of claim 13, wherein to determine the comparative data based at least in part on the first portion of first sensor data and second portion of second sensor data, the memory comprises instructions that, when executed by the at least one processor, cause the at least one processor to:

determine that the first portion of the first sensor data satisfies a first threshold;

determine that the second portion of the second sensor data satisfies a second threshold; and determine that the first and second thresholds are satisfied within a substantially contemporaneous time duration.

15. The computing device of claim 14, wherein the comparative data comprises at least one of a likelihood that the respirator seal check has passed or failed or an indication that the respirator seal check has passed or failed.

16. The computing device of claim 10, wherein the negative pressure reusable respirator comprises at least one valve, wherein the computing device is configured to:

determine the performance characteristic of the respirator seal check by the wearer based at least in part on data that indicates a state of the at least one valve.

17. The computing device of claim 10, wherein the state of the at least one valve comprises at least one of a position of the valve, an identifier of the valve, or data that indicates whether or a degree to which the valve is obstructed.

18. The computing device of claim 17, wherein to perform the at least one operation based at least in part on the performance characteristic of the respirator seal check, the memory comprises instructions that, when executed by the at least one processor, cause the at least one processor to generate an output comprising at least one of a message for at least one other computing device or a visual, audible, or haptic output at an output interface.

* * * * *